US010808003B2

(12) United States Patent
Chae et al.

(10) Patent No.: US 10,808,003 B2
(45) Date of Patent: Oct. 20, 2020

(54) AMPHIPATHIC MOLECULE BASED ON TANDEM MALONATE AND USE THEREOF

(71) Applicant: Industry-University Cooperation Foundation Hanyang University Erica Campus, Ansan-si (KR)

(72) Inventors: Pil Seok Chae, Ansan-si (KR); Hazrat Hussain, Ansan-si (KR)

(73) Assignee: Industry-University Cooperation Foundation Hanyang University Erica Campus, Ansan-si (KR)

( * ) Notice: Subject to any disclaimer, the term of this patent is extended or adjusted under 35 U.S.C. 154(b) by 0 days.

(21) Appl. No.: 16/604,168

(22) PCT Filed: Apr. 21, 2017

(86) PCT No.: PCT/KR2017/004258
§ 371 (c)(1),
(2) Date: Oct. 10, 2019

(87) PCT Pub. No.: WO2018/190452
PCT Pub. Date: Oct. 18, 2018

(65) Prior Publication Data
US 2020/0048297 A1    Feb. 13, 2020

(30) Foreign Application Priority Data

Apr. 13, 2017    (KR) ........................ 10-2017-0047889

(51) Int. Cl.
| | | |
|---|---|---|
| *C07H 15/14* | (2006.01) | |
| *C07H 15/26* | (2006.01) | |
| *C07H 15/04* | (2006.01) | |
| *C07H 15/18* | (2006.01) | |
| *C07H 15/24* | (2006.01) | |
| *G01N 33/68* | (2006.01) | |

(52) U.S. Cl.
CPC ............. *C07H 15/14* (2013.01); *C07H 15/04* (2013.01); *C07H 15/18* (2013.01); *C07H 15/24* (2013.01); *C07H 15/26* (2013.01); *G01N 33/68* (2013.01)

(58) Field of Classification Search
None
See application file for complete search history.

(56) References Cited

U.S. PATENT DOCUMENTS

2013/0001465 A1* 1/2013 Gellman ................ C07H 15/02
252/182.12

FOREIGN PATENT DOCUMENTS

WO    WO 2018/190452    10/2018

OTHER PUBLICATIONS

International Search Report and the Written Opinion dated Jan. 12, 2018 From the International Searching Authority Re. Application No. PCT/KR2017/004258 and Its Translation of Search Report Into English. (11 Pages).
Chae et al. "Glucose-Neopentyl Glycol (GNG) Amphiphiles for Membrane Protein Study", Chemical Communications, 49(23): 2287-2289, Mar. 21, 2013.
Chae et al. "Tripod Amphiphiles for Membrane Protein Manipulation", Molecular BioSystems, 6(1): 89-94, Published Online Oct. 14, 2009.
Ehsan et al. "Highly Branched Pentasaccharide-Bearing Amphiphiles for Membrane Protein Studies", Journal of the American Chemical Society, JACS, 138(11): 3789-3796, Published Online Mar. 11, 2016.
Ilker et al. "Modular Norbornene Derivatives for the Preparation of Well-Defined Amphiphilic Polymers: Study of the Lipid Membrane Disruption Activities", Macromolecules, 37(3): 694-700, Published on Web Jan. 16, 2004.

* cited by examiner

*Primary Examiner* — Traviss C McIntosh, III

(57) ABSTRACT

Provided are a newly developed tandem malonate-based amphipathic molecule, a method of preparing the same, and a method of extracting, solubilizing, stabilizing, crystallizing or analyzing a membrane protein using the same. In addition, the compound may be used to efficiently extract membrane proteins having various structures and characteristics from a cell membrane, compared to a conventional compound, to stably store the proteins in an aqueous solution for a long time, and may be used in functional and structural analysis thereof. The analysis of the structures and functions of the membrane proteins is one of the most attractive fields in current biology and chemistry, which are closely related to new drug development.

19 Claims, 16 Drawing Sheets

AMPHIPATHIC MOLECULE BASED ON TANDEM MALONATE AND USE THEREOF

RELATED APPLICATIONS

This application is a National Phase of PCT Patent Application No. PCT/KR2017/004258 having International filing date of Apr. 21, 2017, which claims the benefit of priority of Korean Patent Application No. 10-2017-0047889 filed on Apr. 13, 2017. The contents of the above applications are all incorporated by reference as if fully set forth herein in their entirety.

FIELD AND BACKGROUND OF THE INVENTION

The present invention relates to a newly-developed tandem malonate-based amphipathic molecule, a method of preparing the same, and a method of extracting, solubilizing, stabilizing, crystallizing or analyzing membrane proteins using the same.

Membrane proteins play important roles in biological systems. Since such bio-macromolecules include hydrophilic and hydrophobic domains, amphipathic molecules are necessary to extract membrane proteins from a cell membrane, and solubilize and stabilize the proteins in an aqueous solution.

For structural analysis of membrane proteins, it is necessary to obtain high quality membrane protein crystals, and to this end, structural stabilization of the membrane proteins in an aqueous solution should be preceded. While there are more than 100 conventional amphipathic molecules which have been used in research on membrane proteins, only approximately five of them have been actively used in research on the structure of membrane proteins. These five amphipathic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (Non-Patent Literatures 1 and 2). However, since many membrane proteins surrounded by these molecules tend to rapidly lose their functions due to easy structural denaturation or agglomeration, there are considerable limitations to research on the functions and structures of the membrane proteins utilizing these molecules. It is because conventional molecules do not exhibit various characteristics due to their simple chemical structures.

Particularly, in the research for structural analysis through crystallization of membrane proteins, compared to molecules including a maltoside, amphipathic molecules including a glucoside as a hydrophilic group are generally being widely used in structural analysis through crystallization of membrane proteins despite an overall decrease in ability to stabilize the membrane proteins. For example, in general, compared to DDM, OG or NG is remarkably decreased in ability to stabilize membrane proteins, but is still being widely used in the research on the structures of membrane proteins. Therefore, if the ability of the amphipathic molecules including a glucoside to stabilize membrane proteins can be greatly improved, the amphipathic molecules will be widely used to determine the structures of the membrane proteins. However, up to now, amphipathic molecules having glucose as a hydrophilic group have many limitations because they are not excellent for stabilization of membrane proteins. Specifically, amphipathic molecules including two glucosides, glucose-neopentyl glycols (GNGs), which have been previously disclosed, have a superior ability to crystallize membrane proteins, but have an inferior ability to stabilize membrane proteins, compared to DDM (Non-Patent Literature 3). For this reason, it is necessary to develop a novel glucoside amphipathic substance having a novel and excellent characteristic through the design of a novel structure.

Therefore, the inventors developed an amphipathic molecule in which a hydrophobic group and a hydrophilic group are introduced to a tandem malonate backbone, and identified an excellent membrane protein stabilization characteristic of the compound, and thus the present invention was completed.

Non-Patent Literature (Non-Patent Literature 1) S. Newstead et al., *Protein Sci.* 17 (2008) 466-472.
(Non-Patent Literature 2) S. Newstead et al., *Mol. Membr. Biol.* 25 (2008) 631-638
(Non-Patent Literature 3) P. S. Chae et al., *Chem. Commun.* 49, (2013), 2287-2289

SUMMARY OF THE INVENTION

The present invention is directed to providing a compound represented by Formula 1.

The present invention is also directed to providing a composition for extracting, solubilizing, stabilizing, crystallizing or analyzing membrane proteins including the compound.

The present invention is also directed to providing a method of preparing the compound.

The present invention is also directed to providing a method of extracting, solubilizing, stabilizing, crystallizing or analyzing membrane proteins including the compound.

In one exemplary embodiment of the present invention, a compound represented by Formula 1 is provided:

[Formula 1]

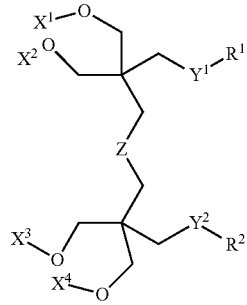

In Formula 1, $R^1$ and $R^2$ may be each independently a substituted or unsubstituted $C_3$-$C_{30}$ alkyl group, a substituted or unsubstituted $C_3$-$C_{30}$ cycloalkyl group, a substituted or unsubstituted $C_3$-$C_{30}$ aryl group, or an organic group having a steroid backbone;

each of $X^1$ to $X^4$ may be a saccharide;
each of $Y^1$ and $Y^2$ may be $CH_2$, O or S; and
Z may be $CH_2$ or S.

The term "saccharide" used herein refers to a compound that has a relatively small molecule and has sweetness when dissolved in water among carbohydrates. Saccharides are classified into monosaccharides, disaccharides and polysaccharides according to the number of molecules constituting a saccharide.

The saccharide used in the exemplary embodiment may be a monosaccharide or disaccharide, and specifically glucose or maltose, but the present invention is not limited thereto.

The saccharide may serve as a hydrophilic group. When the compound according to one exemplary embodiment of the present invention forms a complex with a membrane protein, the compound has a reduced size by linking four saccharides as hydrophilic groups in parallel to minimize an increase in the length of the hydrophilic groups while increasing the size of the hydrophilic groups. When the complex of the compound and the membrane proteins is small, high quality membrane protein crystals may be obtained (G. G. Prive, *Methods* 2007, 41, 388-397).

In addition, $R^1$ and $R^2$ may serve as hydrophobic groups. The compound according to an exemplary embodiment of the present invention contains two hydrophobic groups to optimize a hydrophile-lipophile balance.

The compound according to an exemplary embodiment of the present invention may have a tandem malonate linker as a backbone. That is, the compound is an amphipathic molecule in which four hydrophilic groups and two hydrophobic groups are introduced to tandem malonate as a backbone, and may exhibit excellent performance in membrane protein stabilization and crystallization.

Specifically, $R^1$ and $R^2$ may be each independently a substituted or unsubstituted $C_3$-$C_{30}$ alkyl group or an organic group having a steroid backbone; and each of $X^1$ to $X^4$ may be glucose or maltose; each of $Y^1$ and $Y^2$ may be $CH_2$, O or S; and Z may be $CH_2$ or S. In the present invention, such compounds are named "tandem malonate-based glucosides/maltosides (TMGs/TMMs)."

More specifically, $R^1$ and $R^2$ may be each independently a substituted or unsubstituted $C_3$-$C_{30}$ alkyl group; each of $X^1$ to $X^4$ may be glucose; each of $Y^1$ and $Y^2$ may be $CH_2$; and Z may be $CH_2$. In the present invention, such compounds are named "TMG-As."

Further more specifically, $R^1$ and $R^2$ may be each independently a substituted or unsubstituted $C_3$-$C_{30}$ alkyl group or an organic group having a steroid backbone; each of $X^1$ to $X^4$ may be glucose or maltose; each of $Y^1$ and $Y^2$ may be O; and Z may be S. In the present invention, such compounds are named "tandem malonate-based glucosides/maltosides (TMG-Ts/TMMs)."

In one exemplary embodiment of the present invention, the compound represented by Formula 1 is any one of the compounds in which each of $R^1$ and $R^2$ is a $C_9$ alkyl group; each of $X^1$ to $X^4$ is glucose; each of $Y^1$ and $Y^2$ is O; and Z is S, and is named "TMG-T11." Therefore, the compound may be a compound represented by Formula 2 below:

[Formula 2]

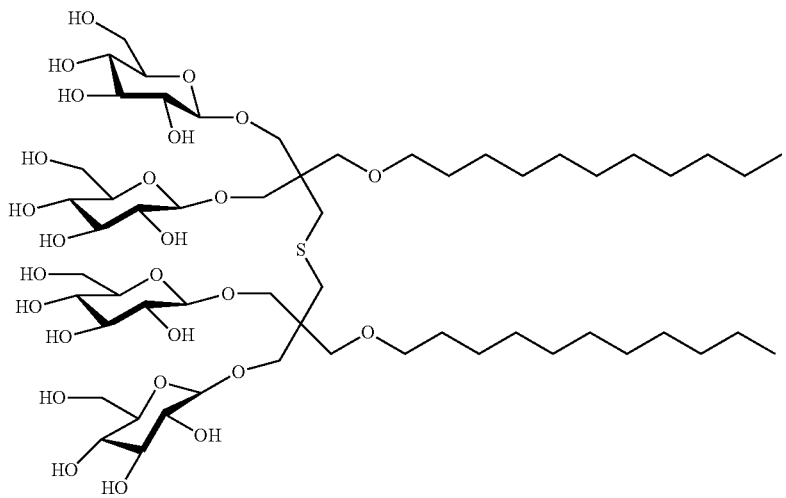

In one exemplary embodiment of the present invention, the compound represented by Formula 1 is any one of the compounds in which each of $R^1$ and $R^2$ is a $C_{10}$ alkyl group; each of $X^1$ to $X^4$ is glucose; each of $Y^1$ and $Y^2$ is O; and Z is S, and is named "TMG-T12." Therefore, the compound may be a compound represented by Formula 3 below:

[Formula 3]

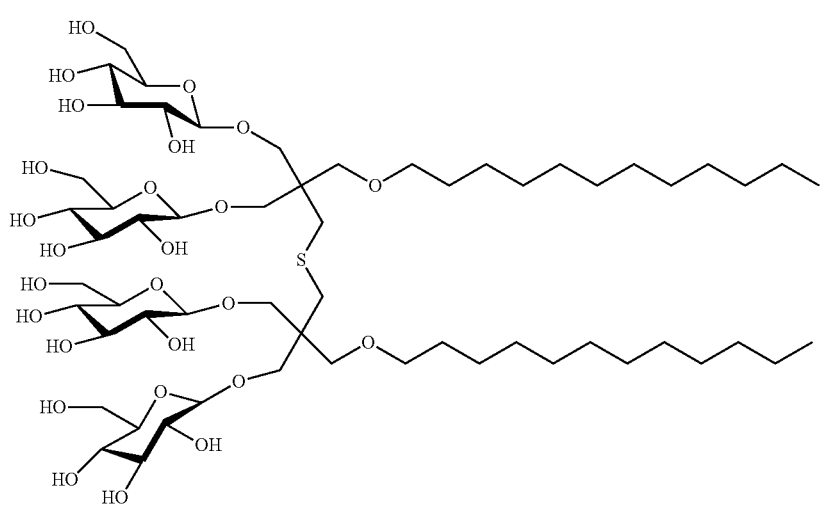

In one exemplary embodiment of the present invention, the compound represented by Formula 1 is any one of the compounds in which each of $R^1$ and $R^2$ is a $C_{11}$ alkyl group; each of $X^1$ to $X^4$ is glucose; each of $Y^1$ and $Y^2$ is O; and Z is S, and is named "TMG-T13." Therefore, the compound may be a compound represented by Formula 4 below:

[Formula 4]

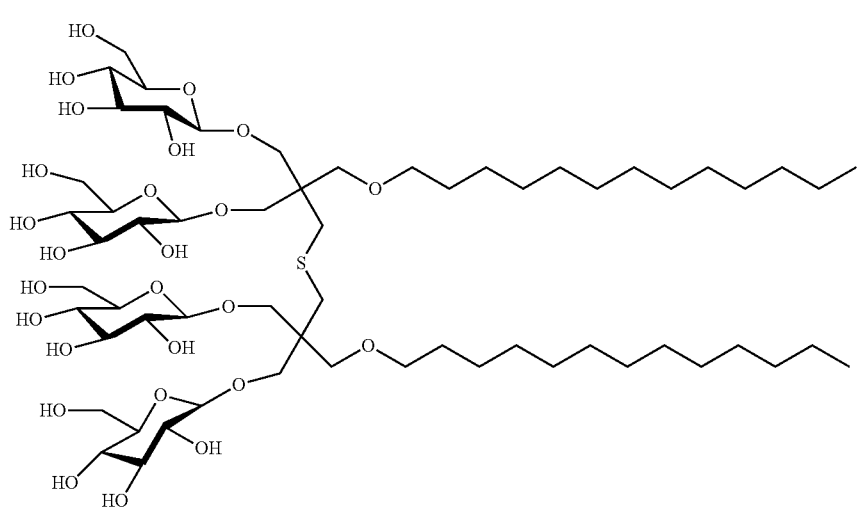

In one exemplary embodiment of the present invention, the compound represented by Formula 1 is any one of the compounds in which each of $R^1$ and $R^2$ is a $C_{12}$ alkyl group; each of $X^1$ to $X^4$ is glucose; each of $Y^1$ and $Y^2$ is O; and Z is S, and is named "TMG-T14." Therefore, the compound may be a compound represented by Formula 5 below:

[Formula 5]

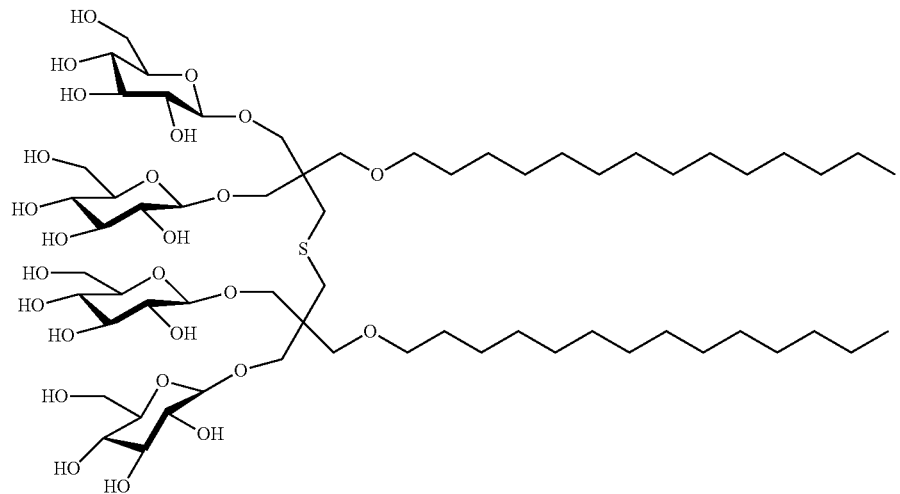

In one exemplary embodiment of the present invention, the compound represented by Formula 1 is any one of the compounds in which each of $R^1$ and $R^2$ is a $C_8$ alkyl group; each of $X^1$ to $X^4$ is glucose; each of $Y^1$ and $Y^2$ is $CH_2$; and Z is $CH_2$, and is named "TMG-A11." Therefore, the compound may be a compound represented by Formula 6 below:

[Formula 6]

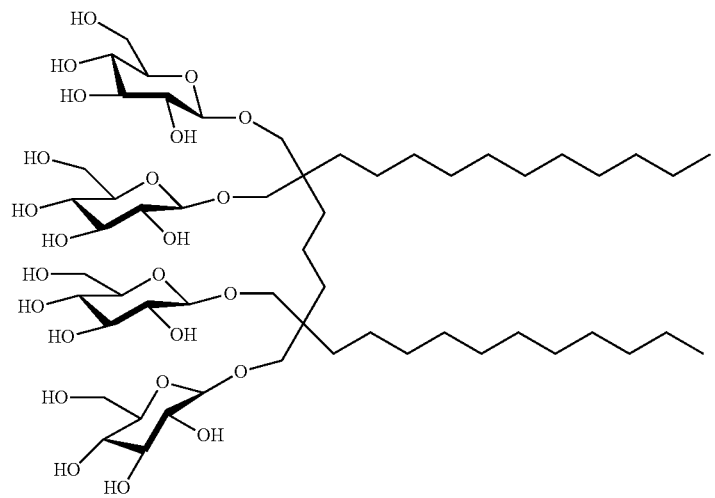

In one exemplary embodiment of the present invention, the compound represented by Formula 1 is any one of the compounds in which each of $R^1$ and $R^2$ is a $C_9$ alkyl group; each of $X^1$ to $X^4$ is glucose; each of $Y^1$ and $Y^2$ is $CH_2$; and Z is $CH_2$, and is named "TMG-A12." Therefore, the compound may be a compound represented by Formula 7 below:

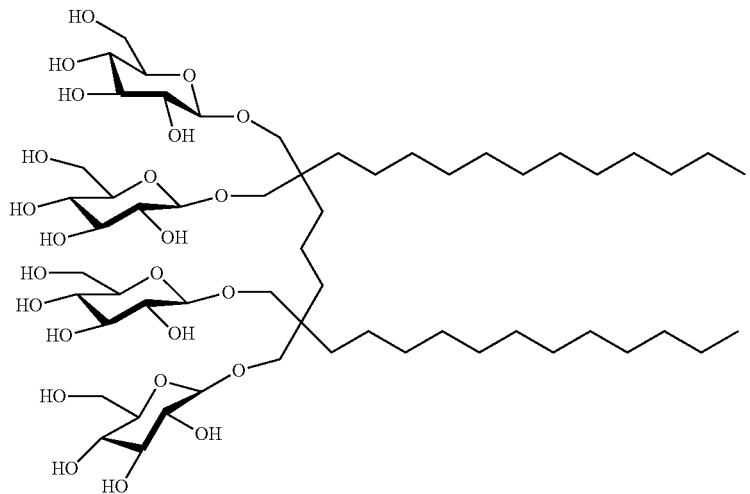

[Formula 7]

In one exemplary embodiment of the present invention, the compound represented by Formula 1 is any one of the compounds in which each of $R^1$ and $R^2$ is a $C_{10}$ alkyl group; each of $X^1$ to $X^4$ is glucose; each of $Y^1$ and $Y^2$ is $CH_2$; and Z is $CH_2$, and is named "TMG-A13." Therefore, the compound may be a compound represented by Formula 8 below:

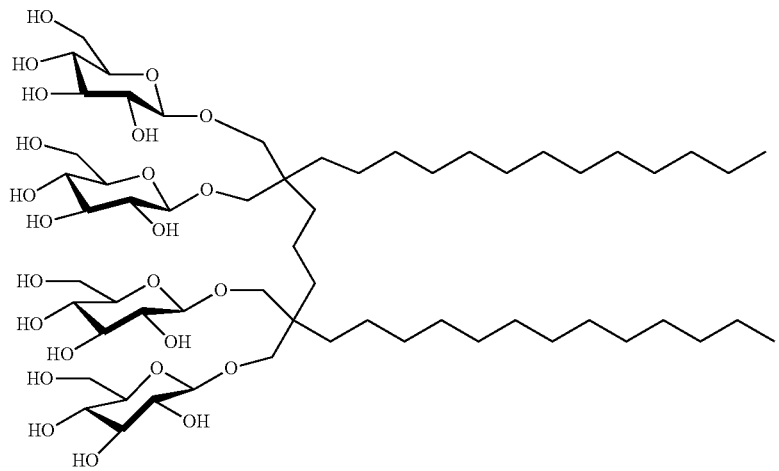

[Formula 8]

In one exemplary embodiment of the present invention, the compound represented by Formula 1 is any one of the compounds in which each of $R^1$ and $R^2$ is a $C_{11}$ alkyl group; each of $X^1$ to $X^4$ is glucose; each of $Y^1$ and $Y^2$ is $CH_2$; and Z is $CH_2$, and is named "TMG-A14." Therefore, the compound may be a compound represented by Formula 9 below:

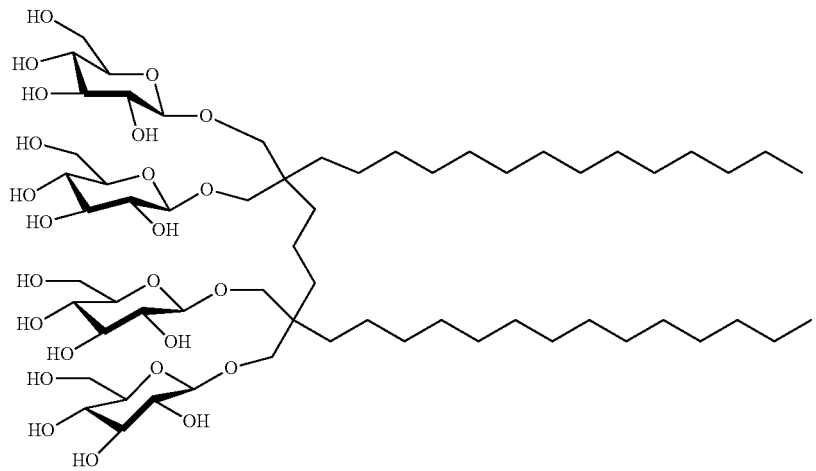

[Formula 9]

In one exemplary embodiment of the present invention, the compound represented by Formula 1 is any one of the compounds in which each of $R^1$ and $R^2$ is a substituted $C_{22}$ alkyl group; each of $X^1$ to $X^4$ is maltose; each of $Y^1$ and $Y^2$ is O; and Z is S, and is named "TMM-C22." Therefore, the compound may be a compound represented by Formula 10 below:

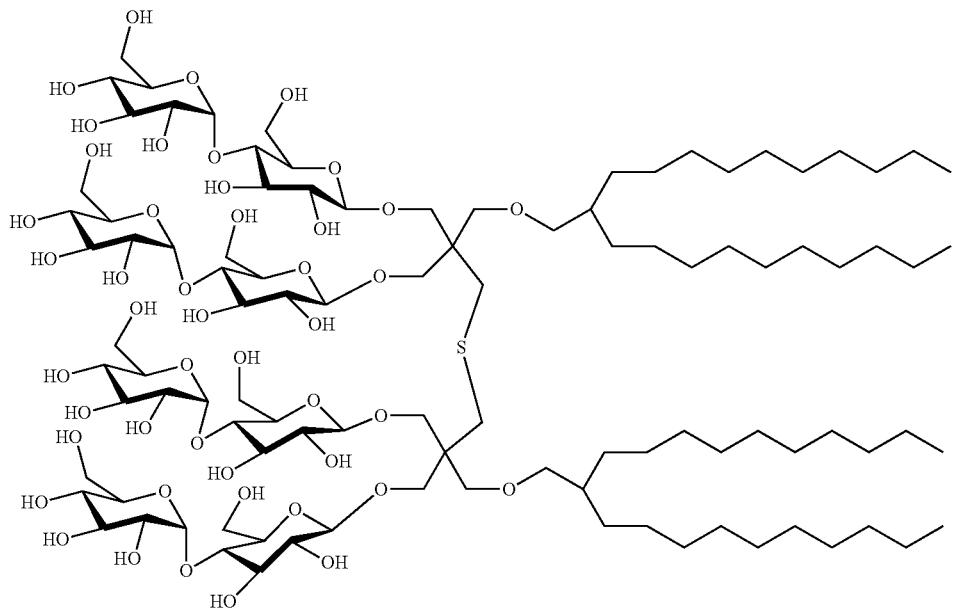

[Formula 10]

In one exemplary embodiment of the present invention, the compound represented by Formula 1 is any one of the compounds in which each of $R^1$ and $R^2$ is a substituted $C_{24}$ alkyl group; each of $X^1$ to $X^4$ is maltose; each of $Y^1$ and $Y^2$ is O; and Z is S, and is named "TMM-C24." Therefore, the compound may be a compound represented by Formula 11 below:

[Formula 11]

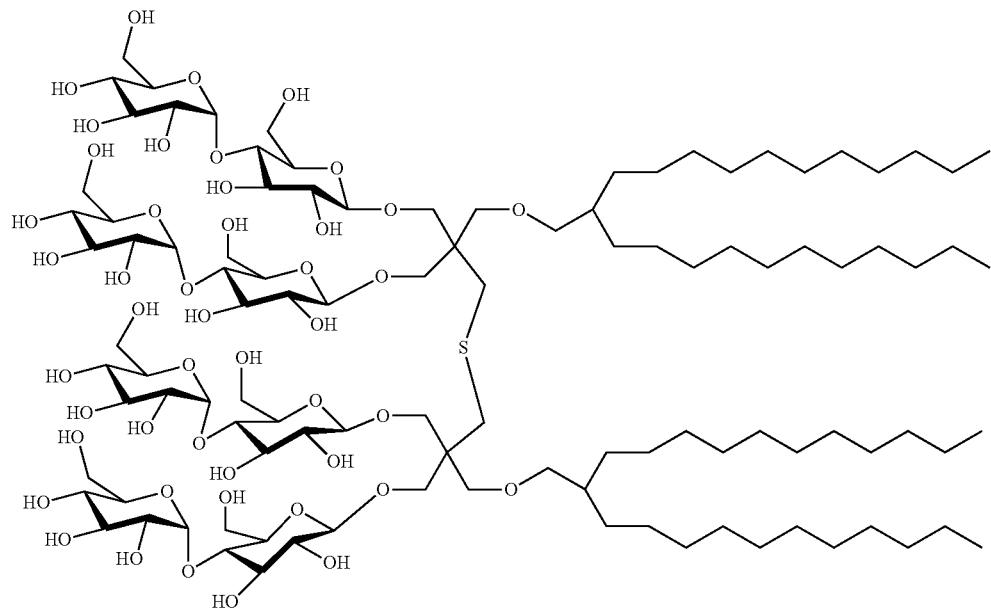

In one exemplary embodiment of the present invention, the compound represented by Formula 1 is any one of the compounds in which each of $R^1$ and $R^2$ is a substituted $C_{26}$ alkyl group; each of $X^1$ to $X^4$ is maltose; each of $Y^1$ and $Y^2$ is O; and Z is S, and is named "TMM-C26." Therefore, the compound may be a compound represented by Formula 12 below:

[Formula 12]

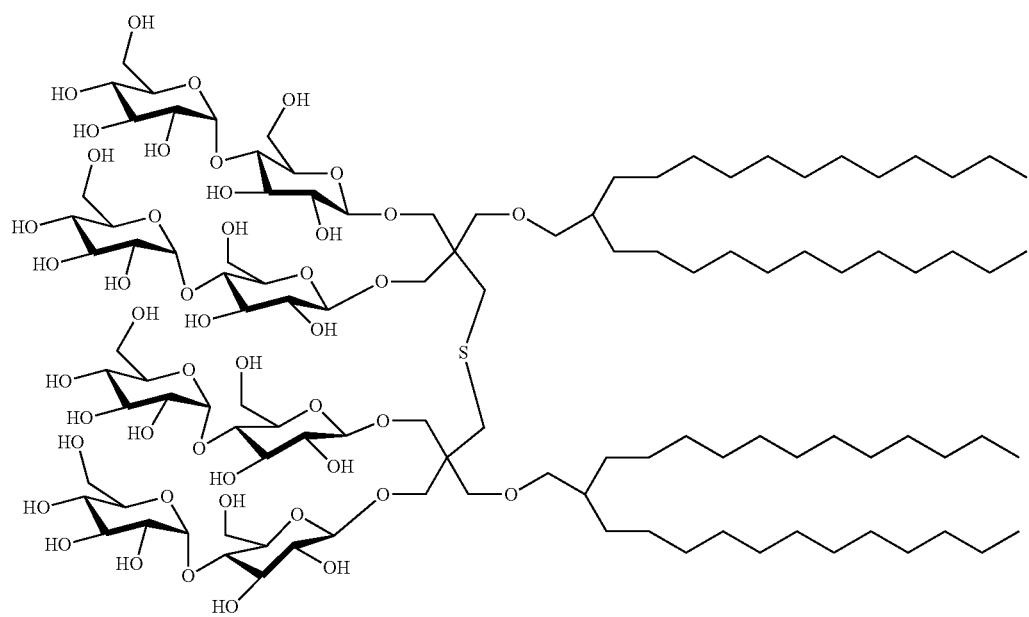

In one exemplary embodiment of the present invention, the compound represented by Formula 1 is any one of the compounds in which each of $R^1$ and $R^2$ is cholesterol; each of $X^1$ to $X^4$ is maltose; each of $Y^1$ and $Y^2$ is O; and Z is S, and is named "TMM-A27." Therefore, the compound may be a compound represented by Formula 13 below:

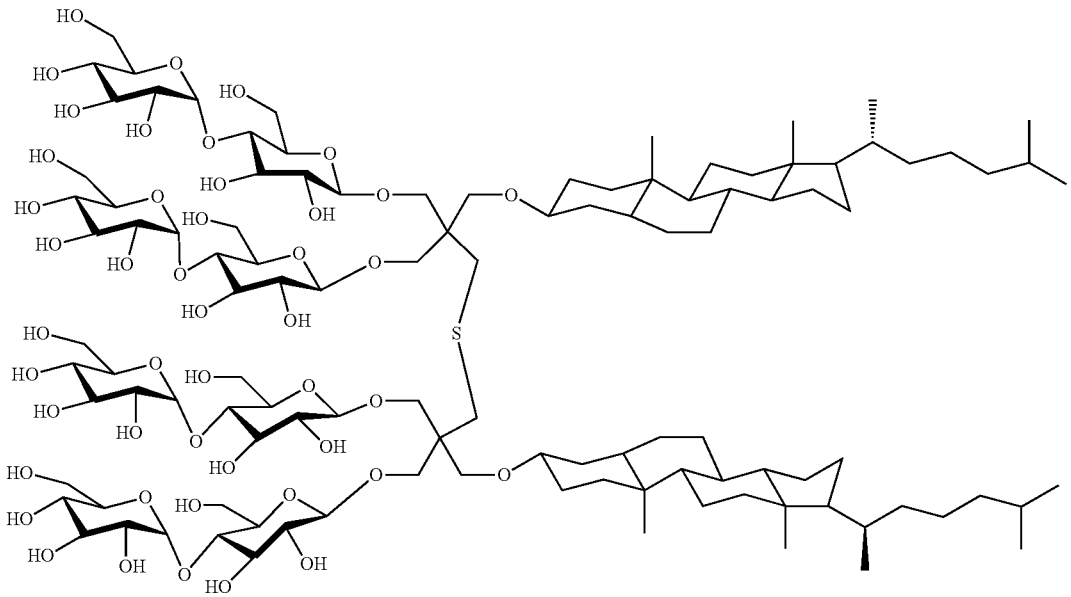

[Formula 13]

In one exemplary embodiment of the present invention, the compound represented by Formula 1 is any one of the compounds in which each of $R^1$ and $R^2$ is cholestanol; each of $X^1$ to $X^4$ is maltose; each of $Y^1$ and $Y^2$ is O; and Z is S, and is named "TMM-E27." Therefore, the compound may be a compound represented by Formula 14 below:

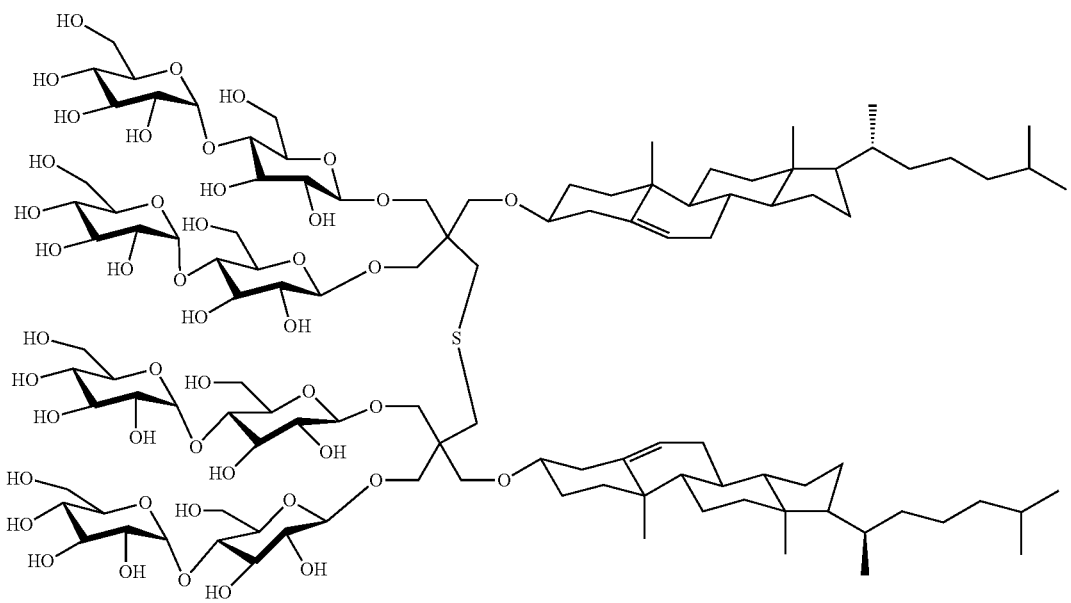

[Formula 14]

In one exemplary embodiment of the present invention, the compound represented by Formula 1 is any one of the compounds in which each of $R^1$ and $R^2$ is diosgenin; each of $X^1$ to $X^4$ is maltose; each of $Y^1$ and $Y^2$ is O; and Z is S, and is named "TMM-D27." Therefore, the compound may be a compound represented by Formula 15 below:

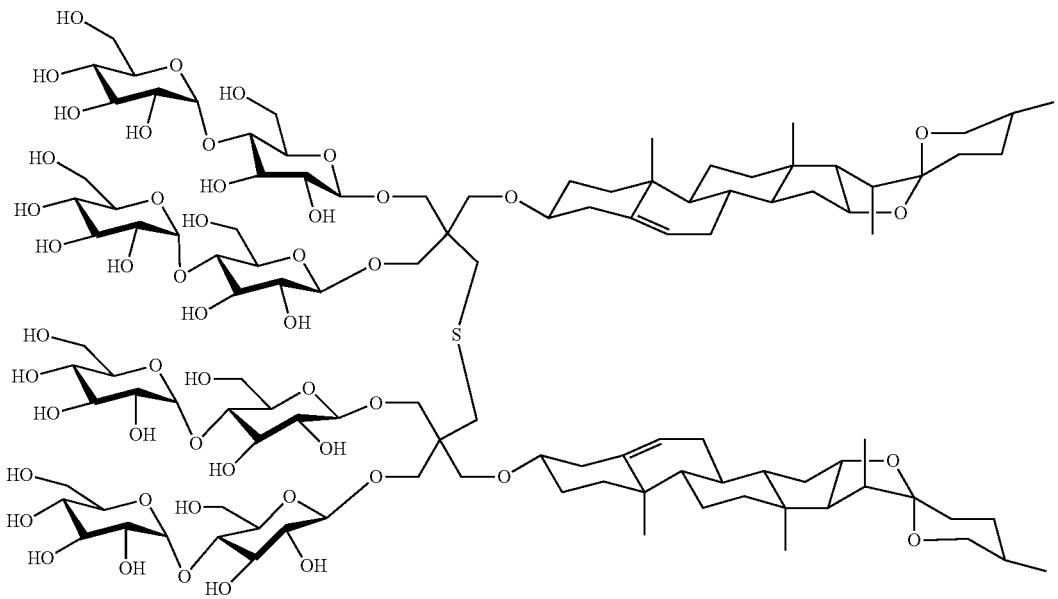

[Formula 15]

A compound according to another exemplary embodiment of the present invention may be an amphipathic molecule for extracting, solubilizing, stabilizing, crystallizing or analyzing membrane proteins, but the present invention is not limited thereto.

Specifically, the extraction may include extracting membrane proteins from a cell membrane.

The term "amphipathic molecule" used herein refers to a molecule that has affinity to both of polar and non-polar solvents due to the coexistence of hydrophobic groups and hydrophilic groups in one molecule. An amphipathic molecule or a phospholipid molecule present in a cell membrane is a molecule that has a hydrophilic group at one end and a hydrophobic group at the other end, thereby having amphipathicity, and forms micelles or liposomes in an aqueous solution. Although a hydrophilic group has polarity, due to the coexistence of the non-polar group, such an amphipathic molecule tends not to be well soluble in an aqueous solution. However, when a concentration is equal to or greater than a certain critical micelle concentration (CMC), a round or oval-shaped micelle in which hydrophobic groups aggregate inside due to hydrophobic interactions and hydrophilic groups are exposed at its surface is produced, and therefore solubility in water is greatly increased.

A method of measuring CMC is not particularly limited, and any method well known in the art, for example, a fluorescent staining method using diphenylhexatriene (DPH) may be used.

The compound according to an exemplary embodiment of the present invention may have a CMC in an aqueous solution of 0.0001 to 1 mM, specifically 0.0001 to 0.1 mM, more specifically 0.001 to 0.1 mM, and further more specifically 0.001 to 0.05 mM.

While DDM, which has been generally used in conventional research on membrane proteins, has a CMC of 0.17 mM, TMGs of the exemplary embodiment have very small CMC values. Therefore, since TMGs easily form micelles at a low concentration, membrane proteins may be effectively studied and analyzed with a small amount of TMGs, and may be advantageous in terms of utilization, compared to DDM.

In addition, in still another exemplary embodiment of the present invention, a composition for extracting, solubilizing, stabilizing, crystallizing or analyzing membrane proteins, which includes the compound, is provided.

Specifically, the extraction may include extracting membrane proteins from a cell membrane.

The composition may be prepared in the form of micelles, liposomes, an emulsion or nanoparticles, but the present invention is not limited thereto.

The micelles may have a radius of 2.0 to 20 nm, specifically 2.0 to 10.0 nm, and for example, 3.0 to 4.0 nm, but the present invention is not limited thereto.

A method of measuring the radius of the micelles is not particularly limited, and any method well known in the art, for example, a DLS test may be used.

The micelles, liposomes, emulsion or nanoparticles may be bound with the membrane proteins due to internal hydrophobicity. That is, the micelles, liposomes, emulsion or nanoparticles may enclose extracted membrane proteins present in the cell membrane. Therefore, it is possible to extract the membrane proteins from the cell membranes, and solubilize, stabilize, crystallize or analyze the membrane proteins, using the micelles.

The composition may further include a buffer that can help in extracting, solubilizing, stabilizing, crystallizing or analyzing membrane proteins.

In addition, in yet another exemplary embodiment of the present invention, a method of preparing a compound represented by Formula 1 is provided, the method including steps 1) to 5) as follows:

1) synthesizing tetramethyl pentane-1,1,5,5-tetracarboxylate by linking two dimethyl malonate molecules with an alkyl chain;

2) introducing an alkyl chain by performing an alkylation reaction on two α-carbons present in the product of step 1);

3) reducing four methyl carboxylate groups of the product of step 2) to alcohols;

4) introducing a protecting group-attached saccharide by performing a glycosylation reaction on the product of step 3); and 5) performing a deprotection reaction on the product of step 4).

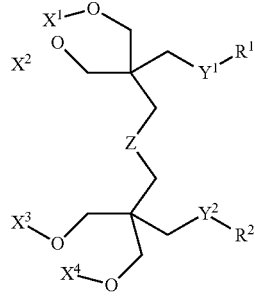

[Formula 1]

In Formula 1, $R^1$ and $R^2$ are each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;
each of $X^1$ to $X^4$ is a saccharide;
each of $Y^1$ and $Y^2$ is $CH_2$; and
Z is $CH_2$.

In yet another exemplary embodiment, a method of preparing a compound represented by Formula 1 is provided, the method including steps 1) to 3) as follows:
1) synthesizing thioether-containing tetraol by adding 5,5-bis-bromomethyl-2,2-dimethyl-[1,3]dioxane to a solution of 1-alkanol, dialkylated mono-ol, cholesterol, cholestanol or diosgenin;
2) introducing a protecting group-attached saccharide by performing a glycosylation reaction on the product of step 1); and
3) performing a deprotection reaction on the product of step 2).

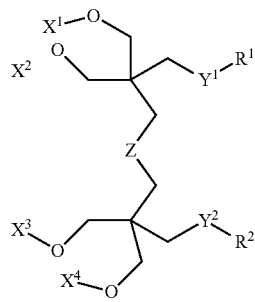

[Formula 1]

In Formula 1, $R^1$ and $R^2$ may be each independently a substituted or unsubstituted $C_3$-$C_{30}$ alkyl group, a substituted or unsubstituted $C_3$-$C_{30}$ cycloalkyl group, a substituted or unsubstituted $C_3$-$C_{30}$ aryl group or an organic group having a steroid backbone;
each of $X^1$ to $X^4$ may be a saccharide;
each of $Y^1$ and $Y^2$ may be O or S; and
Z may be S.

In the method of preparing the compound represented by Formula 1, $R^1$ and $R^2$ may be each independently a substituted or unsubstituted $C_3$-$C_{30}$ alkyl group or an organic group having a steroid backbone; and each of $X^1$ to $X^4$ may be glucose or maltose.

The compound synthesized by the method may be one of the compounds of Formulas 2 to 15 according to an exemplary embodiment of the present invention, but the present invention is not limited thereto.

In an exemplary embodiment, since a compound may be synthesized by a simple method including 3 or 5 short steps of synthesis, it is possible to produce large quantities of compounds for research on membrane proteins.

In yet another exemplary embodiment of the present invention, a method of extracting, solubilizing, stabilizing, crystallizing or analyzing membrane proteins is provided. Specifically, provided is a method of extracting, solubilizing, stabilizing, crystallizing or analyzing membrane proteins, which includes treating membrane proteins with a compound represented by Formula 1 in an aqueous solution:

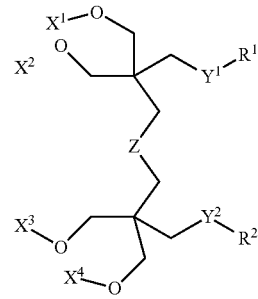

[Formula 1]

In Formula 1, $R^1$ and $R^2$ may be each independently a substituted or unsubstituted $C_3$-$C_{30}$ alkyl group, a substituted or unsubstituted $C_3$-$C_{30}$ cycloalkyl group, a substituted or unsubstituted $C_3$-$C_{30}$ aryl group or an organic group having a steroid backbone;
each of $X^1$ to $X^4$ may be a saccharide;
each of $Y^1$ and $Y^2$ may be $CH_2$, O or S; and
Z may be $CH_2$ or S.

Specifically, $R^1$ and $R^2$ may be each independently a substituted or unsubstituted $C_3$-$C_{30}$ alkyl group; each of $X^1$ to $X^4$ may be glucose or maltose; each of $Y^1$ and $Y^2$ may be $CH_2$; and Z may be $CH_2$.

In another exemplary embodiment, $R^1$ and $R^2$ may be each independently a substituted or unsubstituted $C_3$-$C_{30}$ alkyl group; $X^1$ to $X^4$ may be glucose or maltose; each of $Y^1$ and $Y^2$ may be O or S; and Z may be S.

In still another exemplary embodiment, $R^1$ and $R^2$ may be an organic group having a steroid backbone; each of $X^1$ to $X^4$ may be maltose; each of $Y^1$ and $Y^2$ may be O; and Z may be S.

The compound may be one of the compounds of Formulas 2 to 15 according to an exemplary embodiment of the present invention, but the present invention is not limited thereto.

Specifically, the extraction may include extracting membrane proteins from a cell membrane.

The term "membrane proteins" used herein encompass proteins or glycoproteins that are integrated into a cell membrane. They are present in various states, for example, passing through an entire cell membrane (transmembrane protein), located on a membrane surface (peripheral membrane protein), or attached to a cell membrane. Examples of the membrane proteins may include enzymes, receptors such as peptide hormones, local hormones, etc., receptor carriers such as a saccharide, ion channels, cell membrane antigens, but the present invention is not limited thereto.

The membrane proteins include any protein or glycoprotein that is integrated into a lipid bilayer of a cell membrane, and specifically a uric acid-xanthine/H⁺ symporter (UapA), a leucine transporter (LeuT), a human $\beta_2$ adrenergic receptor ($\beta_2$AR), melibiose permease (MelB$_{St}$), or a combination of two or more thereof, but the present invention is not limited thereto.

The term "extraction of membrane proteins" used herein means separation of membrane proteins from a cell membrane.

The term "solubilization of membrane proteins" used herein means solubilizing of water-insoluble membrane proteins in micelles in an aqueous solution.

The term "stabilization of membrane proteins" used herein means stable conservation of a tertiary or quaternary structure without changing the structures and functions of membrane proteins.

The term "crystallization of membrane proteins" used herein means the formation of crystals of membrane proteins in a solution.

The term "analysis of membrane proteins" used herein means analysis of the structures or functions of membrane proteins. In this exemplary embodiment, for the analysis of membrane proteins, a known method may be used without limitation, and for example, the structure of membrane proteins may be analyzed using electron microscopy or nuclear magnetic resonance.

In addition, a small glucoside group of the amphipathic molecule according to the present invention tends to form small membrane protein-amphipathic molecule complexes (protein-detergent complexes; PDCs). Since a large area of a hydrophilic protein surface is provided, a size of the small PDC is known to be advantageous for crystallization of membrane proteins. The formation of protein crystals is promoted by the interaction of hydrophilic domains of membrane proteins. The advantage of the small hydrophilic group of the amphipathic molecule is associated with a wide use of conventional glucoside amphipathic molecules (OG and NG) in the crystallization of membrane proteins. However, when a hydrophilic group of the amphipathic molecule is as small as glucose, it is disadvantageous for stabilizing membrane proteins, compared to an amphipathic molecule having a relatively large maltoside as a hydrophilic group. Therefore, for a large number of membrane proteins, a glucoside amphipathic molecule which has a superior stabilizing effect on membrane proteins, compared to DDM, has been rarely developed yet. However, although TMGs according to the present invention have glucose as a hydrophilic group, compared to DDM, they have a superior stabilizing effect with respect to all analyzed proteins, and therefore, it was confirmed that TMGs can be excellently used in stabilization of membrane proteins as well as crystallization thereof.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the accompanying drawings, in which.

(a) SDS-PAGE and western blotting results showing the amounts of $MelB_{St}$ proteins extracted using amphipathic molecules; and (b) a histogram showing $MelB_{St}$ proteins extracted using amphipathic molecules as the percentage (%) of a total amount of proteins present in a non-amphipathic molecule-treated membrane sample (Memb).

DESCRIPTION OF SPECIFIC EMBODIMENTS OF

THE INVENTION

Hereinafter, the present invention will be described in further detail in the following examples. However, the examples are provided to merely explain the present invention, but not to limit the scope of the present invention. It will be understood by those of ordinary skill in the art to which the present invention belongs that the scope of the present invention will include various changes that can be easily inferred from the detailed description and examples of the present invention.

<Example 1> Synthesis of TMG-As

Figure 1:
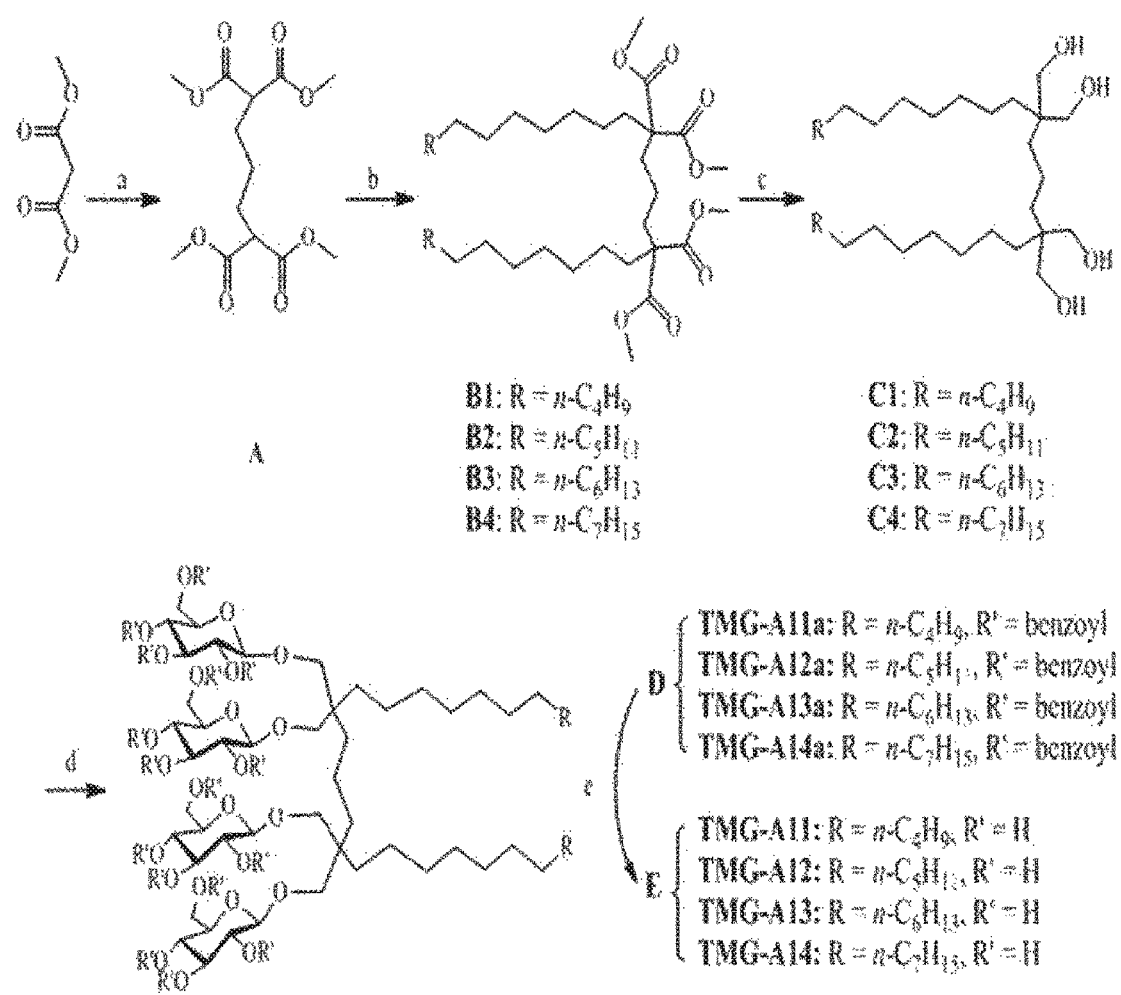
FIG. 1 is a diagram illustrating a synthesis scheme of TMG-As according to Example 1 of the present invention.

A synthesis scheme of TMG-As is shown in FIG. 1. Four types of TMG-A compounds were synthesized according to synthesis methods in Examples 1-1 to 1-5 below.

<1-1> General Synthesis Procedure for tetramethyl pentane-1,1,5,5-tetracarboxylate (Step a of FIG. 1)

Dimethylmalonate (16.9 mmol, 2.5 equivalents) was added to a solution prepared by stirring $K_2CO_3$ (2.34 g, 16.9 mmol, 2.5 equivalents) and 1,3-diiodopropane (6.76 mmol, 1 equivalent) in anhydrous DMF (20 mL). After stirring for 24 hours at room temperature, a reaction vessel was transferred to an oil container preheated to 100° C., and then the resulting solution was further stirred for 4 hours. After the reaction was completed (monitored by TLC), the reaction mixture was diluted with ether (100 mL), washed with water (2×100 mL) and brine (100 mL), and dried with anhydrous $Na_2SO_4$. Following the removal of the solvent, the remaining substance was purified by silica gel column chromatography (EtOAc/hexane), thereby obtaining solid-state colorless oil (compound A).

<1-2> General Alkylation Procedure for tetramethyl pentane-1,1,5,5-tetracarboxylate (Step b of FIG. 1)

Tetramethyl pentane-1,1,5,5-tetracarboxylate (6.57 mmol, 1 equivalent) was added to a suspension prepared by stirring NaH (15.8 mmol, 2.4 equivalents) in dry DMF (25 mL). Following 15-minute stirring, 1-iodoalkane (15.8 mmol, 2.4 equivalents) was added, and then the resulting mixture was stirred overnight at room temperature, and stirred for 5 hours at 50° C. After the completion of the reaction (monitored by TLC), ice-cold saturated $NH_4Cl$ was added to quench the reaction and extract diethylether (150 mL). The organic layer was washed with water (2×100 mL) and brine (100 mL), and dried with anhydrous $Na_2SO_4$. The solvent was completely evaporated, a remaining substance was purified by silica gel column chromatography (EtOAc/hexane), thereby obtaining an oily liquid, dialkylated tetramethyl pentane-1,1,5,5-tetracarboxylate (compound B).

<1-3> General Reduction Procedure for Alkylated tetramethyl pentane-1,1,5,5-tetracarboxylate (Step c of FIG. 1)

Dialkylated tetramethyl pentane-1,1,5,5-tetracarboxylate (compound B; 3.12 mmol, 1 equivalent) dissolved in THF (15 mL) was slowly added over 15 minutes to a suspension prepared by stirring $LiAlH_4$ (18.72 mmol, 6 equivalents) in anhydrous THF (20 mL) at 0° C. The mixture was stirred for 6 hours at room temperature. Following the completion of the reaction (monitored by TLC), the reaction was sequentially quenched with MeOH, water and a 1N HCl aqueous solution at 0° C. An organic layer was extracted with DCM (200 mL), washed with water (2×150 mL) and brine (100 mL), and dried with anhydrous $Na_2SO_4$. After the organic solvent was evaporated, the reaction mixture was purified by silica gel column chromatography (EtOAc/hexane), thereby obtaining a white solid, dialkyl-containing tetraol (compound C).

<1-4> General Synthesis Procedure for Glycosylation Reaction (Step d of FIG. 1)

AgOTf (5 equivalents) was added to a solution prepared by stirring Compound C and 2,4,6-collidine (3.0 equivalents) in $CH_2Cl_2$ (15 mL) at 0° C. and stirred for 10 minutes. A $CH_2Cl_2$ (10 mL) solution containing 5 equivalents of perbenzoylated glucosylbromide was slowly added to the mixture. The reaction was carried out with stirring for 30 minutes at 0° C. Following the completion of the reaction, pyridine was added to the reaction mixture, and the mixture was diluted with $CH_2Cl_2$ (20 mL) before being filtered with Celite. A filtrate was sequentially washed with a 1M $Na_2S_2O_3$ aqueous solution (40 mL), a 0.1 M HCl aqueous solution (40 mL) and brine (3×40 mL). The organic layer was dried with anhydrous $Na_2SO_4$, and the solvent was removed using a rotary evaporator. A remaining substance was purified by silica gel column chromatography (EtOAc/hexane), thereby obtaining a glassy solid, Compound D.

<1-5> General Synthesis Procedure for Deprotection Reaction (Step e of FIG. 1)

In this method, de-O-benzoylation was performed under Zemplen's conditions (Ashton, P. R.; Boyd, S. E.; Brown, C. L.; Jayaraman, N.; Nepogodiev, S. A.; Stoddart, J. F. Chem.-Eur. J. 1996, 2, 1115-1128). O-protected Compound D was dissolved with anhydrous $CH_2Cl_2$, and then MeOH was slowly added until precipitation. The reaction mixture was treated with a 0.5M methanolic solution, NaOMe, to have a final concentration of 0.05M. To prevent precipitation, the methanolic solution was added. The reaction mixture was stirred at room temperature for 6 hours. Following the completion of the reaction, the reaction mixture was neutralized using an Amberlite IR-120 ($H^+$ form) resin. The resin was removed by filtration and washed with MeOH, and then the solvent was removed from the filtrate in vacuo. A remaining substance was recrystallized using $CH_2Cl_2/$ MeOH/diethyl ether, thereby obtaining a white solid from which a protective group was completely removed, that is, Compound E.

<Preparation Example 1> Synthesis of TMG-A11

<1-1> Synthesis of Compound A (tetramethyl pentane-1,1,5,5-tetracarboxylate)

According to the general synthesis procedure for tetramethyl pentane-1,1,5,5-tetracarboxylate of Example 1-1, Compound A was synthesized with a yield of 93%: $^1$H NMR (400 MHz, CDCl$_3$): δ 3.73 (s, 12H), 3.36 (t, J=8.0 Hz, 2H), 1.96-1.90 (m, 4H), 1.39-1.33 (m, 2H); $^{13}$C NMR (100 MHz, CDCl$_3$): δ 170.0, 52.6, 51.4, 28.4, 25.1.

<1-2> Synthesis of Compound B1 (tetramethyl heptacosane-12,12,16,16-tetracarboxylate)

According to the general procedure for alkylation of tetramethyl pentane-1,1,5,5-tetracarboxylate of Example 1-2, Compound B1 was synthesized with a yield of 82%: $^1$H NMR (400 MHz, CDCl$_3$): δ 3.69 (s, 12H), 1.88-1.78 (m, 8H), 1.38-1.10 (m, 46H), 0.84 (t, J=7.1 Hz, 6H); $^{13}$C NMR (100 MHz, CDCl$_3$): δ 172.4, 57.7, 52.5, 34.3, 33.0, 32.9, 32.7, 32.1, 30.0, 29.8, 29.6, 29.0, 28.4, 24.3, 22.9, 19.1, 14.3.

<1-3> Synthesis of Compound C1 (2,6-bis(hydroxymethyl)-2,6-diundecylheptane-1,7-diol)

According to the general procedure for reduction of alkylated tetramethyl pentane-1,1,5,5-tetracarboxylate of Example 1-3, Compound C1 was synthesized with a yield of 83%: $^1$H NMR (400 MHz, CDCl$_3$): δ 3.54 (s, 8H), 1.68-1.25 (m, 46H), 0.88 (t, J=6.8 Hz, 6H); $^{13}$C NMR (100 MHz, CDCl$_3$): δ 32.1, 31.8, 30.8, 30.0, 29.8, 29.6, 27.0, 22.9, 19.1, 14.3.

<1-4> Synthesis of TMG-A11a

According to the general synthesis procedure for glycosylation reaction of Example 1-4, TMG-A11a was synthesized with a yield of 54%: $^1$H NMR (400 MHz, CDCl$_3$): δ 8.23-8.19 (m, 2H), 8.10-8.02 (m, 4H), 8.01-7.85 (m, 16H), 7.84-7.76 (m, 8H), 7.53-7.39 (m, 10H), 7.38-7.28 (m, 10H), 7.27-7.18 (m, 16H), 7.17-7.10 (m, 8H), 7.09-7.05 (m, 6H), 5.72-5.57 (m, 6H), 5.56-5.52 (m, 2H), 4.62-4.42 (m, 6H), 3.81-3.76 (m, 2H), 3.49-3.43 (m, 2H), 3.19-3.01 (m, 2H), 2.96-2.93 (m, 2H), 1.45-0.91 (m, 46H), 0.88 (t, J=6.7 Hz, 6H); $^{13}$C NMR (100 MHz, CDCl$_3$): δ 166.1, 166.0, 165.9, 165.8, 165.2, 164.8, 164.7, 133.7, 133.5, 133.3, 133.0, 130.2, 130.1, 129.9, 129.8, 129.7, 129.4, 129.1, 129.0, 128.8, 128.7, 128.6, 128.5, 128.4, 128.1, 128.0, 101.9, 101.6, 101.5, 72.9, 72.7, 72.5, 72.0, 71.7, 71.3, 70.0, 69.7, 69.5, 69.3, 62.9, 60.5, 40.6, 32.1, 31.0, 30.9, 30.7, 30.4, 30.0, 29.6, 22.8, 22.5, 14.3.

<1-5> Synthesis of TMG-A11

According to the general synthesis procedure for deprotection reaction of Example 1-5, TMG-A11 was synthesized with a yield of 95%: $^1$H NMR (400 MHz, CD$_3$OD): δ 4.34 (d, J=4.0 Hz, 4H), 3.92-3.85 (m, 4H), 3.75-3.63 (m, 8H), 3.48-3.35 (m, 4H), 3.25-3.19 (m, 4H), 1.33-1.22 (m, 46H), 0.88 (t, J=7.2 Hz, 6H); $^{13}$C NMR (100 MHz, CD$_3$OD): δ 105.0, 78.2, 77.8, 75.3, 75.2, 73.3, 71.7, 62.9, 42.3, 33.2, 32.6, 32.0, 31.9, 31.2, 31.1, 31.0, 30.7, 23.9, 14.6; HRMS (EI): calcd. for C$_{55}$H$_{104}$O$_{24}$[M+Na]$^+$1149.4130, found 1149.9616.

<Preparation Example 2> Synthesis of TMG-A12

<2-1> Synthesis of Compound A (tetramethyl pentane-1,1,5,5-tetracarboxylate)

According to the general synthesis procedure for tetramethyl pentane-1,1,5,5-tetracarboxylate of Example 1-1, Compound A was synthesized with a yield of 93%: $^1$H NMR (400 MHz, CDCl$_3$): δ 3.73 (s, 12H), 3.36 (t, J=8.0 Hz, 2H), 1.96-1.90 (m, 4H), 1.39-1.33 (m, 2H); $^{13}$C NMR (100 MHz, CDCl$_3$): δ 170.0, 52.6, 51.4, 28.4, 25.1.

<2-2> Synthesis of Compound B2 (tetramethyl nonacosane-13,13,17,17-tetracarboxylate)

According to the general procedure for alkylation of tetramethyl pentane-1,1,5,5-tetracarboxylate of Example 1-2, Compound B2 was synthesized with a yield of 83%: $^1$H NMR (400 MHz, CDCl$_3$): δ 3.70 (s, 12H), 1.89-1.80 (m, 8H), 1.28-1.10 (m, 50H), 0.88 (t, J=7.1 Hz, 6H); $^{13}$C NMR (100 MHz, CDCl$_3$): δ 172.3, 57.7, 52.5, 32.9, 32.7, 32.1, 30.7, 30.0, 29.9, 29.8, 29.6, 28.8, 24.3, 22.9, 19.1, 14.3.

<2-3> Synthesis of Compound C2 (2,6-didodecyl-2,6-bis(hydroxymethyl)heptane-1,7-diol)

According to the general procedure for reduction of alkylated tetramethyl pentane-1,1,5,5-tetracarboxylate of Example 1-3, Compound C2 was synthesized with a yield of 83%: $^1$H NMR (400 MHz, CDCl$_3$): δ 3.49 (s, 8H), 1.66-1.24 (m, 50H), 0.88 (t, J=6.8 Hz, 6H); $^{13}$C NMR (100 MHz, CDCl$_3$): δ 32.2, 31.9, 30.8, 30.0, 29.9, 29.6, 27.2, 23.0, 22.9, 14.4.

<2-4> Synthesis of TMG-A12a

According to the general synthesis procedure for glycosylation reaction of Example 1-4, TMG-A12a was synthesized with a yield of 53%: $^1$H NMR (400 MHz, CDCl$_3$): δ 8.18-8.16 (m, 2H), 8.02-7.94 (m, 4H), 7.92-7.72 (m, 16H), 7.71-7.56 (m, 8H), 7.54-7.48 (m, 10H), 7.43-7.37 (m, 10H), 7.29-7.24 (m, 16H), 7.21-7.10 (m, 8H), 5.66-5.41 (m, 8H), 4.48-4.34 (m, 6H), 3.79-3.74 (m, 2H), 3.51-3.45 (m, 2H), 2.94-2.90 (m, 2H), 1.27-1.15 (m, 50H), 0.86 (t, J=7.1 Hz, 6H); $^{13}$C NMR (100 MHz, CDCl$_3$): δ 166.0, 165.9, 165.8, 165.7, 165.4, 165.2, 164.8, 164.7, 164.2, 133.7, 133.5, 133.2, 133.0, 130.4, 130.2, 130.0, 129.8, 129.7, 129.6, 129.4, 129.1, 129.0, 128.8, 128.6, 128.5, 128.4, 128.3, 128.1, 128.0, 101.6, 101.5, 72.8, 72.6, 72.5, 72.0, 71.7, 71.4, 70.0, 69.7, 69.5, 69.3, 62.3, 40.6, 32.0, 30.9, 30.7, 30.4, 30.0, 29.9, 29.5, 22.8, 22.5, 14.3.

<2-5> Synthesis of TMG-A12

According to the general synthesis procedure for deprotection reaction of Example 1-5, TMG-A12 was synthesized with a yield of 95%: $^1$H NMR (400 MHz, CD$_3$OD): δ 4.32 (d, J=4.0 Hz, 4H), 3.88-3.83 (m, 4H), 3.75-3.65 (m, 8H), 3.48-3.35 (m, 4H), 3.24-3.17 (m, 4H), 1.39-1.15 (m, 50H), 0.88 (t, J=6.6 Hz, 6H); $^{13}$C NMR (100 MHz, CD$_3$OD): δ 105.1, 78.3, 78.1, 77.9, 75.4, 75.2, 73.3, 71.9, 62.9, 42.3, 33.3, 32.7, 32.1, 31.2, 31.1, 31.0, 30.7, 24.0, 16.9, 14.7; HRMS (EI): calcd. for $C_{57}H_{108}O_{24}[M+Na]^+$ 1177.4670, found 1177.7233.

<Preparation Example 3> Synthesis of TMG-A13

<3-1> Synthesis of Compound A (tetramethyl pentane-1,1,5,5-tetracarboxylate)

According to the general synthesis procedure for tetramethyl pentane-1,1,5,5-tetracarboxylate of Example 1-1, Compound A was synthesized with a yield of 93%: $^1$H NMR (400 MHz, CDCl$_3$): δ 3.73 (s, 12H), 3.36 (t, J=8.0 Hz, 2H), 1.96-1.90 (m, 4H), 1.39-1.33 (m, 2H); $^{13}$C NMR (100 MHz, CDCl$_3$): δ 170.0, 52.6, 51.4, 28.4, 25.1.

<3-2> Synthesis of Compound B3 (tetramethyl hentriacontane-14,14,18,18-tetracarboxylate)

According to the general procedure for alkylation of tetramethyl pentane-1,1,5,5-tetracarboxylate of Example 1-2, Compound B3 was synthesized with a yield of 85%: $^1$H NMR (400 MHz, CDCl$_3$): δ 3.68 (s, 12H), 1.87-1.80 (m, 8H), 1.38-1.32 (m, 2H), 1.28 (s, 54H), 1.25-1.10 (m, 6H), 0.87 (t, J=7.1 Hz, 6H); $^{13}$C NMR (100 MHz, CDCl$_3$): δ 172.4, 57.6, 52.5, 34.3, 33.1, 32.9, 32.7, 32.1, 30.0, 29.9, 29.7, 29.6, 29.0, 28.4, 24.3, 22.9, 19.1, 14.3.

<3-3> Synthesis of Compound C3 (2,6-bis(hydroxymethyl)-2,6-ditridecylheptane-1,7-diol)

According to the general procedure for reduction of alkylated tetramethyl pentane-1,1,5,5-tetracarboxylate of Example 1-3, Compound C3 was synthesized with a yield of 85%: $^1$H NMR (400 MHz, CDCl$_3$): δ 3.49 (s, 8H), 1.67-1.10 (m, 54H), 0.88 (t, J=6.8 Hz, 6H); $^{13}$C NMR (100 MHz, CDCl$_3$): δ 32.2, 31.8, 30.9, 30.1, 29.9, 29.6, 27.0, 26.6, 22.9, 14.3.

<3-4> Synthesis of TMG-A13a

According to the general synthesis procedure for glycosylation reaction of Example 1-4, TMG-A13a was synthesized with a yield of 53%: $^1$H NMR (400 MHz, CDCl$_3$): δ 8.23-8.19 (m, 2H), 8.01-7.95 (m, 4H), 7.93-7.85 (m, 16H), 7.73-7.70 (m, 8H), 7.54-7.48 (m, 6H), 7.47-7.42 (m, 10H), 7.41-7.35 (m, 16H), 7.34-7.23 (m, 8H), 7.21-7.17 (m, 6H), 5.65-5.59 (m, 8H), 5.52-5.24 (m, 2H), 4.46-4.33 (m, 6H), 3.81-3.73 (m, 2H), 3.51-3.46 (m, 2H), 3.10-3.07 (m, 2H), 2.93-2.88 (m, 2H), 1.48-0.93 (m, 54H), 0.86 (t, J=6.9 Hz, 6H); $^{13}$C NMR (100 MHz, CDCl$_3$): δ 166.1, 166.0, 165.9, 165.2, 165.1, 164.8, 164.7, 133.7, 133.5, 133.3, 133.2, 130.2, 130.0, 129.8, 129.7, 129.5, 129.3, 129.1, 129.0, 128.7, 128.6, 128.5, 128.4, 128.3, 128.1, 101.6, 101.5, 72.6, 72.0, 71.6, 71.4, 70.0, 69.7, 63.3, 62.9, 60.4, 53.6, 40.6, 32.0, 30.9, 30.7, 30.4, 30.0, 29.9, 29.8, 29.6, 22.8, 22.5, 14.3.

<3-5> Synthesis of TMG-A13

According to the general synthesis procedure for deprotection reaction of Example 1-5, TMG-A13 was synthesized with a yield of 96%: $^1$H NMR (400 MHz, CD$_3$OD): δ 4.32 (d, J=4.0 Hz, 4H), 3.88-3.82 (m, 4H), 3.75-3.63 (m, 8H), 3.48-3.35 (m, 4H), 3.22-3.18 (m, 4H), 1.34-1.12 (m, 54H), 0.90 (t, J=8.0 Hz, 6H); $^{13}$C NMR (100 MHz, CD$_3$OD): δ 105.1, 78.3, 77.9, 75.4, 75.2, 73.4, 71.8, 62.9, 42.4, 33.3, 32.7, 32.1, 32.0, 31.2, 31.1, 31.0, 24.0, 14.7; HRMS (EI): calcd. for $C_{59}H_{112}O_{24}[M+Na]^+$ 1205.5210, found 1205.754.

<Preparation Example 4> Synthesis of TMG-A14

<4-1> Synthesis of Compound A (tetramethyl pentane-1,1,5,5-tetracarboxylate)

According to the general synthesis procedure for tetramethyl pentane-1,1,5,5-tetracarboxylate of Example 1-1, Compound A was synthesized with a yield of 93%: $^1$H NMR (400 MHz, CDCl$_3$): δ 3.73 (s, 12H), 3.36 (t, J=8.0 Hz, 2H), 1.96-1.90 (m, 4H), 1.39-1.33 (m, 2H); $^{13}$C NMR (100 MHz, CDCl$_3$): δ 170.0, 52.6, 51.4, 28.4, 25.1.

<4-2> Synthesis of Compound B4 (tetramethyl tritriacontane-15,15,19,19-tetracarboxylate)

According to the general procedure for alkylation of tetramethyl pentane-1,1,5,5-tetracarboxylate of Example 1-2, Compound B4 was synthesized with a yield of 87%: $^1$H NMR (400 MHz, CDCl$_3$): δ 3.69 (s, 12H), 1.89-1.80 (m, 8H), 1.26-1.05 (m, 58H), 0.87 (t, J=7.1 Hz, 6H); $^{13}$C NMR (100 MHz, CDCl$_3$): δ 172.4, 57.7, 52.5, 32.9, 32.8, 32.1, 30.0, 29.9, 29.8, 29.6, 24.3, 22.9, 19.1, 14.3.

<4-3> Synthesis of Compound C4 (2,6-bis(hydroxymethyl)-2,6-ditetradecylheptane-1,7-diol)

According to the general procedure for reduction of alkylated tetramethyl pentane-1,1,5,5-tetracarboxylate of Example 1-3, Compound C4 was synthesized with a yield of 86%: $^1$H NMR (400 MHz, CDCl$_3$): δ 3.55 (s, 8H), 1.67-1.16 (m, 58H), 0.88 (t, J=6.8 Hz, 6H); $^{13}$C NMR (100 MHz, CDCl$_3$): δ 32.2, 31.9, 31.1, 30.1, 29.9, 29.6, 27.1, 26.7, 22.9, 14.3.

<4-4> Synthesis of TMG-A14a

According to the general synthesis procedure for glycosylation reaction of Example 1-4, TMG-A14a was synthesized with a yield of 52%: $^1$H NMR (400 MHz, CDCl$_3$): δ 8.24-8.20 (m, 2H), 8.02-7.96 (m, 4H), 7.95-7.89 (m, 16H), 7.75-7.71 (m, 8H), 7.54-7.48 (m, 6H), 7.47-7.41 (m, 10H), 7.39-7.35 (m, 16H), 7.34-7.23 (m, 8H), 7.21-7.17 (m, 6H), 5.65-5.60 (m, 8H), 5.54-5.43 (m, 2H), 4.46-4.33 (m, 6H), 3.82-3.73 (m, 2H), 3.53-3.47 (m, 2H), 3.14-3.09 (m, 2H), 2.95-2.86 (m, 2H), 1.49-0.94 (m, 58H), 0.86 (t, J=7.1 Hz, 6H); $^{13}$C NMR (100 MHz, CDCl$_3$): δ 166.1, 166.0, 165.9, 165.2, 165.1, 164.8, 164.7, 133.7, 133.5, 133.3, 133.2, 130.2, 130.0, 129.8, 129.7, 129.5, 129.3, 129.1, 129.0, 128.7, 128.6, 128.5, 128.4, 128.3, 128.1, 101.6, 101.5, 72.6, 72.0, 71.6, 71.4, 70.0, 69.7, 69.2, 63.3, 63.0, 62.6, 60.4, 53.6, 40.6, 32.0, 30.9, 30.7, 30.4, 30.0, 29.9, 29.8, 29.5, 22.8, 22.5, 21.1, 14.9, 14.3.

<4-5> Synthesis of TMG-A14

According to the general synthesis procedure for deprotection reaction of Example 1-5, TMG-A14 was synthesized with a yield of 96%: $^1$H NMR (400 MHz, CD$_3$OD): δ 4.34 (d, J=4.0 Hz, 4H), 3.88-3.84 (m, 4H), 3.75-3.65 (m, 8H), 3.48-3.35 (m, 4H), 3.22-3.18 (m, 4H), 1.31-1.12 (m, 58H), 0.90 (t, J=8.0 Hz, 6H); $^{13}$C NMR (100 MHz, CD$_3$OD): δ 105.1, 78.2, 77.8, 75.3, 75.2, 73.3, 71.8, 62.9, 42.4, 33.2, 32.6, 32.1, 31.9, 31.2, 31.1, 31.0, 30.7, 24.0, 14.7; HRMS (EI): calcd. for $C_{61}H_{116}O_{24}[M+Na]^+$ 1233.5750, found 1233.7858.

<Example 2> Synthesis of TMG-Ts

Figure 2:
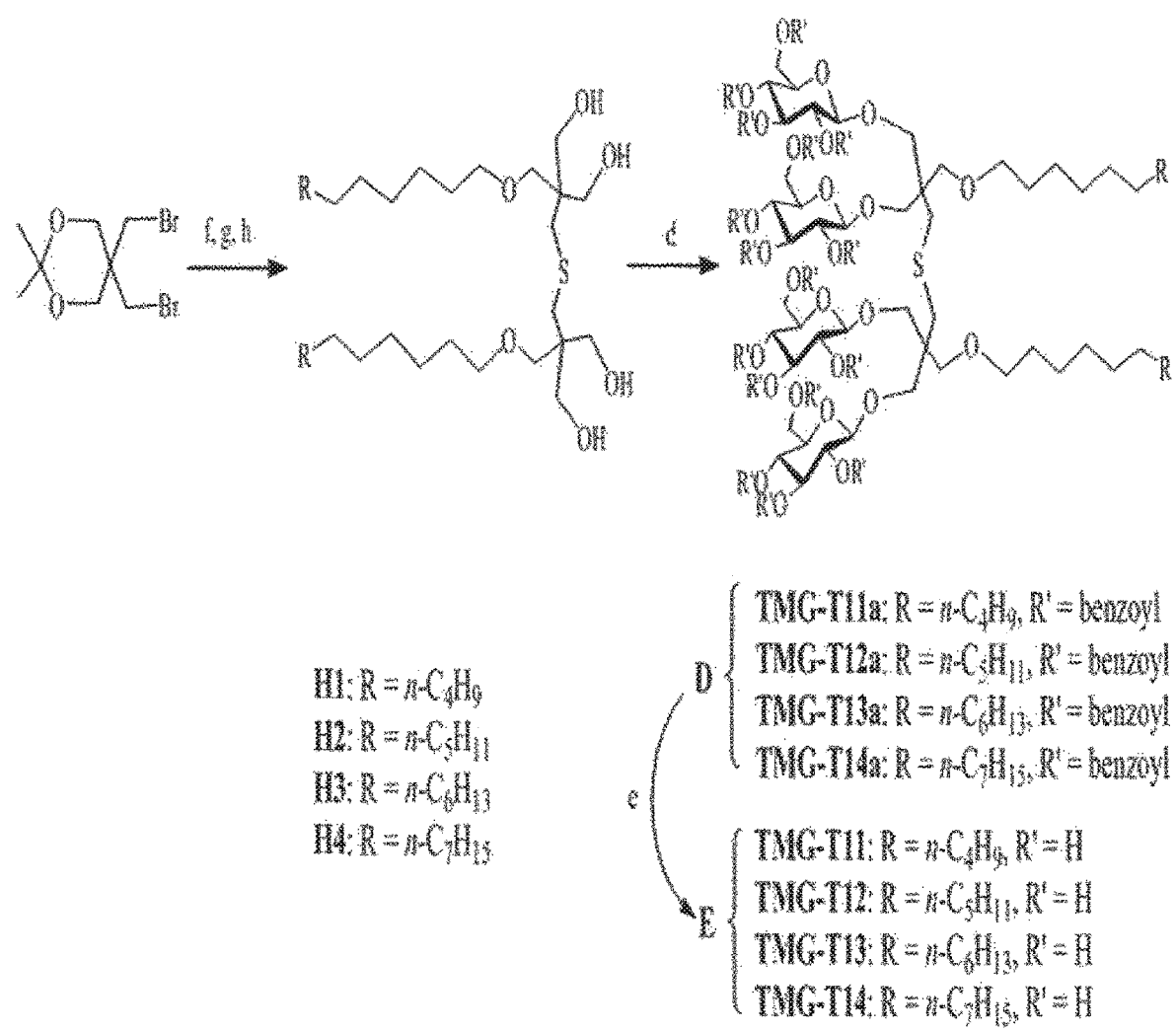
FIG. 2 is a diagram illustrating a synthesis scheme of TMG-Ts according to Example 2 of the present invention.

A synthesis scheme of TMG-Ts is shown in FIG. 2. Four types of TMG-T compounds were synthesized according to the synthesis methods in Examples 2-1 to 2-3 as follows.

<2-1> General Procedure for Synthesis of 2,2'-(thiobis(methylene))bis(2-(alkyloxy)methyl)propane-1,3-diol (Steps f-h of FIG. 2)

NaH (11.6 mmol, 1.2 equivalents, 60%) was added to a solution of a 1-alkanol (11.6 mmol, 1 equivalent) in anhydrous DMF (25 mL) at 0° C. The mixture was stirred at room temperature for 30 minutes, and then 5,5-bis-bromomethyl-2,2-dimethyl-[1,3]dioxane (11.6 mmol, 1 equivalent) was added. A reaction vessel was transferred to an oil container preheated to 100° C., and further stirring was carried out for 15 hours. After the completion of the reaction (monitored by TLC), a reaction mixture was cooled at room temperature, rapidly cooled with ice-cold $H_2O$ (50 mL), and extracted with ether (3×100 mL). A mixed organic layer was washed with brine (2×150 mL), dried with anhydrous $Na_2SO_4$, and concentrated using a rotary evaporator. A product (5.08 mmol, 1 equivalent) was dissolved in DMF (20 mL), and KI (5.08 mmol, 1 equivalent) was added to the solution. Following the addition of $Na_2S$. $9H_2O$ (0.6 equivalents) in water (5 mL) to the mixture, DMF (20 mL) was further added, and the mixture was stirred for 20 hours at 90° C. under nitrogen ($N_2$). After cooling, the mixture was poured into water (300 mL) and extracted with ether (150 mL). The extract was sequentially washed with water (300 mL), a 2.5% NaOH solution (300 mL) and brine (100 mL), and dried with anhydrous $Na_2SO_4$. The reaction mixture was stirred with 3 g of silica gel, filtered, and concentrated by rotary evaporation. The concentrated reaction mixture was dissolved in a 1:1 mixture of $CH_2Cl_2$ and MeOH (50 mL), p-toluenesulfonic acid (p-TSA) monohydrate (200 mg) was added, and then the resulting mixture was stirred for 6 hours at room temperature. Following the completion of the mixture, the reaction mixture was neutralized with a $NaHCO_3$ solution, filtered, and dried by rotary evaporation. By flash column chromatography (EtOAc/hexane), a white solid, thioether-containing tetraol (Compound H) was obtained.

<2-2> General Synthesis Procedure for Glycosylation Reaction (Step d of FIG. 2)

AgOTf (5 equivalents) was added to a solution prepared by stirring Compound H and 2,4,6-collidine (3.0 equivalents) in $CH_2Cl_2$ (15 mL) at 0° C., and stirred for 10 minutes. A $CH_2Cl_2$ (10 mL) solution containing 5 equivalents of perbenzoylated glucosylbromide was slowly added to the mixture. The reaction was carried out with stirring for 30 minutes at 0° C. After the reaction, pyridine was added to the reaction mixture, and the mixture was diluted with $CH_2Cl_2$ (20 mL), before being filtered with Celite. The filtrate was sequentially washed with a 1M $Na_2S_2O_3$ aqueous solution (40 mL), a 0.1 M HCl aqueous solution (40 mL) and brine (3×40 mL). The organic layer was dried with anhydrous $Na_2SO_4$, and the solvent was removed using a rotary evaporator. A remaining substance was purified by silica gel column chromatography (EtOAc/hexane), thereby obtaining a glassy solid, Compound D.

<2-3> General Synthesis Procedure for Deprotection Reaction (Step e of FIG. 2)

In this method, de-O-benzoylation was performed under Zemplen's conditions (Ashton, P. R.; Boyd, S. E.; Brown, C. L.; Jayaraman, N.; Nepogodiev, S. A.; Stoddart, J. F. Chem.-Eur. J. 1996, 2, 1115-1128). O-protected Compound D was dissolved in a small amount of anhydrous $CH_2Cl_2$, and MeOH was slowly added until precipitation. The reaction mixture was treated with a 0.5M methanolic solution, NaOMe, to have a final concentration of 0.05M. To prevent precipitation, a methanolic solution was slowly added. The reaction mixture was stirred for 6 hours at room temperature. After the reaction, the reaction mixture was neutralized using an Amberlite IR-120 ($H^+$ form) resin. The resin was removed by filtration and washed with MeOH, and then the solvent was removed from the filtrate in vacuo. A remaining substance was recrystallized using $CH_2Cl_2$/MeOH/diethyl ether, thereby obtaining a white solid from which a protective group was completely removed, which was Compound E.

<Preparation Example 5> Synthesis of TMG-T11

<5-1> Synthesis of Compound H1 (2,2'-(thiobis(methylene))bis(2-((undecyloxy)methyl)propane-1,3-diol))

According to the general procedure for synthesis of 2,2'-(thiobis(methylene))bis(2-(alkyloxy)methyl)propane-1,3-diol of Example 2-1, Compound H1 was synthesized with a yield of 60%: $^1$H NMR (400 MHz, $CDCl_3$): δ 3.65 (s, 4H), 3.51-3.31 (m, 8H), 3.30 (s, 8H), 1.58-1.49 (m, 4H), 1.29 (s, 32H), 0.89 (t, J=6.8 Hz, 6H); $^{13}$C NMR (100 MHz, $CDCl_3$): δ 73.8, 73.3, 72.7, 66.1, 56.2, 49.8, 47.0, 45.4, 45.2, 35.6, 33.2, 30.9, 30.8, 30.6, 28.8, 27.5, 23.9, 21.5, 14.6.

<5-2> Synthesis of TMG-T11a

According to the general glycosylation procedure of Example 2-2, Compound TMG-T11a was synthesized with a yield of 52%: $^1$H NMR (400 MHz, $CDCl_3$): δ 8.35-8.31 (m, 2H), 8.16-8.14 (m, 4H), 7.99-7.91 (m, 16H), 7.90-7.78 (m, 8H), 7.72-7.63 (m, 10H), 7.52-7.44 (m, 10H), 7.42-7.32 (m, 16H), 7.31-7.23 (m, 12H), 6.91-6.78 (m, 2H), 5.82-5.78 (m, 6H), 5.77-5.52 (m, 4H), 4.61-4.39 (m, 8H), 3.92-3.72 (m, 4H), 3.53-3.42 (m, 4H), 3.41-3.12 (m, 8H), 1.49-1.32 (m, 4H), 1.31-0.97 (m, 32H), 0.86 (t, J=8.0 Hz, 6H); $^{13}$C NMR (100 MHz, $CDCl_3$): δ 166.1, 166.0, 165.8, 165.7, 165.4, 165.2, 165.0, 164.9, 164.7, 133.8, 133.7, 133.4, 133.2, 133.1, 130.5, 130.3, 130.0, 129.8, 129.7, 129.6, 129.4, 129.3, 129.2, 129.1, 129.0, 128.7, 128.6, 128.5, 128.4, 128.0, 72.7, 72.6, 72.5, 72.1, 71.8, 71.6, 71.5, 70.0, 69.9, 60.5, 45.2, 32.1, 29.9, 29.8, 29.7, 29.6, 26.2, 22.8, 14.3.

<5-3> Synthesis of TMG-T11

According to the general synthesis procedure for deprotection reaction of Example 2-3, TMG-T11 was synthesized with a yield of 94%: $^1$H NMR (400 MHz, $CD_3OD$): δ 4.37-4.31 (m, 4H), 3.95-3.83 (m, 8H), 3.78-3.62 (m, 4H), 3.61-3.51 (m, 4H), 3.49-3.35 (m, 12H), 3.31-3.19 (m, 4H), 1.61-1.49 (m, 4H), 1.41-1.20 (m, 32H), 0.90 (t, J=7.2 Hz, 6H); $^{13}$C NMR (100 MHz, $CD_3OD$): δ 105.0, 104.8, 78.0, 77.8, 75.2, 72.6, 71.6, 71.5, 71.4, 71.2, 70.7, 70.6, 63.0, 62.8, 46.4, 46.0, 33.2, 32.2, 31.0, 30.9, 30.8, 30.6, 27.5, 23.8, 14.6; HRMS (EI): calcd. for $C_{56}H_{106}O_{26}S$ [M+Na]$^+$ 1227.4980 found 1227.6697.

<Preparation Example 6> Synthesis of TMG-T12

<6-1> Synthesis of Compound H2 (2,2'-(thiobis (methylene))bis(2-((dodecyloxy)methyl)propane-1, 3-diol))

According to the general procedure for synthesis of 2,2'-(thiobis(methylene))bis(2-(alkyloxy)methyl)propane-1, 3-diol of Example 2-1, Compound H2 was synthesized with a yield of 62%: $^1$H NMR (400 MHz, CDCl$_3$): δ 3.92 (s, 4H), 3.73-3.62 (m, 8H), 3.39 (s, 8H), 1.61-1.50 (m, 4H), 1.29 (s, 36H), 0.88 (t, J=6.8 Hz, 6H); $^{13}$C NMR (100 MHz, CDCl$_3$): δ 73.9, 73.4, 72.2, 67.3, 64.9, 64.5, 48.2, 45.4, 45.1, 40.4, 35.6, 32.1, 29.8, 29.6, 29.5, 28.9, 26.3, 22.8, 14.3.

<6-2> Synthesis of TMG-T12a

According to the general glycosylation procedure of Example 2-2, Compound TMG-T12a was synthesized with a yield of 52%: $^1$H NMR (400 MHz, CDCl$_3$): δ 8.37-8.31 (m, 2H), 8.19-8.11 (m, 4H), 8.01-7.91 (m, 16H), 7.81-7.76 (m, 8H), 7.74-7.62 (m, 12H), 7.51-7.42 (m, 10H), 7.41-7.34 (m, 16H), 7.33-7.19 (m, 12H), 6.91-6.78 (m, 2H), 5.79-5.65 (m, 6H), 5.64-5.46 (m, 4H), 4.59-4.42 (m, 8H), 3.89-3.71 (m, 4H), 3.43-3.22 (m, 4H), 3.21-3.12 (m, 8H), 1.49-1.32 (m, 4H), 1.31-0.97 (m, 36H), 0.86 (t, J=6.4 Hz, 6H); $^{13}$C NMR (100 MHz, CDCl$_3$): δ 165.4, 165.2, 165.0, 164.9, 133.8, 133.5, 133.3, 133.2, 133.1, 130.5, 130.3, 130.1, 129.9, 129.8, 129.7, 129.5, 129.3, 129.2, 128.8, 128.6, 128.5, 128.4, 128.1, 101.7, 101.1, 72.8, 72.6, 72.2, 71.9, 71.6, 71.5, 70.1, 69.9, 63.3, 45.2, 32.2, 30.0, 29.9, 29.8, 29.7, 29.6, 26.3, 22.9, 14.4.

<6-3> Synthesis of TMG-T12

According to the general synthesis procedure for deprotection reaction of Example 2-3, TMG-T12 was synthesized with a yield of 95%: $^1$H NMR (400 MHz, CD$_3$OD): δ 4.38-31 (m, 4H), 3.97-3.84 (m, 8H), 3.74-3.68 (m, 4H), 3.65-3.53 (m, 4H), 3.47-3.37 (m, 12H), 3.29-3.17 (m, 4H), 1.61-1.49 (m, 4H), 1.41-1.20 (m, 36H), 0.90 (t, J=7.2 Hz, 6H); $^{13}$C NMR (100 MHz, CD$_3$OD): δ 105.1, 105.0, 78.0, 77.8, 75.2, 72.7, 71.7, 71.6, 71.2, 70.8, 70.6, 70.4, 62.8, 46.4, 33.2, 31.0, 30.9, 30.8, 30.7, 27.6, 23.9, 14.7; HRMS (EI): calcd. for $C_{58}H_{110}O_{26}S$ [M+Na]$^+$ 1255.5520 found 1255.7006.

<Preparation Example 7> Synthesis of TMG-T13

<7-1> Synthesis of Compound H3 (2,2'-(thiobis (methylene))bis(2-((tridecyloxy)methyl)propane-1,3-diol))

According to general procedure for the synthesis of 2,2'-(thiobis(methylene))bis(2-(alkyloxy)methyl)propane-1, 3-diol of Example 2-1, Compound H3 was synthesized with a yield of 63%: $^1$H NMR (400 MHz, CDCl$_3$): δ 3.92 (s, 4H), 3.75-3.63 (m, 8H), 3.41 (s, 8H), 1.61-1.51 (m, 4H), 1.29 (s, 40H), 0.88 (t, J=6.8 Hz, 6H); $^{13}$C NMR (100 MHz, CDCl$_3$): δ 73.9, 73.3, 72.2, 67.5, 64.9, 64.6, 64.4, 48.2, 45.4, 45.1, 44.6, 40.7, 40.4, 35.6, 32.1, 29.8, 29.6, 29.5, 28.9, 26.2, 22.8, 17.3, 14.3.

<7-2> Synthesis of TMG-T13a

According to the general glycosylation procedure of Example 2-2, Compound TMG-T13a was synthesized with a yield of 51%: $^1$H NMR (400 MHz, CDCl$_3$): δ 8.37-8.31 (m, 2H), 8.21-8.12 (m, 4H), 8.01-7.91 (m, 16H), 7.83-7.76 (m, 8H), 7.72-7.62 (m, 12H), 7.50-7.42 (m, 10H), 7.41-7.35 (m, 16H), 7.34-7.20 (m, 12H), 6.83-6.76 (m, 2H), 5.81-5.64 (m, 6H), 5.63-5.48 (m, 4H), 4.59-4.38 (m, 8H), 3.87-3.71 (m, 4H), 3.43-3.22 (m, 4H), 3.21-3.12 (m, 8H), 1.49-1.32 (m, 4H), 1.31-1.08 (m, 40H), 0.86 (t, J=6.4 Hz, 6H); $^{13}$C NMR (100 MHz, CDCl$_3$): δ 166.1, 165.9, 165.7, 165.4, 165.2, 165.0, 164.9, 133.7, 133.4, 133.2, 133.1, 133.0, 130.5, 130.3, 130.0, 129.9, 129.8, 129.7, 129.6, 129.4, 129.3, 129.2, 129.1, 129.0, 128.8, 128.7, 128.6, 128.5, 128.4, 128.0, 72.8, 71.6, 71.5, 71.4, 60.5, 45.2, 32.1, 29.9, 29.8, 29.7, 29.5, 26.2, 22.8, 21.2, 14.3.

<7-3> Synthesis of TMG-T13

According to the general synthesis procedure for deprotection reaction of Example 2-3, TMG-T13 was synthesized with a yield of 96%: $^1$H NMR (400 MHz, CD$_3$OD): δ 4.37-4.28 (m, 4H), 3.98-3.84 (m, 8H), 3.73-3.62 (m, 4H), 3.62-3.51 (m, 4H), 3.47-3.38 (m, 12H), 3.27-3.17 (m, 4H), 1.62-1.49 (m, 4H), 1.41-1.20 (m, 40H), 0.90 (t, J=7.2 Hz, 6H); $^{13}$C NMR (100 MHz, CD$_3$OD): δ 106.0, 105.0, 104.9, 78.1, 78.0, 77.8, 75.2, 74.7, 72.8, 72.7, 71.6, 71.5, 71.1, 62.8, 62.7, 46.4, 45.7, 33.2, 31.0, 30.9, 30.6, 27.5, 23.9, 14.6; HRMS (EI): calcd. for $C_{60}H_{114}O_{26}S$ [M+Na]$^+$ 1283.7319 found 1283.7316.

<Preparation Example 8> Synthesis of TMG-T14

<8-1> Synthesis of Compound H4 (2,2'-(thiobis (methylene))bis(2-((tetradecyloxy)methyl)propane-1,3-diol))

According to the general procedure for synthesis of 2,2'-(thiobis(methylene))bis(2-(alkyloxy)methyl)propane-1, 3-diol of Example 2-1, Compound H4 was synthesized with a yield of 65%: $^1$H NMR (400 MHz, CDCl$_3$): δ 3.94 (s, 4H), 3.78-3.51 (m, 8H), 3.35 (s, 8H), 1.52-1.36 (m, 4H), 1.23 (s, 44H), 0.88 (t, J=6.8 Hz, 6H); $^{13}$C NMR (100 MHz, CDCl$_3$): δ 73.7, 73.2, 72.2, 71.8, 67.6, 67.1, 64.9, 64.7, 64.4, 48.3, 45.4, 45.1, 44.7, 40.8, 40.4, 38.8, 35.5, 32.0, 29.8, 29.6, 29.5, 28.8, 26.2, 22.8, 17.2, 14.3.

<8-2> Synthesis of TMG-T14a

According to the general glycosylation procedure of Example 2-2, Compound TMG-T14a was synthesized with a yield of 51%: $^1$H NMR (400 MHz, CDCl$_3$): δ 8.37-8.32 (m, 2H), 8.21-8.14 (m, 4H), 8.01-7.89 (m, 16H), 7.83-7.78 (m, 8H), 7.73-7.64 (m, 12H), 7.52-7.40 (m, 10H), 7.39-7.32 (m, 16H), 7.31-7.18 (m, 12H), 6.83-6.76 (m, 2H), 5.81-5.63 (m, 6H), 5.62-5.49 (m, 4H), 4.57-4.34 (m, 8H), 3.88-3.72 (m, 4H), 3.45-3.23 (m, 4H), 3.22-3.12 (m, 8H), 1.50-1.32 (m, 4H), 1.31-1.04 (m, 44H), 0.86 (t, J=6.8 Hz, 6H); $^{13}$C NMR (100 MHz, CDCl$_3$): δ 165.9, 165.8, 165.4, 165.2, 165.0, 164.9, 133.7, 133.5, 133.2, 133.1, 130.5, 130.3, 130.0, 129.9, 129.6, 129.4, 129.3, 129.2, 129.1, 129.0, 128.8, 128.6, 128.5, 128.4, 128.2, 128.0, 72.5, 72.3, 72.2, 71.8, 71.6, 71.5, 70.6, 69.9, 69.8, 69.2, 68.0, 63.9, 63.2, 45.2, 34.4, 32.1, 29.9, 29.8, 29.7, 29.6, 26.3, 22.9, 14.3.

<8-3> Synthesis of TMG-T14

According to the general synthesis procedure of deprotection reaction of Example 2-3, TMG-T14 was synthesized with a yield of 96%: $^1$H NMR (400 MHz, CD$_3$OD): δ 4.38-4.28 (m, 4H), 3.97-3.82 (m, 8H), 3.74-3.65 (m, 4H), 3.64-3.51 (m, 4H), 3.48-3.38 (m, 12H), 3.29-3.16 (m, 4H), 1.62-1.50 (m, 4H), 1.42-1.18 (m, 44H), 0.90 (t, J=7.2 Hz, 6H); $^{13}$C NMR (100 MHz, CD$_3$OD): δ 105.1, 105.0, 78.1, 77.8, 75.2, 72.7, 71.7, 71.6, 71.2, 70.8, 70.6, 70.4, 62.8, 46.4, 33.2, 31.0, 30.9, 30.8, 30.6, 27.6, 23.9, 14.7.

<Example 3> Synthesis of TMMs

Figure 3:
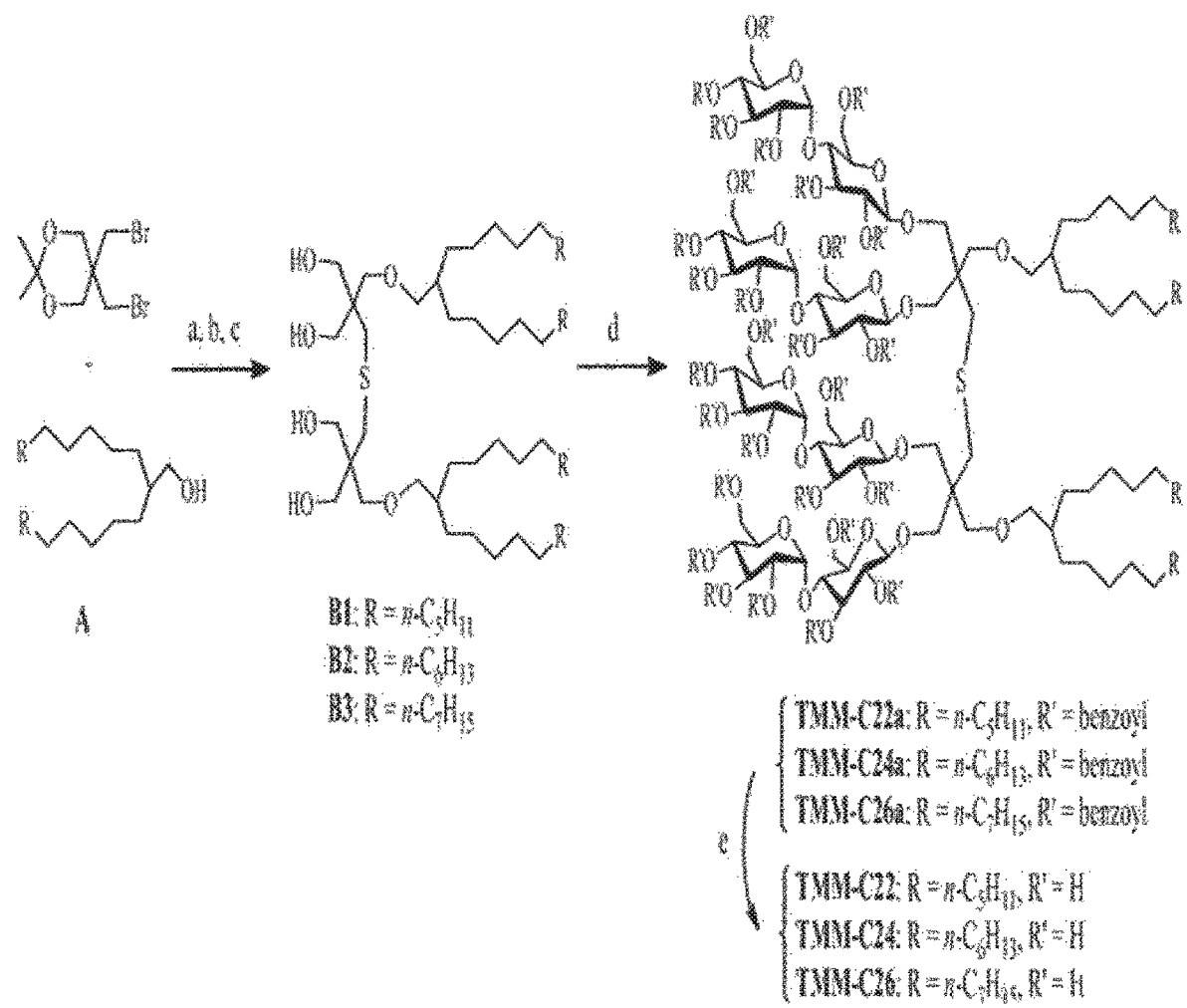
FIG. 3 is a diagram illustrating a synthesis scheme of TMMs according to Example 3 of the present invention.
Figure 4:
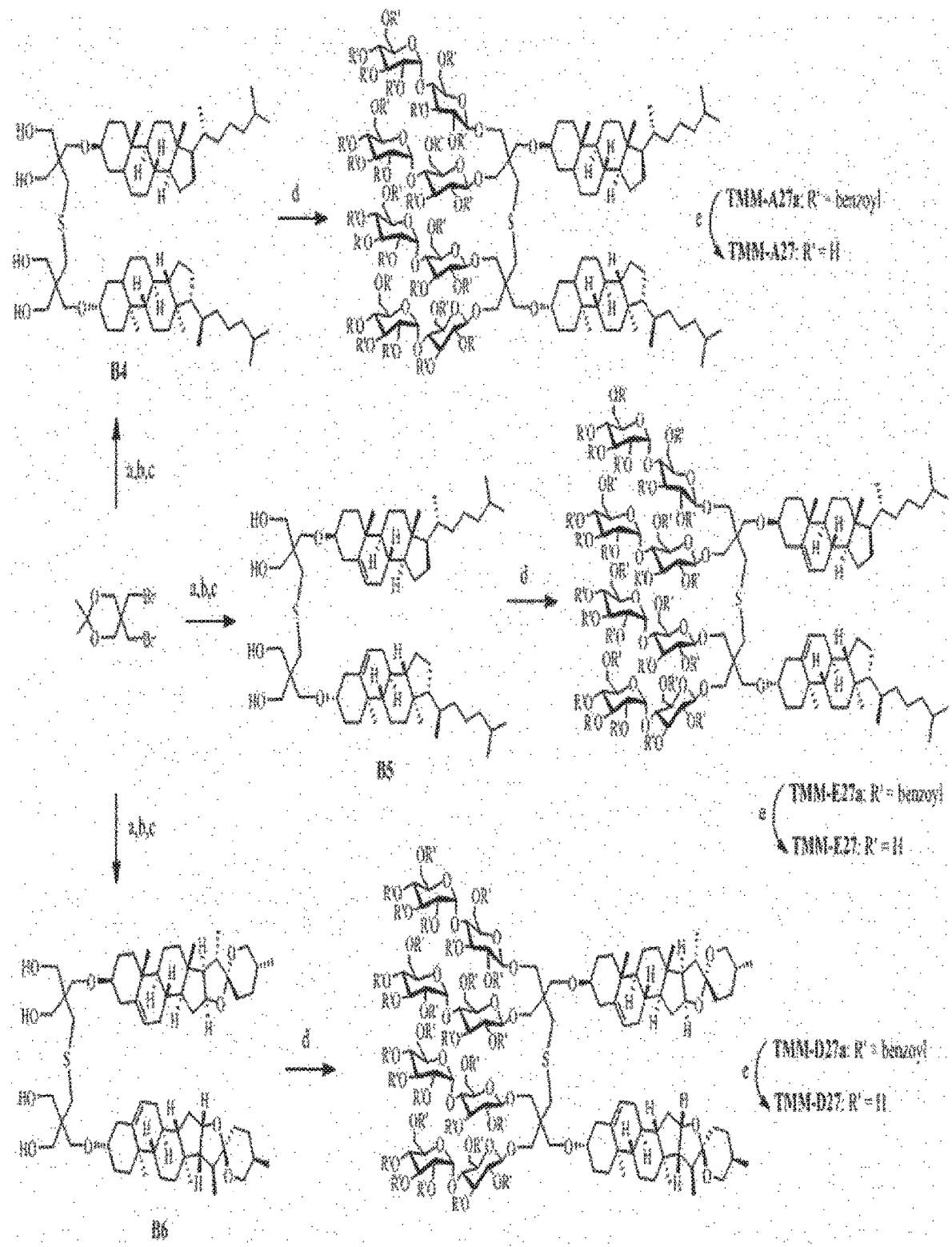
FIG. 4 is a diagram illustrating a synthesis scheme of TMM-A, E and D according to Example 3 of the present invention.

Synthesis schemes of TMMs were shown in FIGS. 3 and 4. Six types of TMM compounds were synthesized according to the synthesis methods in Examples 3-1 to 3-3 as follows.

<3-1> General Procedure for the Synthesis of Thioether-Containing Tetraol (Compound B in FIGS. 3 and 4; Steps a-c of FIGS. 3 and 4)

NaH (11.6 mmol, 1.2 equivalents, 60%) was added to a solution of a dialkylated mono-ol, cholesterol, cholestanol or diosgenin (11.6 mmol, 1 equivalent) dissolved in dry DMF (25 mL). 5,5-bis-bromomethyl-2,2-dimethyl-[1,3]dioxane (11.6 mmol, 1 equivalent) was added to the mixture, and stirred for 30 minutes at room temperature. A reaction flask was transferred to an oil container preheated to 120° C., and further stirring was carried out for 15 hours. After the reaction was completed (monitored by TLC), the reaction mixture was cooled at room temperature, rapidly cooled with ice-cold H$_2$O (50 mL), and extracted with ether (3×100 mL). The mixed organic layer was washed with brine (2×150 mL), dried with anhydrous Na$_2$SO$_4$, and concentrated using a rotary evaporator. The product (5.08 mmol, 1 equivalent) was dissolved in DMF (20 mL), and KI (5.08 mmol, 1 equivalent) was added to the solution. Following the addition of Na$_2$S. 9H$_2$O (0.6 equivalents) in water (5 mL) to the mixture, DMF (20 mL) was further added, and the mixture was transferred to an oil container preheated to 100° C. and stirred for 20 hours under nitrogen (N$_2$). After cooling, the mixture was poured into water (300 mL) and an organic layer was extracted with diethylether (150 mL). The organic layer was sequentially washed with water (300 mL), a 2.5% NaOH solution (300 mL) and brine (100 mL), dried with anhydrous Na$_2$SO$_4$ and filtered. The filtrate was stirred with 3 g of silica gel for 30 minutes, filtered, and concentrated by rotary evaporation. The concentrated reaction mixture was dissolved in a 1:1 mixture of CH$_2$Cl$_2$ and MeOH (50 mL), p-toluene sulfonic acid (p-TSA) monohydrate (200 mg) was added, and then the resulting mixture was stirred for 6 hours at room temperature. After the reaction, the reaction mixture was neutralized with a NaHCO$_3$ solution, filtered, and dried by rotary evaporation. By flash column chromatography (EtOAc/hexane), a white solid, thioether-containing tetraol (Compound B) was obtained.

<3-2> General Synthesis Procedure of Glycosylation Reaction (Step d of FIGS. 3 and 4)

AgOTf (5 equivalents) was added to a solution prepared by stirring Compound B and 2,4,6-collidine (3.0 equivalents) produced in Example 3-1 in CH$_2$Cl$_2$ (15 mL) at 0° C., and stirred for 10 minutes. A CH$_2$Cl$_2$ (10 mL) solution containing 5 equivalents of perbenzoylated maltosylbromide was slowly added to the mixture. The reaction was carried out with stirring for 30 minutes at 0° C. After the reaction, pyridine was added to the reaction mixture, and the mixture was diluted with CH$_2$Cl$_2$ (20 mL), before being filtered with Celite. The filtrate was sequentially washed with a 1M Na$_2$S$_2$O$_3$ aqueous solution (40 mL), a 0.1 M HCl aqueous solution (40 mL) and brine (3×40 mL). An organic layer was dried with anhydrous Na$_2$SO$_4$, and the solvent was removed using a rotary evaporator. A remaining substance was purified by silica gel column chromatography (EtOAc/hexane), thereby obtaining a glassy solid compound.

<3-3> General Synthesis Procedure for Deprotection Reaction (Step e of FIGS. 3 and 4)

In this method, de-O-benzoylation was performed under Zemplen's conditions (Ashton, P. R.; Boyd, S. E.; Brown, C. L.; Jayaraman, N.; Nepogodiev, S. A.; Stoddart, J. F. Chem.-Eur. J. 1996, 2, 1115-1128). O-protected Compound was dissolved with a small amount of anhydrous CH$_2$Cl$_2$, and MeOH was slowly added until precipitation. The reaction mixture was treated with a 0.5M methanolic solution, NaOMe, to have a final concentration of 0.05M. To prevent precipitation, the methanolic solution was slowly added. The reaction mixture was stirred for 6 hours at room temperature. After the reaction, the reaction mixture was neutralized using an Amberlite IR-120 (H$^+$ form) resin. The resin was removed by filtration and washed with MeOH, and then the solvent was removed from the filtrate in vacuo. A remaining substance was recrystallized using CH$_2$Cl$_2$/MeOH/diethyl ether, thereby obtaining a white solid compound, from which a protective group was completely removed.

<Preparation Example 9> Synthesis of TMM-C22

<9-1> Synthesis of Compound B1

According to the general procedure for synthesis of thioether-containing tetraol of Example 3-1, Compound B1 was synthesized with a yield of 53%: $^1$H NMR (400 MHz, CDCl$_3$): δ 3.94 (s, 4H), 3.63 (s, 8H), 3.54 (d, J=8.4 Hz, 4H), 3.21 (s, 4H), 1.58-1.49 (m, 2H), 1.26 (s, 72H), 0.89 (t, J=7.6 Hz, 12H); $^{13}$C NMR (100 MHz, CDCl$_3$): δ 73.3, 72.7, 66.1, 65.2, 45.4, 41.2, 35.6, 33.2, 30.9, 30.8, 28.8, 27.5, 23.9, 21.5, 14.6.

<9-2> Synthesis of TMM-C22a

According to the general glycosylation procedure of Example 3-2, Compound TMM-C22a was synthesized with a yield of 51%: $^1$H NMR (400 MHz, CDCl$_3$): δ 8.21-7.90 (m, 32H), 7.89-7.78 (m, 18H), 7.77-7.59 (m, 10H), 7.58-7.45 (m, 28H), 7.44-7.32 (m, 20H), 7.31-7.11 (m, 32H), 6.14 (t, J=8.4 Hz, 4H), 5.66 (s, 8H), 5.46-5.23 (m, 4H), 5.19-5.02 (m, 8H), 4.79-4.62 (m, 10H), 4.61-3.99 (m, 16H), 3.81-3.36 (m, 8H), 3.22-3.01 (m, 4H), 2.99-2.54 (m, 16H), 2.42-2.15 (m, 2H), 1.25 (s, 72H), 0.86 (t, J=7.6 Hz, 12H); $^{13}$C NMR (100 MHz, CDCl$_3$): δ 166.2, 165.9, 165.8, 165.6, 165.2, 165.0, 133.6, 133.3, 130.1, 129.9, 129.8, 129.4, 129.2, 129.0, 128.8, 128.5, 128.4, 95.8, 72.2, 71.5, 69.9, 69.2, 62.5, 60.6, 53.6, 32.1, 29.9, 29.6, 22.9, 21.2, 14.4.

<9-3> Synthesis of TMM-C22

According to the general synthesis procedure for deprotection reaction of Example 3-3, TMM-C22 was synthesized with a yield of 92%: $^1$H NMR (400 MHz, CD$_3$OD): δ 5.21 (d, J=3.8 Hz, 4H), 4.41-3.36 (m, 4H), 3.95-3.82 (m, 10H), 3.81-3.67 (m, 20H), 3.66-3.58 (m, 16H), 3.57-3.49 (m, 14H), 3.31-3.02 (m, 4H), 1.68-1.51 (m, 2H), 1.30 (s, 72H), 0.90 (t, J=7.2 Hz, 12H); $^{13}$C NMR (100 MHz, CD$_3$OD): δ 105.0, 103.1, 81.4, 77.9, 76.7, 75.2, 74.9, 74.3, 71.6, 62.9, 62.3, 46.7, 33.2, 31.7, 30.9, 30.8, 30.7, 23.9, 14.7; MS (MALDI-TOF): calcd. for C$_{102}$H$_{190}$O$_{46}$S [M+H]$^+$ 2184.6560, found 2184.1526.

<Preparation Example 10> Synthesis of TMM-C24

<10-1> Synthesis of Compound B2

According to the general procedure for synthesis of thioether-containing tetraol of Example 3-1, Compound B2 was synthesized with a yield of 53%: $^1$H NMR (400 MHz, CDCl$_3$): δ 3.93 (s, 4H), 3.87 (s, 8H), 3.59 (d, J=8.4 Hz, 4H), 3.21 (s, 4H), 1.53-1.46 (m, 2H), 1.26 (s, 80H), 0.88 (t, J=7.6 Hz, 12H); $^{13}$C NMR (100 MHz, CDCl$_3$): δ 73.3, 72.6, 67.9, 64.9, 45.5, 41.7, 37.9, 31.2, 30.8, 29.5, 28.8, 23.5, 21.6, 14.6.

<10-2> Synthesis of TMM-C24a

According to the general glycosylation procedure of Example 3-2, Compound TMM-C24a was synthesized with a yield of 49%: $^1$H NMR (400 MHz, CDCl$_3$): δ 8.21-7.90 (m, 32H), 7.89-7.77 (m, 18H), 7.76-7.58 (m, 10H), 7.57-7.45 (m, 28H), 7.44-7.32 (m, 20H), 7.31-7.09 (m, 32H), 6.15 (t, J=8.4 Hz, 4H), 5.65 (s, 8H), 5.46-5.21 (m, 4H), 5.20-5.01 (m, 8H), 4.79-4.62 (m, 10H), 4.61-3.99 (m, 16H), 3.81-3.35 (m, 8H), 3.21-3.01 (m, 4H), 2.97-2.54 (m, 16H), 2.42-2.18 (m, 2H), 1.25 (s, 80H), 0.86 (t, J=7.6 Hz, 12H); $^{13}$C NMR (100 MHz, CDCl$_3$): δ 166.3, 166.0, 165.8, 165.7, 165.2, 165.0, 164.7, 133.4, 133.2, 130.4, 130.1, 129.9, 129.7, 129.6, 129.4, 129.2, 129.0, 128.9, 128.7, 128.4, 127.9, 95.9, 75.3, 74.7, 72.7, 72.2, 71.6, 70.5, 70.4, 69.9, 69.1, 63.7, 62.4, 60.5, 32.1, 30.6, 29.9, 29.6, 22.9, 22.3, 21.2, 14.3.

<10-3> Synthesis of TMM-C24

According to the general synthesis procedure for deprotection reaction of Example 3-3, TMM-C24 was synthesized with a yield of 92%: $^1$H NMR (400 MHz, CD$_3$OD): δ 5.20 (d, J=3.8 Hz, 4H), 4.39-3.37 (m, 4H), 3.94-3.82 (m, 12H), 3.81-3.68 (m, 18H), 3.67-3.59 (m, 18H), 3.58-3.49 (m, 12H), 3.32-3.03 (m, 4H), 1.69-1.52 (m, 2H), 1.30 (s, 80H), 0.90 (t, J=7.2 Hz, 12H); $^{13}$C NMR (100 MHz, CD$_3$OD): δ 105.0, 103.0, 81.4, 77.8, 76.7, 75.2, 74.9, 71.6, 62.8, 62.3, 33.2, 30.9, 30.7, 23.9, 14.7; MS (MALDI-TOF): calcd. for C$_{106}$H$_{198}$O$_{46}$S [M+H]$^+$ 2240.7640, found 2240.1177.

<Preparation Example 11> Synthesis of TMM-C26

<11-1> Synthesis of Compound B3

According to the general procedure for synthesis of thioether-containing tetraol of Example 3-1, Compound B3 was synthesized with a yield of 52%: $^1$H NMR (400 MHz, CDCl$_3$): δ 3.84 (s, 4H), 3.78 (s, 8H), 3.40 (d, J=8.4 Hz, 4H), 2.98 (s, 4H), 1.58-1.46 (m, 2H), 1.26 (s, 88H), 0.87 (t, J=7.6 Hz, 12H); $^{13}$C NMR (100 MHz, CDCl$_3$): δ 73.2, 72.6, 67.7, 64.8, 45.3, 41.4, 37.9, 32.1, 31.4, 30.8, 29.9, 29.6, 23.6, 22.9, 14.4.

<11-2> Synthesis of TMM-C26a

According to the general glycosylation procedure of Example 3-2, Compound TMM-C26a was synthesized with a yield of 49%: $^1$H NMR (400 MHz, CDCl$_3$): δ 8.23-7.92 (m, 32H), 7.91-7.79 (m, 18H), 7.78-7.59 (m, 10H), 7.58-7.45 (m, 28H), 7.44-7.32 (m, 20H), 7.31-7.13 (m, 32H), 6.15 (t, J=8.4 Hz, 4H), 5.66 (s, 8H), 5.45-5.22 (m, 4H), 5.20-5.04 (m, 8H), 4.78-4.64 (m, 10H), 4.63-3.98 (m, 16H), 3.81-3.36 (m, 8H), 3.22-3.02 (m, 4H), 2.99-2.54 (m, 16H), 2.42-2.18 (m, 2H), 1.26 (s, 88H), 0.86 (t, J=5.7 Hz, 12H); $^{13}$C NMR (100 MHz, CDCl$_3$): δ 166.2, 165.9, 165.7, 165.2, 165.0, 164.8, 133.6, 133.3, 133.1, 129.9, 129.8, 129.6, 129.4, 129.1, 129.0, 128.8, 128.5, 128.4, 95.9, 74.8, 72.2, 71.4, 69.9, 69.1, 63.5, 62.6, 32.1, 29.9, 29.6, 22.9, 14.3.

<11-3> Synthesis of TMM-C26

According to the general synthesis procedure for deprotection reaction of Example 3-3, TMM-C26 was synthesized with a yield of 90%: $^1$H NMR (400 MHz, CD$_3$OD): δ 5.18 (d, J=3.8 Hz, 4H), 4.38-3.39 (m, 4H), 3.92-3.81 (m, 12H), 3.79-3.67 (m, 18H), 3.66-3.57 (m, 18H), 3.56-3.47 (m, 12H), 3.31-3.02 (m, 4H), 1.68-1.51 (m, 2H), 1.29 (s, 88H), 0.90 (t, J=7.2 Hz, 12H); $^{13}$C NMR (100 MHz, CD$_3$OD): δ 105.1, 103.0, 81.5, 77.9, 76.6, 75.2, 74.9, 74.3, 72.7, 71.6, 62.9, 62.4, 33.3, 31.0, 30.7, 27.6, 23.9, 14.7; MS (MALDI-TOF): calcd. for C$_{110}$H$_{206}$O$_{46}$S [M+H]$^+$ 2296.8720, found 2296.6560.

<Preparation Example 12> Synthesis of TMM-A27

<12-1> Synthesis of Compound B4

According to the general procedure for synthesis of thioether-containing tetraol of Example 3-1, Compound B4 was synthesized with a yield of 53%: $^1$H NMR (400 MHz, CDCl$_3$): δ 3.79-3.58 (m, 12H), 3.52 (s, 4H), 3.21-3.17 (m, 2H), 3.00 (s, 2H), 2.78 (s, 2H), 1.96 (d, J=6.4 Hz, 2H), 1.90-0.78 (m, 78H), 0.61 (s, 12H); $^{13}$C NMR (100 MHz, CDCl$_3$): δ 80.0, 71.1, 65.2, 56.7, 56.5, 54.5, 44.9, 44.8, 42.8, 40.2, 39.7, 37.0, 36.4, 36.0, 35.9, 35.7, 34.8, 32.3, 29.0, 28.4, 28.3, 28.2, 24.4, 24.0 23.0, 22.8, 21.4, 18.9. 12.2.

<12-2> Synthesis of TMM-A27a

According to the general glycosylation procedure of Example 3-2, compound TMM-A27a was synthesized with a yield of 52%: $^1$H NMR (400 MHz, CDCl$_3$): δ 8.09-8.05 (m, 10H), 8.04-7.96 (m, 14H), 7.95-7.82 (m, 24H), 7.79-7.65 (m, 10H), 7.55-7.47 (m, 22H), 7.46-7.38 (m, 16H), 7.37-7.30 (m, 24H), 7.27-7.19 (m, 20H), 6.08 (t, J=7.8 Hz, 4H), 5.69-5.54 (m, 10H), 5.40 (t, J=7.8 Hz, 4H), 5.21-5.04 (m, 8H), 4.72-4.38 (m, 8H), 4.37-4.02 (m, 16H), 3.78-3.59 (m, 8H), 3.26-3.11 (m, 6H), 3.04-2.76 (m, 8H), 1.92-0.65 (m, 74H), 0.56 (s, 6H); $^{13}$C NMR (100 MHz, CDCl$_3$): δ 166.3, 165.9, 165.7, 165.2, 164.9, 133.7, 133.6, 133.3, 130.1, 130.0, 129.9, 129.8, 129.6, 129.5, 129.1, 129.0, 128.9, 128.8, 128.6, 128.4, 101.0, 95.9, 79.2, 74.9, 72.4, 72.2, 71.4, 70.0, 69.1, 69.0, 67.9, 63.6, 62.5, 56.5, 54.1, 44.8, 44.6, 42.7, 40.1, 39.7, 36.4, 36.0, 35.6, 35.4, 34.9, 31.9, 28.8, 28.4, 28.2, 28.1, 24.3, 24.0, 19.2, 12.9, 12.8.

<12-3> Synthesis of TMM-A27

According to the general synthesis procedure for deprotection reaction of Example 3-3, TMM-A27 was synthesized with a yield of 92%: $^1$H NMR (400 MHz, (CD$_3$)$_2$SO): δ 5.67-5.44 (m, 12H), 5.37-5.01 (m, 4H), 4.98-4.71 (m, 12H), 4.61-4.35 (m, 14H), 3.21-3.11 (m, 12), 2.10-0.79 (m, 72H), 0.77-0.49 (m, 12H); $^{13}$C NMR (100 MHz, (CD$_3$)$_2$SO): δ 105.4, 100.5, 79.2, 75.9, 74.7, 73.1, 72.9, 72.8, 72.1, 69.5, 60.4, 60.1, 55.5, 44.8, 41.8, 39.8, 34.9, 34.7, 27.0, 22.3, 22.1, 18.2, 11.8; MS (MALDI-TOF): calcd. for $C_{112}H_{194}O_{46}S$ [M+H]$^+$ 2308.7980, found 2308.2026.

<Preparation Example 13> Synthesis of TMM-E27

<13-1> Synthesis of Compound B5

According to the general procedure for synthesis of thioether-containing tetraol of Example 3-1, Compound B5 was synthesized with a yield of 52%: $^1$H NMR (400 MHz, CDCl$_3$): δ 5.35 (t, J=5.1 Hz, 2H), 3.66-3.58 (m, 12H), 3.43 (s, 2H), 3.35 (s, 4H), 3.20-3.17 (m, 2H), 2.78 (s, 2H), 2.99 (t, J=4.8 Hz, 2H), 2.31-2.23 (m, 2H), 2.19-0.71 (m, 76H), 0.67 (s, 6H); $^{13}$C NMR (100 MHz, CDCl$_3$): δ 140.9, 122.0, 79.9, 75.1, 72.6, 71.2, 67.0, 65.1, 59.8, 57.0, 56.3, 50.4, 45.2, 42.5, 40.0, 39.7, 39.1, 37.4, 37.0, 36.4, 36.0, 32.1, 29.9, 28.5, 28.4, 28.2, 24.5, 24.0, 23.6, 22.8, 21.3, 19.6, 18.9, 12.1.

<13-2> Synthesis of TMM-E27a

According to the general glycosylation procedure of Example 3-2, Compound TMM-E27a was synthesized with a yield of 51%: $^1$H NMR (400 MHz, CDCl$_3$): δ 8.09-8.05 (m, 10H), 8.04-7.95 (m, 14H), 7.94-7.82 (m, 22H), 7.79-7.65 (m, 12H), 7.55-7.46 (m, 22H), 7.45-7.37 (m, 16H), 7.36-7.30 (m, 24H), 7.27-7.19 (m, 20H), 6.07 (t, J=7.8 Hz, 4H), 5.69-5.55 (m, 10H), 5.40 (t, J=7.8 Hz, 4H), 5.21-5.03 (m, 10H), 4.71-4.40 (m, 8H), 4.37-4.02 (m, 16H), 3.78-3.59 (m, 8H), 3.26-3.11 (m, 6H), 3.04-2.76 (m, 8H), 1.92-0.65 (m, 76H), 0.56 (s, 6H); $^{13}$C NMR (100 MHz, CDCl$_3$): δ 166.3, 166.0, 165.7, 165.2, 165.0, 133.6, 133.3, 130.1, 129.9, 129.8, 129.7, 129.6, 129.5, 129.2, 129.1, 128.9, 128.8, 128.6, 128.4, 101.0, 95.9, 79.2, 74.9, 72.4, 72.2, 71.4, 70.0, 69.0, 67.8, 62.6, 56.5, 54.2, 44.8, 44.5, 42.7, 40.2, 39.7, 36.8, 36.0, 35.6, 35.4, 34.8, 28.6, 28.4, 28.2, 28.0, 23.0, 22.8, 19.4, 18.9, 14.4, 12.0.

<13-3> Synthesis of TMM-E27

According to the general synthesis procedure for deprotection reaction of Example 3-3, TMM-E27 was synthesized with a yield of 92%: $^1$H NMR (400 MHz, (CD$_3$)$_2$SO): δ 5.64-5.41 (m, 14H), 5.34-4.97 (m, 4H), 4.95-4.69 (m, 12H), 4.59-4.34 (m, 14H), 3.23-3.14 (m, 12H), 2.10-0.83 (m, 68H), 0.82-0.52 (m, 14H); $^{13}$C NMR (100 MHz, (CD$_3$)$_2$SO): δ 129.8, 103.6, 100.8, 79.5, 76.2, 75.0, 73.4, 73.3, 73.1, 72.4, 69.9, 60.8, 60.4, 41.8, 27.3, 22.6, 22.3, 19.0, 18.5, 11.6; MS (MALDI-TOF): calcd. for $C_{112}H_{190}O_{46}S$ [M+H]$^+$ 2304.7660, found 2304.1122.

<Preparation Example 14> Synthesis of TMM-D27

<14-1> Synthesis of Compound B6

According to the general procedure for synthesis of thioether-containing tetraol of Example 3-1, Compound B6 was synthesized with a yield of 53%: $^1$H NMR (400 MHz, CDCl$_3$): δ 5.34 (t, J=5.1 Hz, 2H), 4.39 (q, J=5.7 Hz, 2H), 3.72 (s, 8H), 3.58-3.49 (m, 6H), 3.36 (s, 2H), 3.14 (t, J=4.8 Hz, 2H), 2.68 (s, 4H), 2.38-2.28 (m, 2H), 2.21-0.85 (m, 70H), 0.83-0.75 (m, 12H); $^{13}$C NMR (100 MHz, CDCl$_3$): δ 140.4, 121.7, 109.3, 80.8, 80.1, 70.9, 66.9, 65.0, 62.1, 56.5, 50.0, 44.6, 41.6, 40.3, 39.8, 38.8, 37.0, 32.1, 31.8, 31.4, 30.3, 28.8, 28.2, 20.9, 19.4, 17.2, 16.3, 14.6.

<14-2> Synthesis of TMM-D27a

According to the general glycosylation procedure of Example 3-2, Compound TMM-D27a was synthesized with a yield of 52%: $^1$H NMR (400 MHz, CDCl$_3$): δ 8.10-8.05 (m, 10H), 8.04-7.96 (m, 14H), 7.95-7.82 (m, 24H), 7.80-7.66 (m, 10H), 7.55-7.46 (m, 22H), 7.45-7.38 (m, 16H), 7.37-7.30 (m, 24H), 7.27-7.19 (m, 20H), 6.08 (t, J=7.8 Hz, 4H), 5.69-5.54 (m, 12H), 5.40 (t, J=7.8 Hz, 4H), 5.21-5.04 (m, 8H), 4.72-4.38 (m, 12H), 4.37-4.02 (m, 16H), 3.78-3.59 (m, 8H), 3.26-3.11 (m, 6H), 3.04-2.76 (m, 8H), 2.01-0.73 (m, 68H), 0.71-0.54 (m, 12H); $^{13}$C NMR (100 MHz, CDCl$_3$): δ 166.2, 165.9, 165.8, 165.6, 165.1, 164.9, 140.8, 133.5, 133.3, 133.2, 130.0, 129.8, 129.7, 129.6, 129.5, 129.4, 129.0, 128.8, 128.7, 128.5, 128.4, 120.9, 109.4, 100.9, 81.0, 79.2, 74.8, 72.3, 72.2, 71.3, 69.9, 69.0, 67.8, 67.0, 63.5, 62.5, 62.2, 56.5, 49.8, 44.7 41.7, 40.3, 39.9, 38.8, 37.0, 36.8, 31.9, 31.5, 31.2, 30.4, 28.9, 28.3, 19.4, 17.3, 16.4, 14.7, 14.3.

<14-3> Synthesis of TMM-D27

According to the general synthesis procedure for the deprotection reaction of Example 3-3, TMM-D27 was synthesized with a yield of 92%: $^1$H NMR (400 MHz, (CD$_3$)$_2$SO): δ 5.51-5.32 (m, 10H), 5.18-5.01 (m, 4H), 4.61-4.35 (m, 12H), 4.33-4.11 (m, 6H), 3.89-3.68 (m, 20H), 3.67-3.49 (m, 16H), 3.19-2.97 (m, 14H), 2.10-0.82 (m, 64H), 0.81-0.51 (m, 12H); $^{13}$C NMR (100 MHz, (CD$_3$)$_2$SO): δ 140.7, 108.4, 103.7, 100.8, 80.2, 79.5, 78.9, 76.2, 75.0, 73.4, 73.3, 73.1, 72.4, 69.9, 68.0, 60.8, 60.4, 55.7, 41.0, 36.4, 31.0, 19.1, 17.0, 16.0, 14.6; MS (MALDI-TOF): calcd. for $C_{112}H_{182}O_{46}S$ [M+H]$^+$ 2360.6980, found 2360.8740.

<Example 4> Structures of TMGs/TMMs

Each of the TMGs has two alkyl chains as hydrophobic groups and four glucoses as hydrophilic groups. TMGs are classified into TMG-As and TMG-Ts according to the structure of a linker. TMG-As have a structure in which two malonate-derived units are linked by a propylene linker and alkyl chains are directly introduced to a tandem malonate-based backbone linked by the linker. In contrast, TMG-Ts have a structure in which two malonate-derived units are linked by a thioether-functionalized linker and alkyl chains are linked to a tandem malonate-based backbone linked by the linker using an ether group.

Each of the TMMs has a branched alkyl chain or an organic group having a steroid backbone as a hydrophobic group, and four maltoses as hydrophilic groups. TMMs may have a branched dialkyl group, cholesterol, cholestanol or diosgenin as a hydrophobic group.

Since an optimized balance between hydrophilic domains and hydrophobic domains (hydrophilic-hydrophobic balance) is essential for effective stabilization of a membrane protein, TMGs/TMMs were synthesized to discover amphipathic molecules having the optimal balance by changing the type and chain length of a functional group constituting a hydrophobic group according to a degree of hydrophilicity of a hydrophilic group.

<Example 5> Characteristics of TMGs and TMMs

Molecular weights (M.W.) of TMGs and TMMs, critical micellar concentrations (CMC) and the hydrodynamic radii (hydrodynamic radii; $R_h$) of formed micelles were measured.

Specifically, a CMC was measured using fluorescent staining and diphenylhexatriene (DPH), and the hydrodynamic radii ($R_h$) of micelles formed by each agent (1.0 wt %) were measured by a DLS test. The measured results were compared with those for the conventional amphipathic molecule (detergent), DDM, and thus are shown in Table 1.

TABLE 1

| Detergent | M.W. | CMC (mM) | CMC (wt %) | $R_h$ (nm) |
|---|---|---|---|---|
| TMG-A11 | 1149.41 | ~0.015 | ~0.0017 | 3.1 ± 0.15 |
| TMG-A12 | 1177.47 | ~0.010 | ~0.0012 | 3.3 ± 0.09 |
| TMG-A13 | 1205.52 | ~0.006 | ~0.0007 | 3.6 ± 0.16 |
| TMG-A14 | 1233.58 | ~0.004 | ~0.0005 | 3.8 ± 0.10 |
| TMG-T11 | 1227.50 | ~0.020 | ~0.0025 | 3.0 ± 0.07 |
| TMG-T12 | 1255.55 | ~0.015 | ~0.0019 | 3.1 ± 0.06 |
| TMG-T13 | 1283.61 | ~0.006 | ~0.0008 | 3.3 ± 0.08 |
| TMG-T14 | 1311.66 | ~0.004 | ~0.0005 | 3.8 ± 0.09 |
| TMM-C22 | 2184.66 | ~0.002 | ~0.00044 | 3.6 ± 0.09 |
| TMM-C24 | 2240.76 | ~0.0015 | ~0.00034 | 3.9 ± 0.08 |
| TMM-C26 | 2296.87 | ~0.0015 | ~0.00034 | 4.3 ± 0.07 |
| TMM-A27 | 2308.80 | ~0.006 | ~0.00014 | 4.1 ± 0.10 |
| TMM-E27 | 2304.77 | ~0.008 | ~0.00018 | 4.7 ± 0.10 |
| TMM-D27 | 2360.70 | ~0.010 | ~0.0024 | 3.1 ± 0.07 |
| DDM | 510.1 | ~0.17 | ~0.0087 | 3.4 ± 0.03 |

Figure 5:
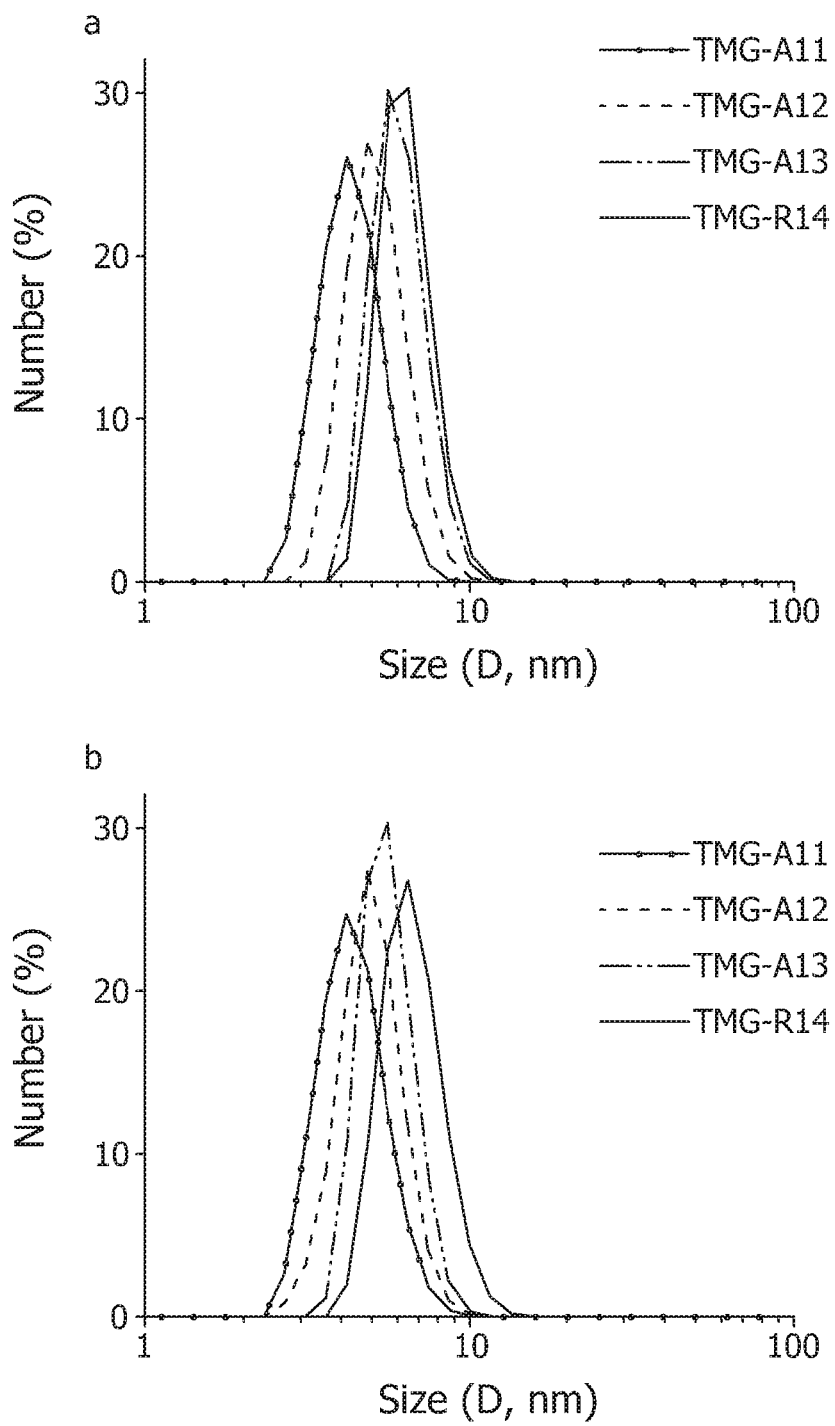
FIG. 5 shows the hydrodynamic radii ($R_h$) of micelles formed by TMGs (1.0 wt %), which are measured by a dynamic light scattering (DLS) test.
Figure 6:
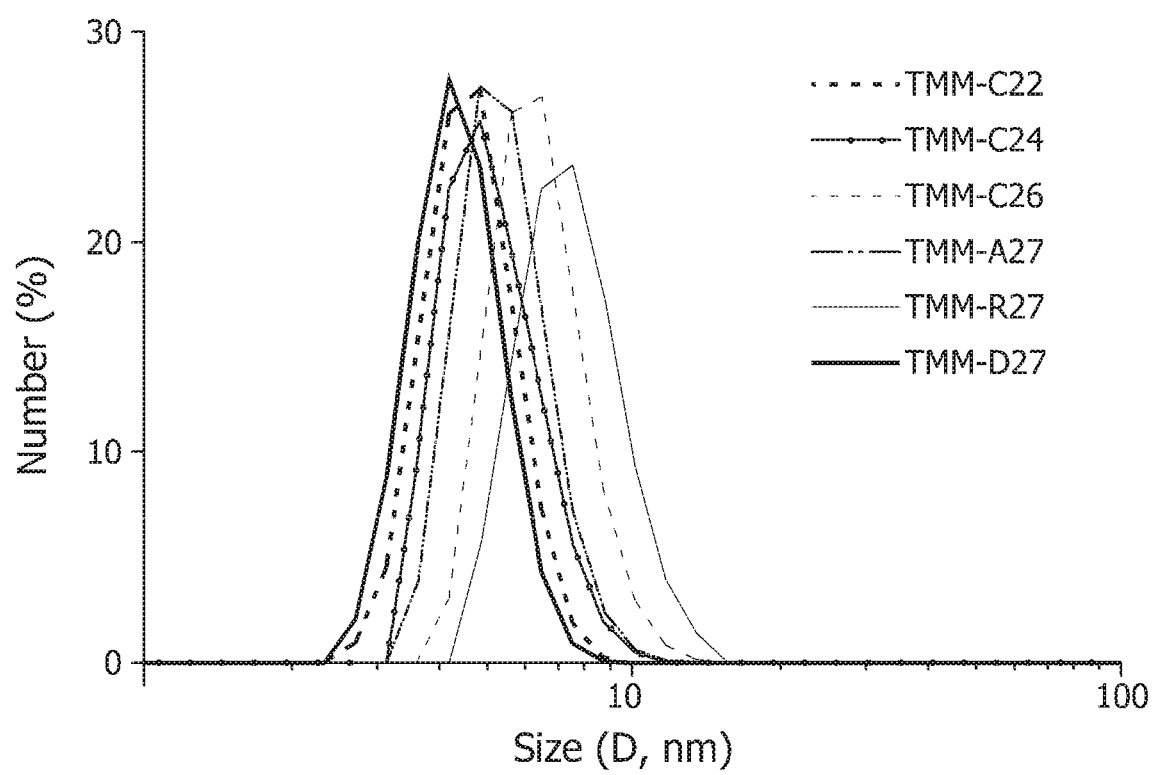
FIG. 6 shows the hydrodynamic radii ($R_h$) of micelles formed by TMMs (1.0 wt %), which are measured by a DLS test.

The CMC values (0.002 to 0.020 mM) of all the TMGs and TMMs were significantly smaller than those of DDM (0.17 mM). Therefore, since TMGs and TMMs easily form micelles even at lower concentrations, they may have the same or superior effects, compared to DDM, even at small amounts. In addition, it is considered that the CMC values of TMGs and TMMs were decreased by increasing the lengths of the alkyl chains because of increased hydrophobicity as the lengths of the alkyl chains were extended. Generally, sizes of the micelles formed by TMGs and TMMs tended to increase as the alkyl chains were extended. It is because the geometric structure of the molecule is closer to a cylindrical shape and thus forms a spherical self-assembled structure with a large curvature as the alkyl chain is extended. In the comparison of TMG-As with TMG-Ts, TMG-Ts formed smaller micelles than TMG-As. TMMs tended to form somewhat larger micelles than TMGs, Particularly, micelles of TMM-A27 and TMM-E27 having cholestanol and cholesterol as hydrophobic groups, respectively, were large. However, TMM-D27 having diosgenin as a hydrophobic group formed relatively small micelles. From analysis of DLS data, all amphipathic molecules (TMGs and TMMs) of the present invention formed a single micelle group and thus exhibit high micelle homogeneity (FIGS. 5 and 6).

<Example 6> Evaluation of Super Assembly Stability of *Rhodobacter capsulatus* Solubilized by TMGs The super-assembly of *R. capsulatus* expressed in manipulated *R. capsulatus* strains was solubilized and purified according to a protocol disclosed in previous literature (P. S. Chae, *Analyst*, 2015, 140, 3157-3163.). A 10 mL aliquot of a frozen membrane was thawed, and homogenized using a glass tissue homogenizer at room temperature. The homogenate was incubated for 30 minutes at 32° C. under gentle agitation. After addition of 1.0 wt % DDM, the homogenate was further incubated for 30 minutes at 32° C. Following ultracentrifugation, a supernatant containing a solubilized light harvesting complex I and reaction center (LHI-RC) complex was collected, and incubated with an $Ni^{2+}$-NTA resin for 1 hour at 4° C. The resin was added to each 10 His-SpinTrap column, and then the resulting product was washed with 500 µL of a coupling buffer (10 mM Tris (pH 7.8), 100 mL NaCl, 1×CMC DDM) twice. The LHI-RC complex purified by DDM was eluted from the column using a buffer containing 1.0 M imidazole (2×300 µL). To reach the final amphipathic molecule concentration of CMC+0.04 wt % or CMC+0.2 wt %, the LHI-RC complex purified by 80 µL of DDM was diluted with 920 µL each of the solutions of the following amphipathic molecules; TMG-As (TMG-A11, TMG-A12, TMG-A13 and TMG-A14), TMG-Ts (TMG-T11, TMG-T12, TMG-T13 and TMG-T14) or DDM. The LHI-RC complex produced by each amphipathic molecule was incubated for 20 days at room temperature. Protein stability was measured at regular intervals while a protein-amphipathic molecule sample was incubated by measuring the UV-visible spectrum of a specimen in a range of 650 to 950 nm.

Figure 7:
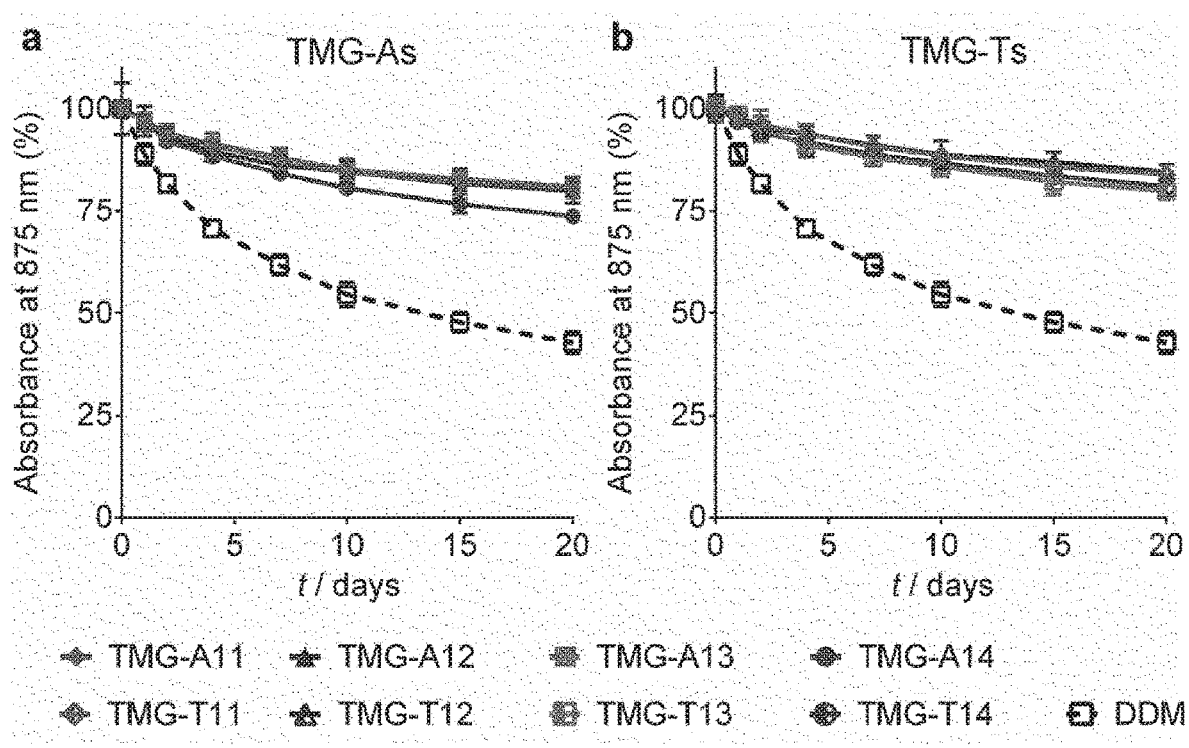
FIG. 7 shows the results of measuring stability of LHI-RC complexes produced by CMC+0.04 wt % amphipathic molecules at regular intervals for 20 days.
Figure 8:
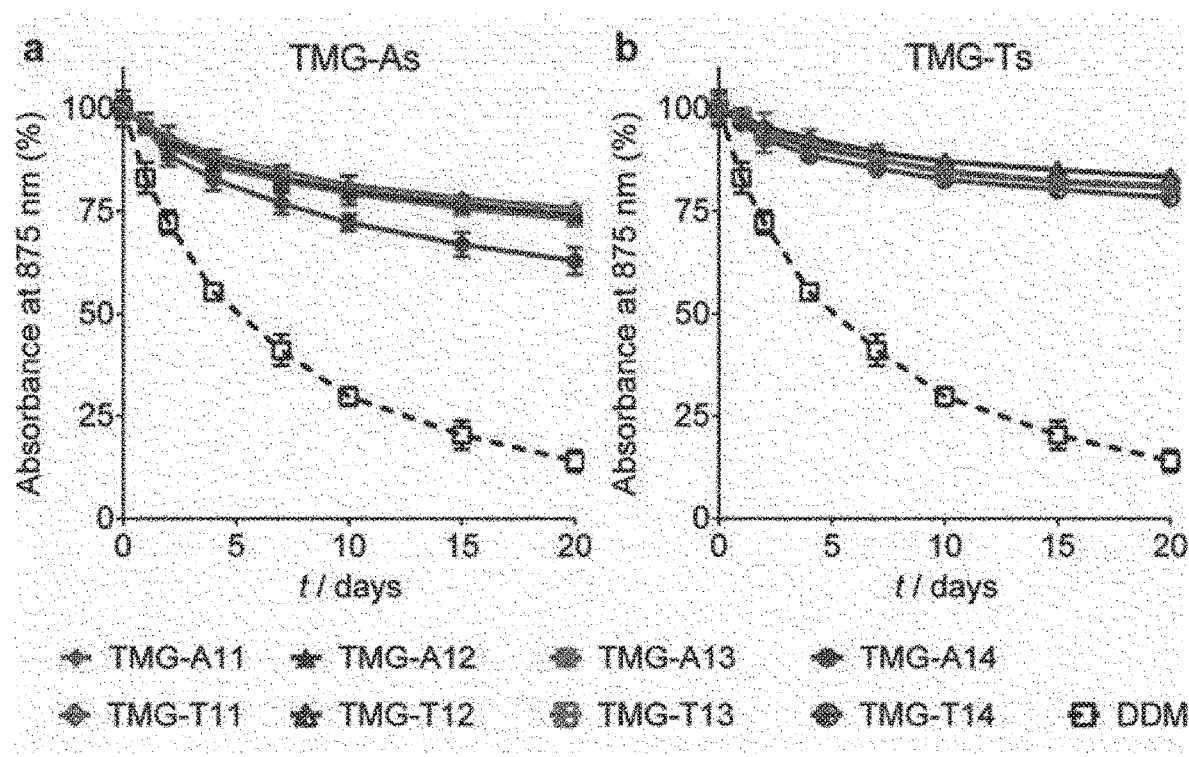
FIG. 8 shows the results of measuring stability of LHI-RC complexes produced by CMC+0.2 wt % amphipathic molecules at regular intervals for 20 days.

As a result, compared to DDM, TMGs of the present invention exhibited considerable excellence in maintaining the stability of the LHI-RC complex. In comparison of two groups of TMGs, TMG-Ts were somewhat more excellent than TMG-As. When the concentration of the amphipathic molecule was reduced to CMC+0.04 wt %, a difference in maintenance of the LHI-RC complex stability between TMGs and DDM was reduced, but overall, as the maintenance of the LHI-RC complex stability increased, TMGs and DDM showed a similar tendency (FIG. 7). While all TMGs were effective in stabilizing the LHI-RC complex at all concentrations of CMC+0.04 wt % and CMC+0.2 wt %, DDM significantly reduced complex stabilization as the concentration increased from CMC+0.04 wt % to CMC+0.2 wt % (FIGS. 7 and 8).

<Example 7> Evaluation of Structural Stability of UapA Membrane Protein of TMG

An experiment of measuring structural stability of a uric acid-xanthine/H+ symporter (UapA) separated from *Aspergillus nidulans* by TMG was performed. The structural stability of UapA was evaluated using a sulfhydryl-specific fluorophore and N-[4-(7-diethylamino-4-methyl-3-coumarinyl)phenyl]maleimide (CPM).

Specifically, UapAG411V$_{1-11}$ (hereinafter, referred to as "UapA") expressed as a GFP fusion protein from a *Saccharomyces cerevisiae* FGY217 strain, and the protein was separated using a sample buffer (20 mM Tris (pH 7.5), 150 mM NaCl, 0.03% DDM, 0.6 mM xanthine) according to a method disclosed in the article written by J. Leung et al. (*Mol. Membr. Biol.* 2013, 30, 32-42). The protein having a molecular weight of 100 kDa was concentrated to approximately 10 mg/mL using a cut-off filter (Millipore). The protein was diluted with a buffer containing each of the TMG-As (TMG-A11, TMG-A12, TMG-A13 and TMG-A14), TMG-Ts (TMG-T11, TMG-T12, TMG-T13 and TMG-T14), MNG-3 or DDM at a ratio of 1:150 to reach the final concentration of CMC+0.04 wt % or CMC+0.2 wt % in a Greiner 96-well plate. A CPM dye (Invitrogen) stored in DMSO (Sigma) was diluted with a staining buffer (20 mM Tris (pH 7.5), 150 mM NaCl, 0.03% DDM, 5 mM EDTA), and 3 µL of the staining buffer was added to each sample. The reaction mixture was incubated at a constant temperature for 125 minutes at 40° C. Fluorescence emission was recorded using a microplate spectrofluorometer set to each of excitation and emission wavelengths of 387 nm and 463 nm. A relative amount of folded proteins was plotted over time using GraphPad Prism.

Figure 9:
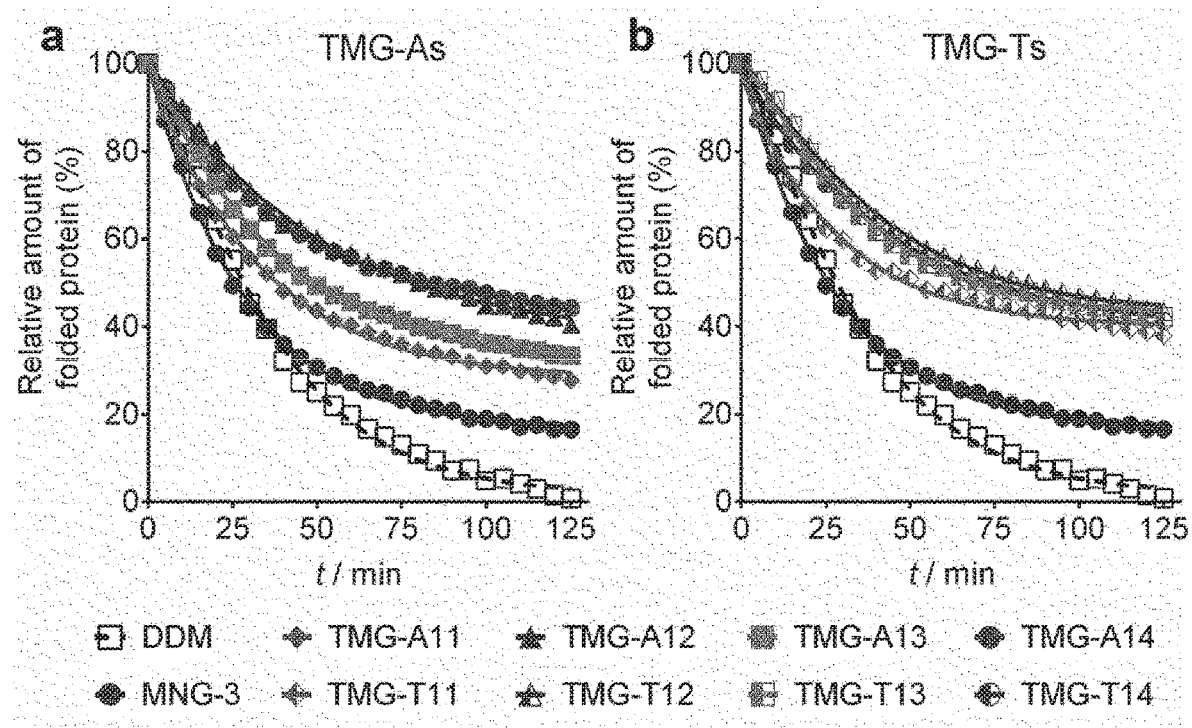
FIG. 9 shows the result of measuring thermal stability of UapA proteins solubilized in an aqueous solution by CMC+ 0.04 wt % TMGs or DDM using sulfhydryl-specific fluorophores and CPM:
  (a) TMG-As
  (b) TMG-Ts.
Figure 10:
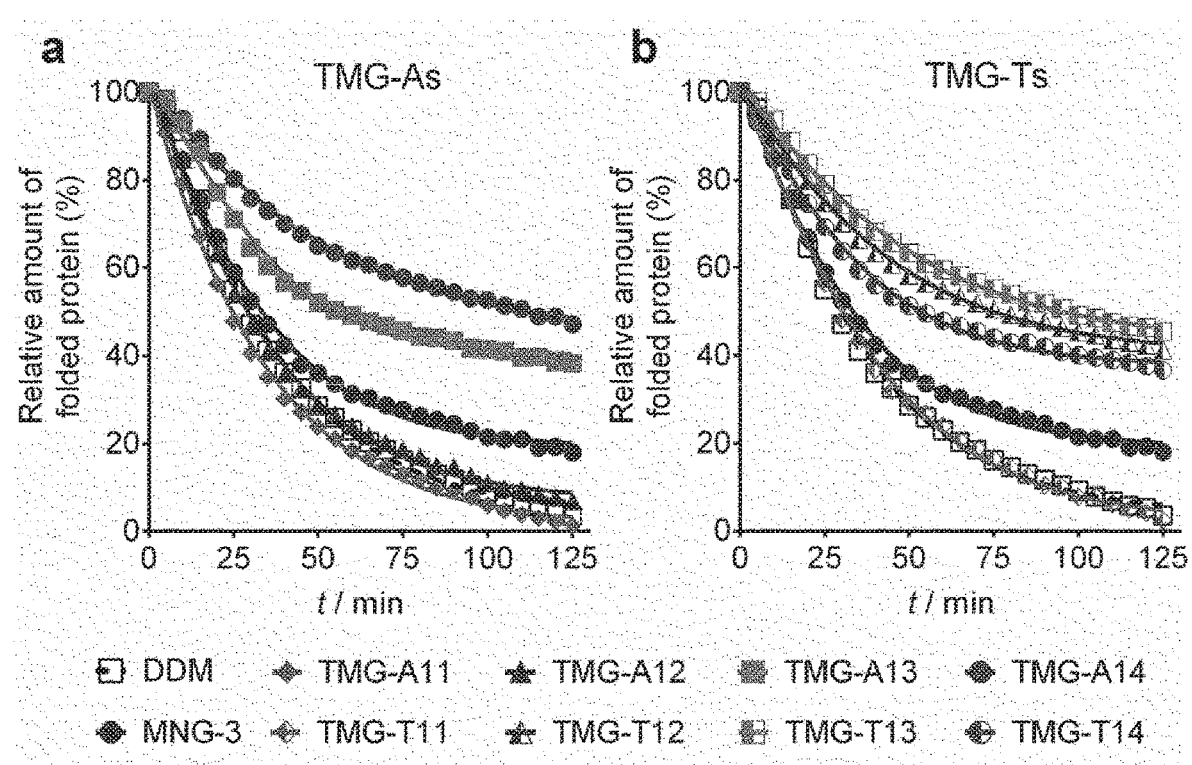
FIG. 10 shows the result of measuring thermal stability of UapA proteins solubilized in an aqueous solution by CMC+ 0.2 wt % TMGs or DDM using sulfhydryl-specific fluorophores and CPM:
  (a) TMG-As
  (b) TMG-Ts.

The intensity of fluorescence emission may be increased according to an amount of proteins in a sample, which was unfolded, that is, denatured, and CPM may be performed to rapidly screen the amount of denatured proteins according to this analysis. All TMGs exhibited a significantly excellent ability to conserve a transporter in a folded state, compared to DDM (FIG. 9). In addition, when the amphipathic molecules were measured at CMC+0.04 wt %, TMG-Ts were generally further more excellent in transporter stability than TMG-As. Among TMGs, TMG-A (TMA-A11) having the shortest alkyl chain was the least excellent in transporter stability. Even when the concentration of the amphipathic molecule was increased to CMC+0.2 wt %, generally, TMG-Ts have an excellent ability to conserve the transporter in a folded state, compared to TMG-As. Even at this concentration, among TMGs, TMGs (TMG-A11/T11) having the shortest alkyl chain were the least effective, and had lower stability than DDM. Meanwhile, TMGs having a long chain (TMG-A13/A14 or TMG-T13/T14) showed an excellent effect of stabilizing transporter folding. Such a result showed that, when the transporter is stabilized, TMGs having a long alkyl chain (TMG-T13/A14) were preferable to TMGs (TMG-T11/A11) having a short alkyl chain (FIGS. 9 and 10). One notable fact is that TMG amphipathic molecules have an excellent ability to maintain the transporter structure, compared to MNG-3 having a maltoside hydrophilic group. In terms of the ability to maintain the transporter structure, MNG-3 was a little superior to DDM.

<Example 8> Evaluation of LeuT Membrane Protein Stability Extracted by TMGs and TMMs An experiment of measuring LeuT protein stability for TMGs and TMMs was performed. (a) CMC+0.04 wt % or (b) CMC+0.2 wt % of each amphipathic molecule was used, and the evaluation of the LeuT protein stability was performed by taking an advantage of a characteristic of LeuT binding to a substrate through a scintillation proximity assay (SPA) using [$^3$H]-Leu. Measurement was performed at regular intervals during 10-day incubation at room temperature.

Specifically, wild type LeuT (leucine transporter) derived from a thermophilic bacterium, *Aquifex aeolicus*, was purified by a previously-disclosed method (G. Deckert et al., *Nature* 1998, 392, 353-358). LeuT was expressed in *E. coli* C41 (DE3) transformed with pET16b encoding a C-terminus 8×His-tagged transporter (the expression plasmid was provided by Dr E. Gouaux, Vollum Institute, Portland, Oreg., USA). In summary, following isolation of a bacterial membrane and lysis with 1% (w/v) DDM, the protein was allowed to bind to a Ni$^{2+}$-NTA resin (Life Technologies, Denmark), and eluted in 20 mM Tris-HCl (pH 8.0), 1 mM NaCl, 199 mM KCl, 0.05% (w/v) DDM and 300 mM imidazole. Afterward, the purified LeuT (approximately 1.5 mg/ml) was diluted with the same buffer used above, from which DDM and imidazole were removed, and then supplemented with TMGs or DDM at the final concentration of CMC+0.04% (w/v). A protein sample was stored for 10 days at room temperature and centrifuged for a predetermined time, and then characteristics of the protein were identified by measuring a substrate ([$^3$H]-Leucine)-binding ability using SPA. SPA was performed using a buffer containing 450 mM NaCl and each of the TMGs and TMMs at the predetermined concentration. The SPA reaction is performed in the presence of 20 nM [$^3$H]-Leucine and 1.25 mg/ml copper chelate (His-Tag) YSi beads (Perkin Elmer, Denmark). A total [$^3$H]-Leucine binding degree of each sample was measured using a MicroBeta liquid scintillation counter (Perkin Elmer).

Figure 11:
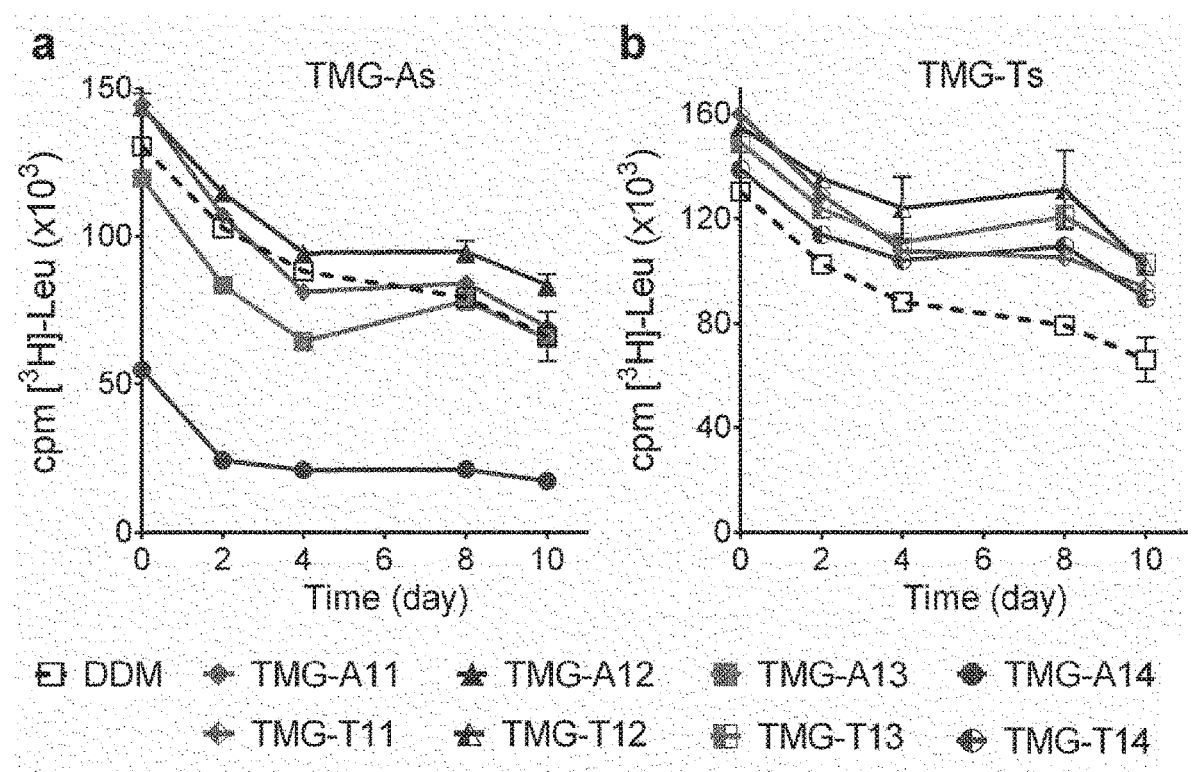
FIG. 11 shows the result of measuring structural stability of a leucine transporter (LeuT) solubilized by CMC+0.2 wt % TMGs or DDM. The protein stabilization is confirmed by measuring a substrate-binding characteristic of a transporter through a SPA. In the presence of each amphipathic molecule, LeuT is incubated at room temperature for 10 days, and the substrate-binding characteristic of the protein is measured at regular intervals:
  (a) TMG-As
  (b) TMG-Ts.
Figure 12:
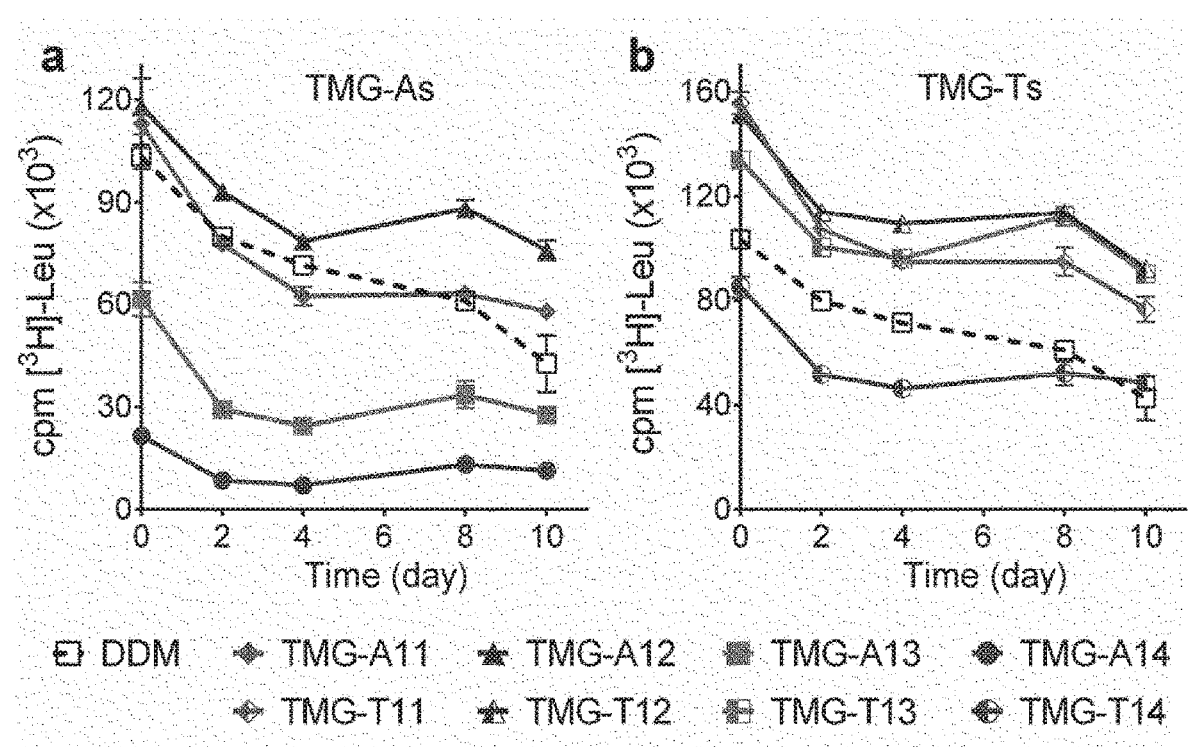
FIG. 12 shows the result of measuring structural stability of a leucine transporter (LeuT) solubilized by CMC+0.04 wt % TMGs or DDM. The protein stabilization is confirmed by measuring a substrate-binding characteristic of a transporter through a SPA. In the presence of each amphipathic molecule, LeuT is incubated at room temperature for 10 days, and the substrate-binding characteristic of the protein is measured at regular intervals:
  (a) TMG-As
  (b) TMG-Ts.

As a result, in the case of TMG-As, only in a LeuT sample solubilized by TMG-A12 at a relatively low concentration (CMC+0.04 wt %), exhibited a substantially higher substrate-binding ability of the transporter than DDM (FIG. 11). Such an improved substrate-binding ability, compared to DDM, was well maintained for 10 days in the case of LeuT solubilized by TMG-A12. Even when the concentration of the amphipathic molecule was increased to CMC+0.2 wt %, TMG-As showed a tendency similar to the above result (FIG. 12). TMG-Ts were more excellent in conservation of the substrate-binding ability of the transporter than TMG-As (FIGS. 11 and 12). At the low concentration (CMC+0.04 wt %), all TMG-Ts (TMG-T11/T12/T13/T14) exhibited a better characteristic than DDM (FIG. 11), and even when the concentration of the amphipathic molecule was increased (CMC+0.04 wt %), TMG-Ts were more effective in conserving the substrate-binding ability of the transporter than DDM (FIG. 12).

Figures 13A, 13B:
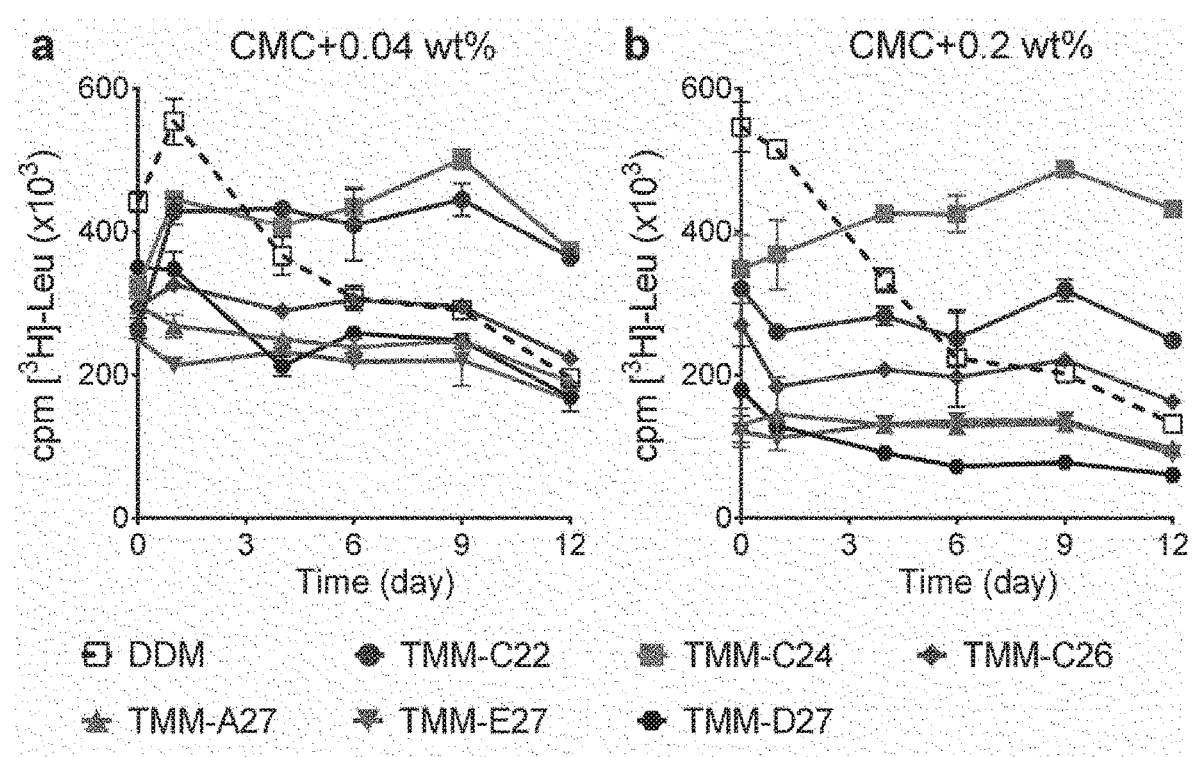
FIGS. 13a and 13b show the result of measuring structural stability of a leucine transporter (LeuT) solubilized by CMC +0.04 wt% (a) and CMC +0.2 wt% (b) TMMs or DDM. The protein stabilization is confirmed by measuring a substrate-binding characteristic of a transporter through a SPA. In the presence of each amphipathic molecule, LeuT is incubated at room temperature for 10 days, and the substrate-binding characteristic of the protein is measured at regular intervals.

When the concentration was reduced to CMC+0.04 wt %, in the case of TMMs, the initial activity of LeuT (substrate-binding ability) was a little lower than when DDM was used. However, in the case of DDM, the activity of the transporter was gradually reduced over time, and in the case of a new TMM, a great decrease in protein activity was not shown over time. Particularly, in the case of TMM-C22 and TMM-C24, the activity of the transporter was slightly increased over time. Consequently, after incubation for 12 days at room temperature, the activity of the transporter solubilized by these two amphipathic molecules was measured to be two-fold higher than that of the protein dissolved in DDM. Meanwhile, after 12-day incubation, in the case of TMG-C26 and the amphipathic molecules having a steroid hydrophobic group (TMM-A27, TMM-E27 and TMM-D27), protein activity similar to DDM was exhibited (FIG. 13a). In addition, when the experiment was performed by raising the concentration to CMC+0.2 wt %, it can be confirmed that a similar tendency was shown to the result obtained at a low concentration (FIG. 13b).

Consequently, among the TMM amphipathic molecules, TMM-C24 had the most excellent characteristic and was superior to DDM, followed by TMM-C22 and TMM-C26. The TMMs having a steroid hydrophobic group overall exhibited a characteristic inferior to DDM. Therefore, two amphipathic molecules such as TMM-C24 and TMM-C22 were considered to have potential for analysis of the structure of the transporter.

<Example 9> Measurement of Long-Term Stability of β$_2$AR for TMGs

Experiments for measuring stability of a human β$_2$ adrenergic receptor (β$_2$AR) and a G-protein-coupled receptor (GPCR) by TMGs were performed. A receptor was extracted from a cell membrane using 1% DDM and purified with a 0.1% amphipathic molecule. The receptor purified with the DDM was diluted with a buffer solution containing DDM or TMGs to adjust the final concentration of the compound to CMC+0.2 wt %. β$_2$AR solubilized by each amphipathic molecule was stored for 7 days at room temperature, and the sample was incubated with 10 nM [$^3$H]-dihydroalprenolol (DHA) supplemented with 0.5 mg/ml BSA for 30 minutes at room temperature to evaluate a ligand-binding ability at regular intervals during the experimental period. The mixture was loaded onto a G-50 column, and a liquid running through the column was collected using 1 ml of a binding buffer (20 mM HEPES containing 0.5 mg/ml BSA and 20×CMC of each amphipathic molecule, pH 7.5, 100 mM NaCl). In addition, 15 ml of a scintillation fluid was added, and receptor-bound [$^3$H]-DHA was measured using a scintillation counter (Beckman). A binding degree of the [$^3$H]-

Figure 14:
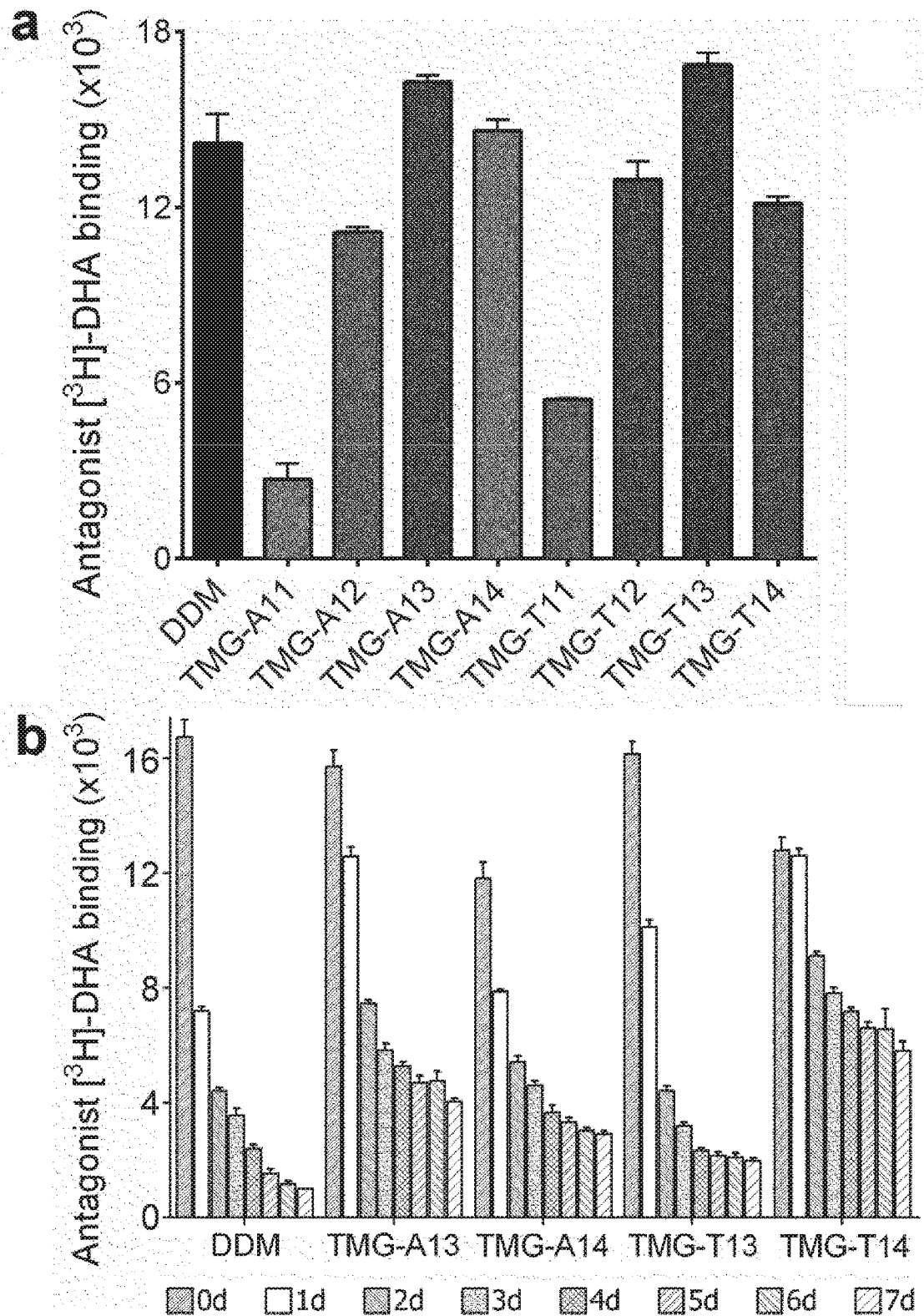
FIG. 14 shows the result of measuring (a) an initial ligand-binding ability of $\beta_2$AR extracted and solubilized from a cell membrane by CMC+0.2 wt % TMGs or DDM, and (b) a long-term ligand-binding ability of $\beta_2$AR extracted and solubilized from a cell membrane by TMGs (TMG-A13, TMG-A14, TMG-T13, TMG-T14) or DDM through a ligand binding assay using [³H]-dihydroalprenolol (DHA) at regular intervals for 7 days.

DHA was shown by a column graph (FIG. 14). The experiment was repeated three times.

Figure 15:
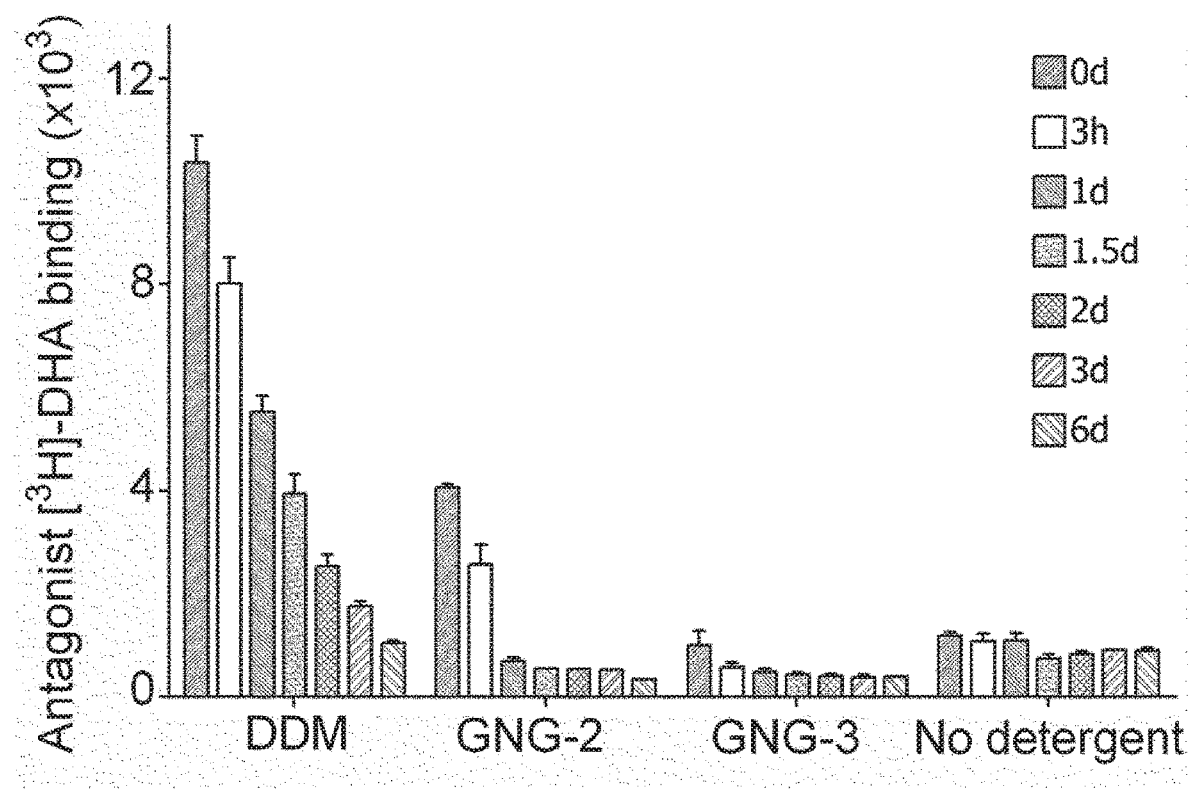
FIG. 15 is a graph obtained by measuring long-term activity of $\beta_2$AR dissolved in DDM, GNG-2 or GNG-3 at regular intervals for 6 days. The protein activity is confirmed by measuring a binding ability to [³H]-DHA, which is a ligand, and as a control, the same experiment is performed under a condition in which there is no novel amphipathic molecule (detergent-free condition)

As a result, particularly, it was confirmed that only some TMGs such as TMG-A13/A14 and TMG-T13/T14 are as effective as DDM in terms of maintenance of the initial receptor activity. As a result of regularly monitoring the receptor activity for TMGs exhibiting an excellent effect of maintaining the binding between a receptor and a ligand for 7-day incubation at room temperature, TMG-A13/A14 and TMG-T13/T14 were superior to DDM in terms of long-term maintenance of binding between the receptor and the ligand (FIG. 14). Particularly, TMG-A14 and TMG-T14 were superior to DDM in terms of long-term maintenance of binding between the receptor and the ligand, but inferior to DDM in terms of initial binding between the receptor and the ligand. Among TMGs, TMG-T14 was most excellent in maintenance of binding between a receptor and a ligand, followed by TMG-A13 and TMG-A14 (FIG. 14). This result shows that TMG-A13 and TMG-T14 may have critical potential in GPCR research. However, it can be seen that conventional new glucoside amphipathic molecules, GNG-2 and GNG-3, were not suitable for GRCR research due to a low initial receptor activity and decreased activity over time (FIG. 15). In addition, when a sample was diluted to exchange the amphipathic molecule, under a detergent-free condition, the detected receptor activity was very low. That is, a protein activity was not able to be maintained without the aid of a new TMG amphipathic molecule.

<Example 10> Evaluation of Ability of Structural Stabilization of MelB$_{St}$ Membrane Protein of TMGs An experiment was performed to measure structural stability of *Salmonella typhimurium* melibiose permease (MelB$_{St}$) protein by TMGs. The MelB$_{St}$ protein was extracted from a membrane using TMGs or DDM, and then an amount of the extracted protein and its structure were analyzed by SDS-PAGE and western blotting. A concentration of the amphipathic molecule used was 1.5 wt %, and two types of performance such as protein extraction efficiency and stabilization ability of the compound were simultaneously evaluated by extracting the protein at four temperatures (0, 45, 55, and 65° C.), incubating the protein for 90 minutes at the same temperatures, and measuring an amount of the protein remaining dissolved in an aqueous solution. The amount of the protein extracted and stabilized by each amphipathic molecule was expressed as a relative value (%) with respect to a total amount of the protein contained in a membrane sample not treated with an amphipathic molecule.

Specifically, *Salmonella typhimurium* MelB$_{St}$ (melibiose permease) having a 10-His tag at the C-terminus was expressed in *E. coli* DW2 cells (melB and lacZY) using plasmid pK95AHB/WT MelB$_{St}$/CH$_{10}$. According to the method disclosed in the article written by A. S. Ethayathulla et al. (*Nat. Commun.* 2014, 5, 2009), cell growth and membrane preparation were performed. A protein assay was performed using a Micro BCA kit (Thermo Scientific, Rockford, Ill.). Using the protocol disclosed in *Nat. Methods* 2010, 7, 1003-1008 written by P. S. Chae et al., DDM or TMGs were evaluated for MelB$_{St}$ stability. A MelB$_{St}$-containing membrane sample (the final protein concentration was 10 mg/mL) was incubated at four temperatures (0, 45, 55 and 65° C.) for 90 minutes in a 1.5% (w/v) DDM or TMG-containing solubilization buffer (20 mM sodium phosphate, pH 7.5, 200 mM NaCl, 10% glycerol, 20 mM melibiose). To remove insoluble material, ultracentrifugation was performed using a Beckman Optima™ MAX ultracentrifuge equipped with a TLA-100 rotor at 355,590 g at 4° C. for 45 minutes, and then 20 μg of each protein sample was separated using SDS-15% PAGE, followed by immunoblotting using a Penta-His-HRP antibody (Qiagen, Germantown, Md.). MelB$_{St}$ was measured by an ImageQuant LAS 4000 biomolecular imager (GE Health Care Life Sciences) using a SuperSignal West Pico chemiluminescent substrate.

Figure 16:
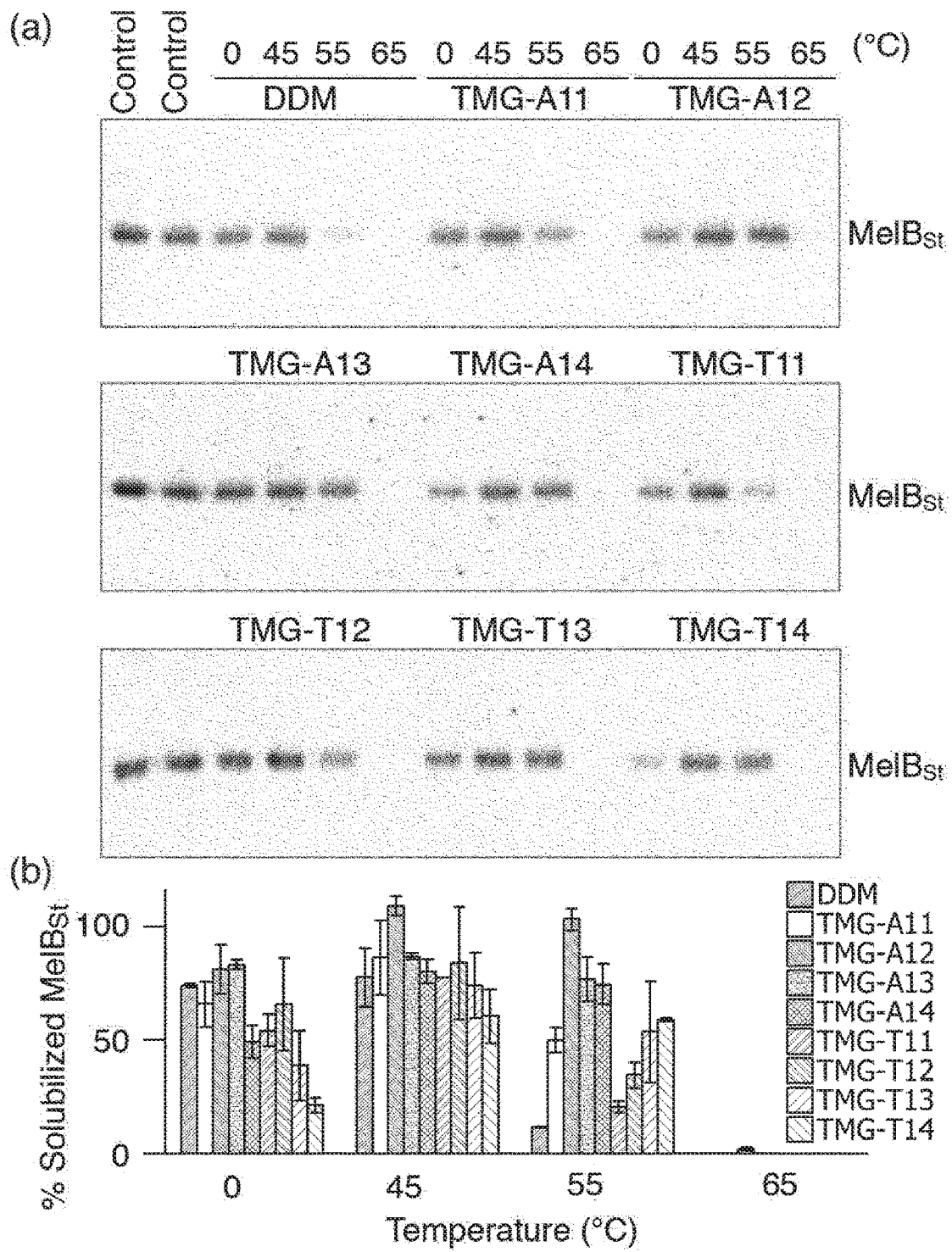
FIG. 16 is the result of measuring an amount of $MelB_{St}$ protein dissolved in an aqueous solution after the $MelB_{St}$ protein is extracted at four temperatures (0, 45, 55, 65° C.) using TMGs or DDM at a concentration of 1.5 wt %, and then incubated for 90 minutes at the same temperatures.

An amount of MelB$_{St}$ solubilized at 0° C. was lower in all TMGs, excluding TMG-A12 and TMG-A13, compared to DDM. However, as an incubation temperature was increased to 45° C., compared to DDM, all TMGs excluding TMG-T14 allowed the solubility of MelB$_{St}$ to be more excellently maintained. Particularly, almost all MelB$_{St}$ was successfully extracted at this temperature using TMG-A12, and such excellent protein extraction efficiency was able to be confirmed even at 55° C. That is, TMG-A12 allowed the MelB$_{St}$ protein to be more efficiently extracted and allowed the extracted MelB$_{St}$ solubility to be excellently maintained. In contrast, DDM allowed solubilization of only 10% of the extracted MelB$_{St}$ to be maintained at 55° C. For DDM and all TMGs, the MelB$_{St}$ protein dissolved in an aqueous solution was not detected at 65° C. (FIG. 16).

Overall, DDM showed slightly more excellent protein extraction efficiency than TMGs at a low temperature (0° C.), whereas TMGs had protein extraction efficiency similar to DDM at a relatively high temperature (45° C.) and protein extraction efficiency superior to DDM at a higher temperature (55° C.). Therefore, it can be seen that DDM exhibited excellent protein extraction efficiency, but TMGs exhibited a significantly excellent protein stabilization ability (FIG. 16).

Membrane proteins can be stably stored in an aqueous solution for a long time using tandem malonate-based compounds according to exemplary embodiments of the present invention, compared to conventional compounds, and therefore, can be used in analysis of their functions and structures.

The analysis of the structures and functions of the membrane proteins is one of the most interesting fields in current biology and chemistry, and thus can be applied in research on the structures of proteins closely related to new drug development.

In addition, since the compounds according to the exemplary embodiments of the present invention have a small size in formation of complexes with membrane proteins, high-quality membrane protein crystals can be obtained, and thus can promote crystallization of membrane proteins.

In addition, the compounds according to exemplary embodiments of the present invention can be synthesized by a simple method from a starting material which can be easily obtained, and thus can be mass-produced to study membrane proteins.

Above, the present invention has been described with reference to exemplary examples, but it can be understood by those of ordinary skill in the art that the present invention may be changed and modified in various forms without departing from the spirit and scope of the present invention which are described in the accompanying claims.

What is claimed is:

1. A compound represented by the following Formula 1:

[Formula 1]

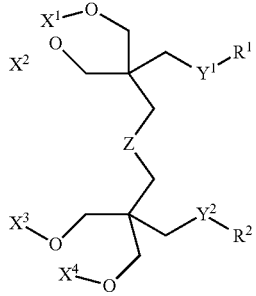

where $R^1$ and $R^2$ are each independently a substituted or unsubstituted $C_3$-$C_{30}$ alkyl group, a substituted or unsubstituted $C_3$-$C_{30}$ cycloalkyl group, a substituted or unsubstituted $C_3$-$C_{30}$ aryl group or an organic group having a steroid backbone;

each of $X^1$ to $X^4$ is a saccharide;
each of $Y^1$ and $Y^2$ is $CH_2$, O or S; and
Z is $CH_2$ or S.

2. The compound of claim 1, wherein the saccharide is a monosaccharide or a disaccharide.

3. The compound of claim 1, wherein the saccharide is glucose or maltose.

4. The compound of claim 1, wherein the $R^1$ and $R^2$ are each independently a substituted or unsubstituted $C_3$-$C_{30}$ alkyl group; each of $X^1$ to $X^4$ is glucose or maltose; each of $Y^1$ and $Y^2$ is $CH_2$; and Z is $CH_2$.

5. The compound of claim 1, wherein $R^1$ and $R^2$ are each independently a substituted or unsubstituted $C_3$-$C_{30}$ alkyl group; each of $X^1$ to $X^4$ is glucose or maltose; each of $Y^1$ and $Y^2$ is O or S; and Z is S.

6. The compound of claim 1, wherein each of $R^1$ and $R^2$ is an organic group having a steroid backbone; each of $X^1$ to $X^4$ is maltose; each of $Y^1$ and $Y^2$ is O or S; and Z is S.

7. The compound of claim 1, wherein the compound is any compound represented by the following Formulas 2 to 15:

[Formula 2]

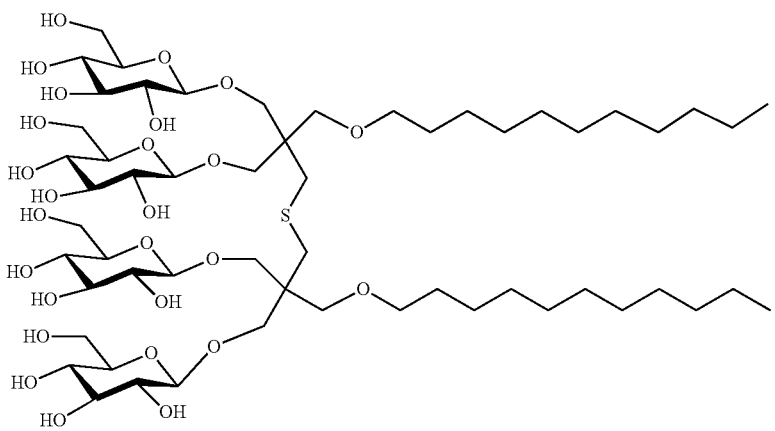

[Formula 3]

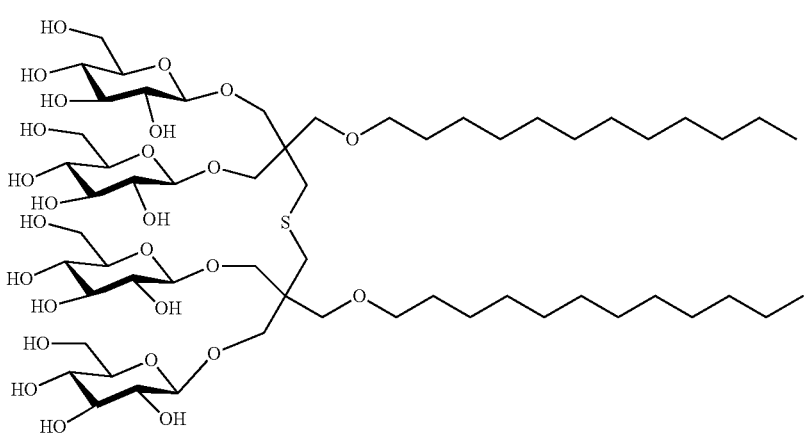

[Formula 4]
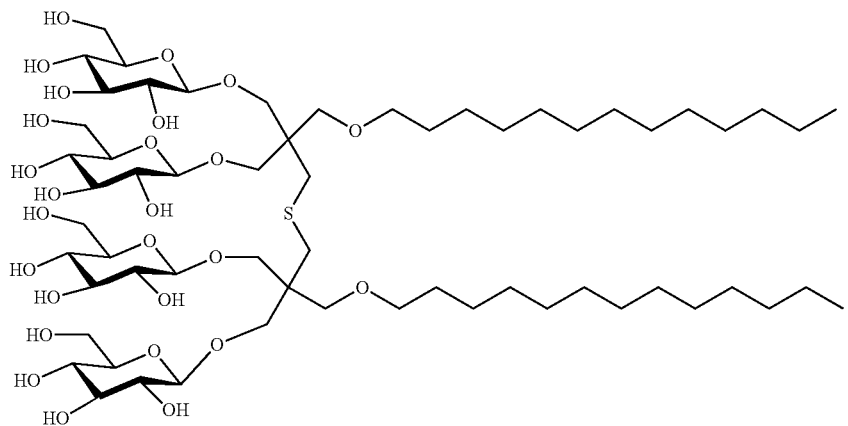
(Formula 5]
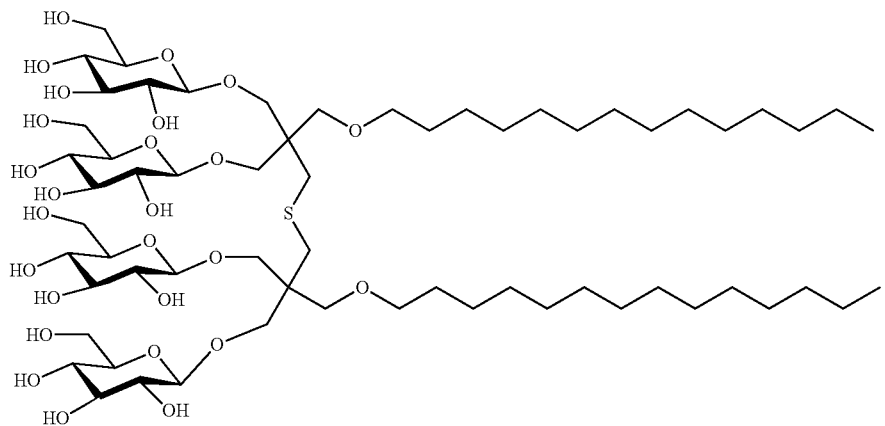
[Formula 6]
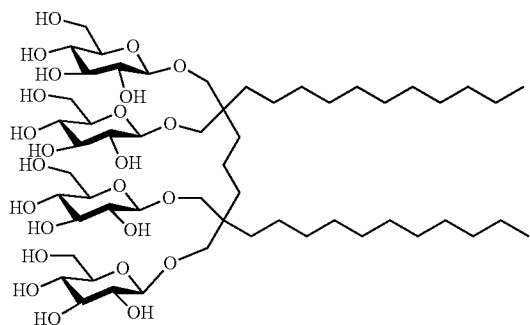
[Formula 7]
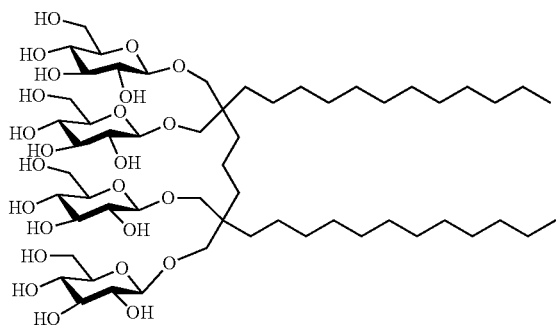
[Formula 8]
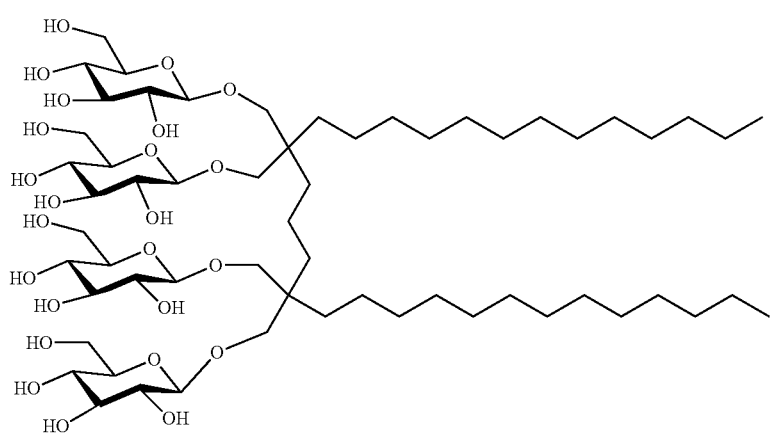

[Formula 9]
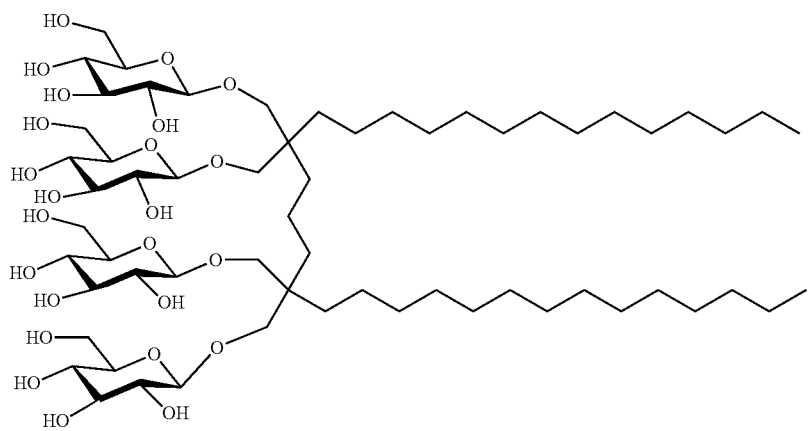
[Formula 10]
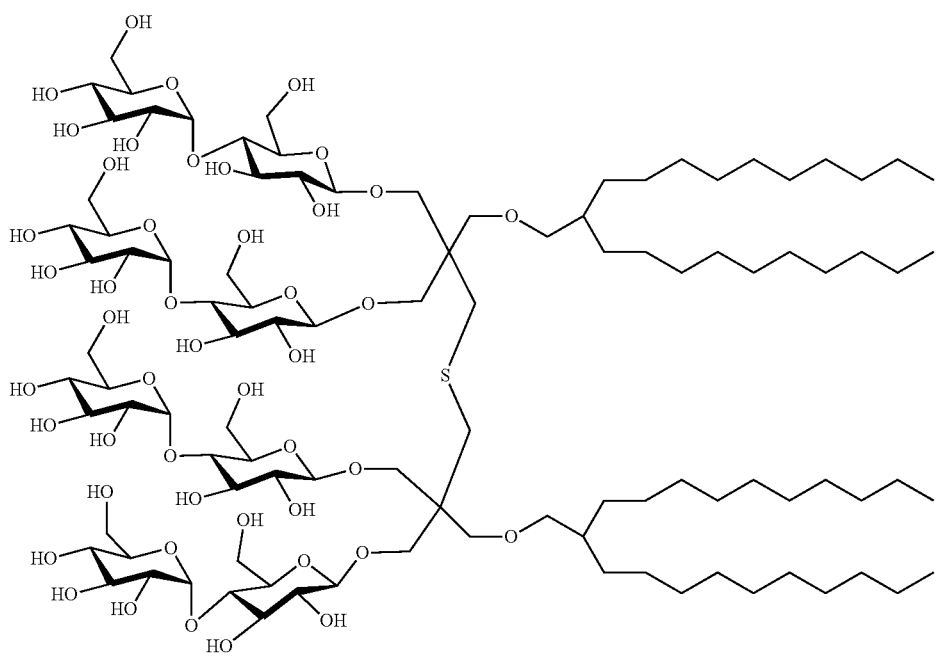

[Formula 11]
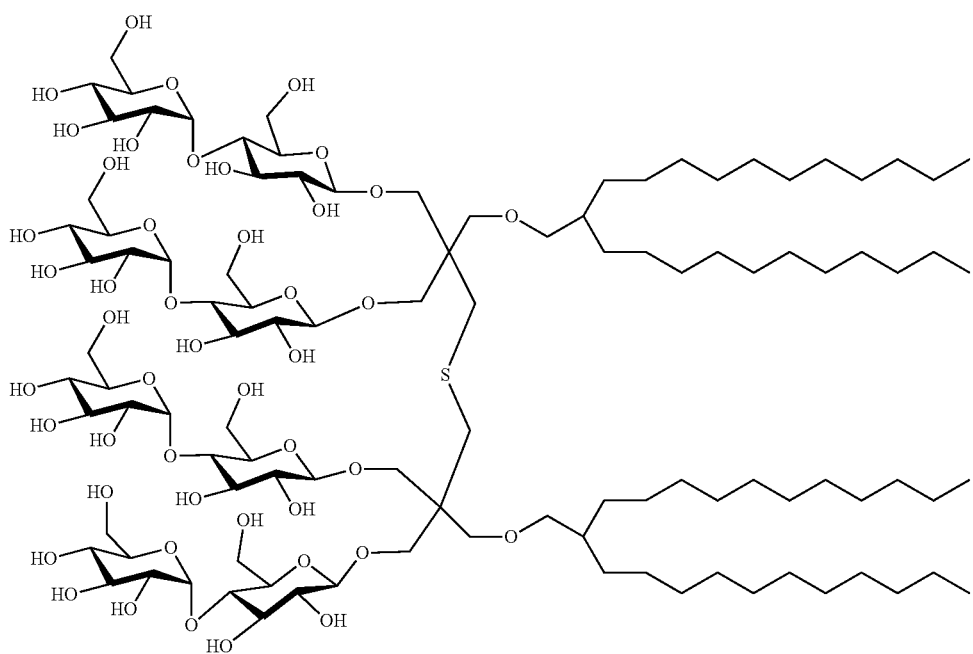
[Formula 12]
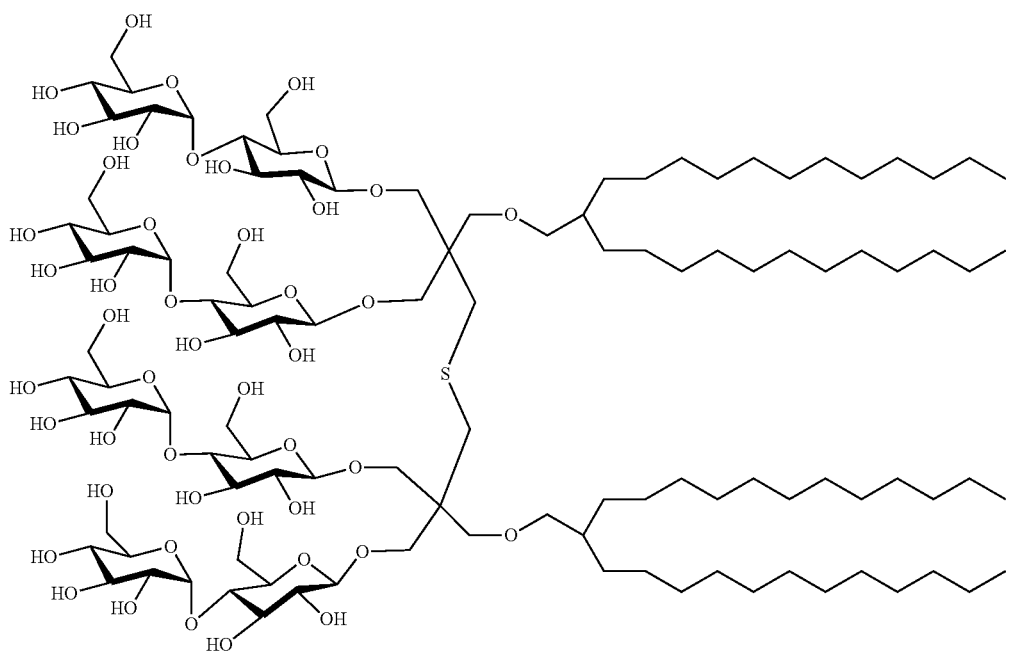

[Formula 13]
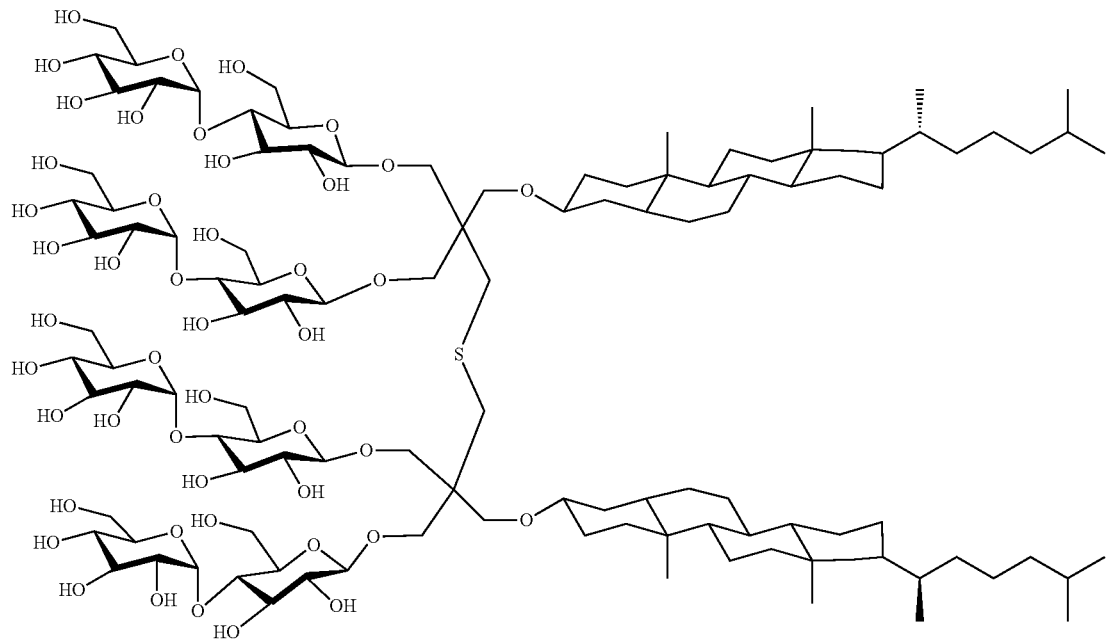
[Formula 14]
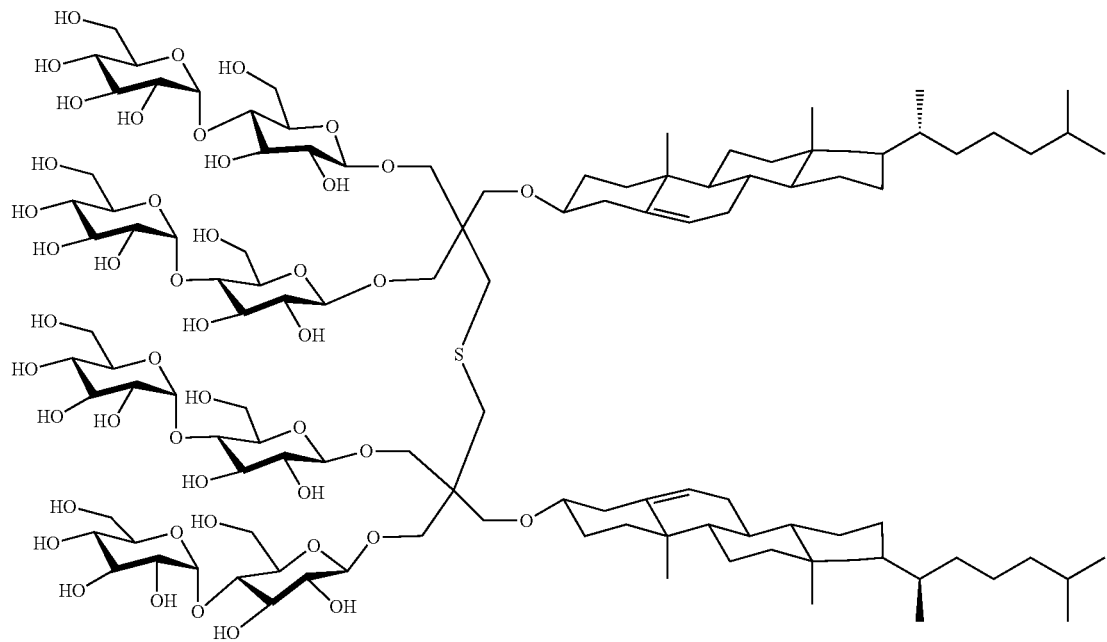

-continued

[Formula 15]

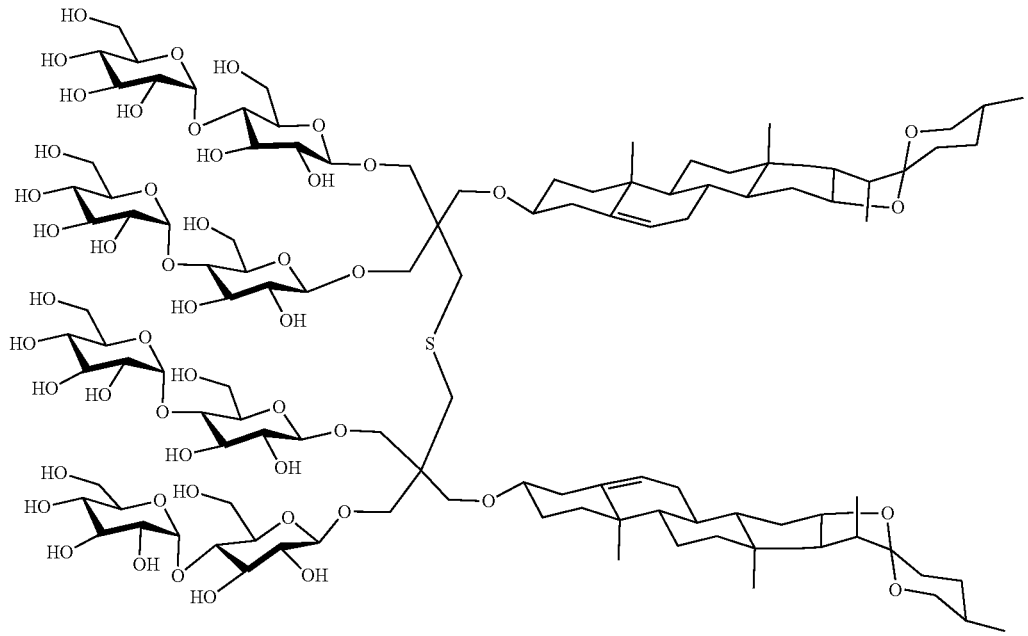

8. The compound of claim 1, wherein the compound is an amphipathic molecule for extracting, solubilizing, stabilizing, crystallizing or analyzing a membrane protein.

9. The compound of claim 1, wherein the compound has a critical micelle concentration (CMC) of 0.0001 to 1 mM in an aqueous solution.

10. A composition for extracting, solubilizing, stabilizing, crystallizing or analyzing a membrane protein, comprising the compound of claim 1.

11. The compound of claim 10, wherein the composition is prepared in the form of micelles, liposomes, an emulsion or nanoparticles.

12. A method of preparing a compound represented by the following Formula 1, comprising:

1) synthesizing tetramethyl pentane-1,1,5,5-tetracarboxylate by linking two dimethyl malonate molecules with an alkyl chain;
2) introducing an alkyl chain by performing an alkylation reaction on two α-carbons present in the product of step 1);
3) reducing four methyl carboxylate groups of the product of step 2) to alcohols;
4) introducing a protective group-attached saccharide by performing a glycosylation reaction on the product of step 3); and
5) performing a deprotection reaction on the product of step 4):

[Formula 1]

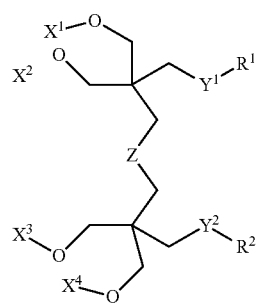

where $R^1$ and $R^2$ are each independently a substituted or unsubstituted $C_3$-$C_{30}$ alkyl group, a substituted or unsubstituted $C_3$-$C_{30}$ cycloalkyl group, or a substituted or unsubstituted $C_3$-$C_{30}$ aryl group;

each of $X^1$ to $X^4$ is a saccharide;

each of $Y^1$ and $Y^2$ is $CH_2$; and

Z is $CH_2$.

13. A method of preparing a compound represented by the following Formula 1, comprising:

1) synthesizing thioether-containing tetraol by adding 5,5-bis-bromomethyl-2,2-dimethyl-[1,3]dioxane to a solution of 1-alkanol, dialkylated mono-ol, cholesterol, cholestanol or diosgenin;
2) introducing a protective group-attached saccharide by performing a glycosylation reaction on the product of step 1); and
3) performing a deprotection reaction on the product of step 2):

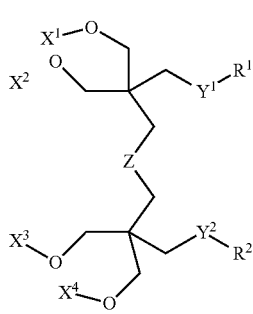

where $R^1$ and $R^2$ are each independently a substituted or unsubstituted $C_3$-$C_{30}$ alkyl group, a substituted or unsubstituted $C_3$-$C_{30}$ cycloalkyl group, a substituted or unsubstituted $C_3$-$C_{30}$ aryl group or an organic group having a steroid backbone;
each of $X^1$ to $X^4$ is a saccharide;
each of $Y^1$ and $Y^2$ is O or S; and
Z is S.

14. The method of claim 12, wherein $R^1$ and $R^2$ are each independently a substituted or unsubstituted $C_3$-$C_{30}$ alkyl group or an organic group having a steroid backbone; and each of $X^1$ to $X^4$ is glucose or maltose.

15. A method of extracting, solubilizing, stabilizing, crystallizing or analyzing a membrane protein, comprising:
treating a membrane protein with a compound represented by the following Formula 1 in an aqueous solution:

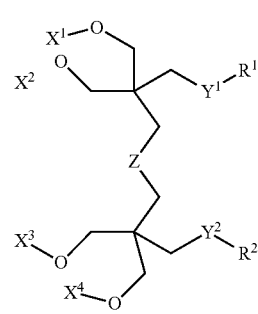

where $R^1$ and $R^2$ are each independently a substituted or unsubstituted $C_3$-$C_{30}$ alkyl group, a substituted or unsubstituted $C_3$-$C_{30}$ cycloalkyl group, a substituted or unsubstituted $C_3$-$C_{30}$ aryl group or an organic group having a steroid backbone;
each of $X^1$ to $X^4$ is a saccharide;
each of $Y^1$ and $Y^2$ is $CH_2$, O or S; and
Z is $CH_2$ or S.

16. The method of claim 15, wherein $R^1$ and $R^2$ are each independently a substituted or unsubstituted $C_3$-$C_{30}$ alkyl group; each of $X^1$ to $X^4$ is glucose or maltose; each of $Y^1$ and $Y^2$ is $CH_2$; and Z is $CH_2$.

17. The method of claim 15, wherein $R^1$ and $R^2$ are each independently a substituted or unsubstituted $C_3$-$C_{30}$ alkyl group; each of $X^1$ to $X^4$ is glucose or maltose; each of $Y^1$ and $Y^2$ is O or S; and Z is S.

18. The method of claim 15, wherein each of $R^1$ and $R^2$ is an organic group having a steroid backbone; each of $X^1$ to $X^4$ is maltose; each of $Y^1$ and $Y^2$ is O or S; and Z is S.

19. The method of claim 15, wherein the membrane protein is a uric acid-xanthine/H+ symporter (UapA), a leucine transporter (LeuT), a human ($\beta_2$ adrenergic receptor ($\beta_2$AR), melibiose permease ($MelB_{st}$), or a combination of two or more thereof.

* * * * *